US012239412B2

(12) United States Patent
Petroff et al.

(10) Patent No.: US 12,239,412 B2
(45) Date of Patent: Mar. 4, 2025

(54) SYSTEMS AND METHODS FOR OCT-GUIDED TREATMENT OF A PATIENT

(71) Applicant: Spryte Medical, Inc., Bedford, MA (US)

(72) Inventors: Christopher C. Petroff, Groton, MA (US); Christopher L. Petersen, Carlisle, MA (US); David W. Kolstad, Carlisle, MA (US); Giovanni J. Ughi, Arlington, MA (US); Lindsy M. Peterson, Woburn, MA (US); Benjamin Duncan, Watertown, MA (US); R. Maxwell Flaherty, Topsfield, MA (US); J. Christopher Flaherty, Nottingham, NH (US)

(73) Assignee: Spryte Medical, Inc., Bedford, MA (US)

( * ) Notice: Subject to any disclaimer, the term of this patent is extended or adjusted under 35 U.S.C. 154(b) by 420 days.

(21) Appl. No.: 17/603,689

(22) PCT Filed: May 21, 2020

(86) PCT No.: PCT/US2020/033953
§ 371 (c)(1),
(2) Date: Oct. 14, 2021

(87) PCT Pub. No.: WO2020/237024
PCT Pub. Date: Nov. 26, 2020

(65) Prior Publication Data
US 2022/0061670 A1     Mar. 3, 2022

Related U.S. Application Data

(60) Provisional application No. 63/017,258, filed on Apr. 29, 2020, provisional application No. 62/906,353,
(Continued)

(51) Int. Cl.
*A61B 5/00*  (2006.01)
*A61B 90/00*  (2016.01)

(52) U.S. Cl.
CPC .......... *A61B 5/0066* (2013.01); *A61B 5/0044* (2013.01); *A61B 5/0084* (2013.01);
(Continued)

(58) Field of Classification Search
CPC ... A61B 5/0035; A61B 5/0066; A61B 5/0084; A61B 5/0044
See application file for complete search history.

(56) References Cited

U.S. PATENT DOCUMENTS 4,460,989 A    7/1984 Russell
4,554,929 A    11/1985 Samson et al.
(Continued)

FOREIGN PATENT DOCUMENTS

AU    2014200116    1/2014
CN    1684624       10/2005
(Continued)

OTHER PUBLICATIONS

Abozenadah, H., et al. Consumer Chemistry: How Organic Chemistry Impacts Our Lives. CC BY-NC-SA. Available at: https://wou.edu/chemistry/courses/online-chemistry-textbooks/ch105-consumer-chemistry/ (2017).
(Continued)

*Primary Examiner* — Joel Lamprecht
*Assistant Examiner* — Nyrobi Celestine
(74) *Attorney, Agent, or Firm* — Onello & Mello, LLP

(57) ABSTRACT

Provided herein are imaging systems for a patient comprising an imaging probe and an imaging assembly. The imaging probe comprises: an elongate shaft comprising a proximal end, a distal portion, and a lumen extending between the proximal end and the distal portion; a rotatable optical core
(Continued)

comprising a proximal end and a distal end, wherein at least a portion of the rotatable optical core is positioned within the lumen of the elongate shaft; and an optical assembly positioned proximate the distal end of the rotatable optical core, the optical assembly configured to direct light to tissue and collect reflected light from the tissue. The imaging assembly is constructed and arranged to optically couple to the imaging probe. The imaging assembly is configured to emit light into the imaging probe and receive the reflected light collected by the optical assembly. The system is configured to provide treatment information, wherein the treatment information is used by an operator to plan a treatment and/or predict a treatment outcome.

25 Claims, 21 Drawing Sheets

Related U.S. Application Data filed on Sep. 26, 2019, provisional application No. 62/850,945, filed on May 21, 2019.

(52) U.S. Cl.
CPC ...... *A61B 90/37* (2016.02); *A61B 2090/3735* (2016.02); *A61B 2090/376* (2016.02)

(56) References Cited

U.S. PATENT DOCUMENTS

| | | |
|---|---|---|
| 4,566,330 A | 1/1986 | Fujii et al. |
| 4,583,184 A | 4/1986 | Murase |
| 4,588,982 A | 5/1986 | Goodwin |
| 4,594,895 A | 6/1986 | Fujii |
| 4,597,292 A | 7/1986 | Fujii et al. |
| 4,646,748 A | 3/1987 | Fujii et al. |
| 4,753,248 A | 6/1988 | Engler et al. |
| 4,951,677 A | 8/1990 | Crowley et al. |
| 4,957,482 A | 9/1990 | Shiber |
| 4,961,427 A | 10/1990 | Namekawa et al. |
| 4,983,169 A | 1/1991 | Furukawa |
| 5,002,059 A | 3/1991 | Crowley et al. |
| 5,039,193 A | 8/1991 | Snow et al. |
| 5,058,587 A | 10/1991 | Kohno et al. |
| 5,118,405 A | 6/1992 | Kaneko et al. |
| 5,127,405 A | 7/1992 | Alcala et al. |
| 5,143,075 A | 9/1992 | Ishizuka |
| 5,151,603 A | 9/1992 | Nakamura |
| 5,152,277 A | 10/1992 | Honda et al. |
| 5,158,086 A | 10/1992 | Brown et al. |
| 5,212,671 A | 5/1993 | Fujii et al. |
| 5,219,335 A | 6/1993 | Willard et al. |
| 5,321,501 A | 6/1994 | Swanson et al. |
| 5,331,309 A | 7/1994 | Sakai |
| 5,383,467 A | 1/1995 | Auer et al. |
| 5,443,781 A | 8/1995 | Saab |
| 5,456,245 A | 10/1995 | Bornhop et al. |
| 5,459,570 A | 10/1995 | Swanson et al. |
| 5,502,567 A | 3/1996 | Pokrowsky et al. |
| 5,554,139 A | 9/1996 | Okajima |
| 5,568,314 A | 10/1996 | Omori et al. |
| 5,568,503 A | 10/1996 | Omori |
| 5,588,081 A | 12/1996 | Takahashi |
| 5,644,427 A | 7/1997 | Omori et al. |
| 5,647,359 A | 7/1997 | Kohno et al. |
| 5,649,897 A | 7/1997 | Nakamura et al. |
| 5,689,316 A | 11/1997 | Hattori et al. |
| 5,738,100 A | 4/1998 | Yagami et al. |
| 5,745,163 A | 4/1998 | Nakamura et al. |
| 5,774,175 A | 6/1998 | Hattori |
| 5,774,261 A | 6/1998 | Omori et al. |
| 5,793,341 A | 8/1998 | Omori et al. |
| 5,818,399 A | 10/1998 | Omori et al. |
| 5,827,242 A | 10/1998 | Follmer et al. |
| 5,860,923 A | 1/1999 | Lenker et al. |
| 5,976,017 A | 11/1999 | Omori et al. |
| 5,999,591 A | 12/1999 | Kobayashi et al. |
| 6,011,580 A | 1/2000 | Hattori et al. |
| 6,011,809 A | 1/2000 | Tosaka |
| 6,019,507 A | 2/2000 | Takaki |
| 6,019,737 A | 2/2000 | Murata |
| 6,033,383 A | 3/2000 | Ginsburg |
| 6,036,682 A | 3/2000 | Lange et al. |
| 6,052,613 A | 4/2000 | Takaki |
| 6,064,684 A | 5/2000 | Yoon et al. |
| 6,069,698 A | 5/2000 | Ozawa et al. |
| 6,115,058 A | 9/2000 | Omori et al. |
| 6,134,003 A | 10/2000 | Tearney et al. |
| 6,160,826 A | 12/2000 | Swanson et al. |
| 6,165,127 A | 12/2000 | Crowley |
| 6,191,862 B1 | 2/2001 | Swanson et al. |
| 6,208,887 B1 | 3/2001 | Clarke |
| 6,217,828 B1 | 4/2001 | Bretscher et al. |
| 6,283,632 B1 | 9/2001 | Takaki |
| 6,296,608 B1 | 10/2001 | Daniels et al. |
| 6,309,358 B1 | 10/2001 | Okubo |
| 6,341,036 B1 | 1/2002 | Tearney et al. |
| 6,364,841 B1 | 4/2002 | White et al. |
| 6,383,209 B1 | 5/2002 | Crowley |
| 6,445,939 B1 | 9/2002 | Swanson et al. |
| 6,449,500 B1 | 9/2002 | Asai et al. |
| 6,471,656 B1 | 10/2002 | Shalman et al. |
| 6,485,413 B1 | 11/2002 | Boppart et al. |
| 6,485,482 B1 | 11/2002 | Belef |
| 6,520,959 B1 | 2/2003 | Iwahashi et al. |
| 6,530,921 B1 | 3/2003 | Maki |
| 6,547,757 B1 | 4/2003 | Kranz et al. |
| 6,549,687 B1 | 4/2003 | Kochergin et al. |
| 6,552,796 B2 | 4/2003 | Magnin et al. |
| 6,564,087 B1 | 5/2003 | Pitris et al. |
| 6,565,514 B2 | 5/2003 | Svanerudh et al. |
| 6,570,659 B2 | 5/2003 | Schmitt |
| 6,570,893 B1 | 5/2003 | Libatique et al. |
| 6,572,553 B2 | 6/2003 | Crowley |
| 6,577,391 B1 | 6/2003 | Faupel et al. |
| 6,579,286 B1 | 6/2003 | Maki et al. |
| 6,589,233 B1 | 7/2003 | Maki |
| 6,601,459 B1 | 8/2003 | Jenni |
| 6,607,526 B1 | 8/2003 | Maki |
| 6,615,072 B1 | 9/2003 | Izatt et al. |
| 6,654,630 B2 | 11/2003 | Zuluaga et al. |
| 6,658,278 B2 | 12/2003 | Gruhl |
| 6,758,818 B2 | 7/2004 | Pantages et al. |
| 6,879,851 B2 | 4/2005 | McNamara et al. |
| 6,881,194 B2 | 4/2005 | Miyata et al. |
| 6,891,984 B2 | 5/2005 | Petersen et al. |
| 6,904,197 B2 | 6/2005 | Bhagavatula et al. |
| 6,904,199 B2 | 6/2005 | Zuluaga |
| 6,916,286 B2 | 7/2005 | Kazakevich |
| 6,925,320 B2 | 8/2005 | Gruhl |
| 6,940,885 B1 | 9/2005 | Cheng et al. |
| 7,003,184 B2 | 2/2006 | Ronnekleiv et al. |
| 7,016,024 B2 | 3/2006 | Bridge et al. |
| 7,022,118 B2 | 4/2006 | Ariura et al. |
| 7,024,025 B2 | 4/2006 | Sathyanarayana |
| 7,029,436 B2 | 4/2006 | Iizuka et al. |
| 7,099,358 B1 | 8/2006 | Chong |
| 7,134,994 B2 | 11/2006 | Alpert et al. |
| 7,155,272 B2 | 12/2006 | Yamaguchi et al. |
| 7,167,300 B2 | 1/2007 | Fermann et al. |
| 7,180,600 B2 | 2/2007 | Horii et al. |
| 7,231,243 B2 | 6/2007 | Tearney et al. |
| 7,241,286 B2 | 7/2007 | Atlas |
| 7,365,859 B2 | 4/2008 | Yun et al. |
| 7,366,376 B2 | 4/2008 | Shishkov et al. |
| 7,382,949 B2 | 6/2008 | Bouma et al. |
| 7,450,980 B2 | 11/2008 | Kawanishi |
| 7,551,293 B2 | 6/2009 | Yelin et al. |
| 7,567,349 B2 | 7/2009 | Tearney et al. |
| 7,625,366 B2 | 12/2009 | Atlas |
| 7,682,089 B2 | 3/2010 | Rohlen |
| 7,691,061 B2 | 4/2010 | Hirota |

(56) References Cited

U.S. PATENT DOCUMENTS

| | | |
|---|---|---|
| 7,711,413 B2 | 5/2010 | Feldman et al. |
| 7,724,786 B2 | 5/2010 | Bouma et al. |
| 7,733,497 B2 | 6/2010 | Yun et al. |
| 7,738,941 B2 | 6/2010 | Hirota |
| 7,740,408 B2 | 6/2010 | Irisawa |
| 7,742,173 B2 | 6/2010 | Yun et al. |
| 7,761,139 B2 | 7/2010 | Tearney et al. |
| 7,783,337 B2 | 8/2010 | Feldman et al. |
| 7,794,230 B2 | 9/2010 | Lakin et al. |
| 7,803,141 B2 | 9/2010 | Epstein et al. |
| 7,812,961 B2 | 10/2010 | Yamaguchi |
| 7,813,609 B2 | 10/2010 | Petersen et al. |
| 7,815,632 B2 | 10/2010 | Hayakawa et al. |
| 7,843,572 B2 | 11/2010 | Tearney et al. |
| 7,847,949 B2 | 12/2010 | Tearney et al. |
| 7,848,791 B2 | 12/2010 | Schmitt et al. |
| 7,872,759 B2 | 1/2011 | Tearney et al. |
| 7,905,838 B2 | 3/2011 | Hirota |
| 7,911,621 B2 | 3/2011 | Motaghiannezam et al. |
| 7,916,387 B2 | 3/2011 | Schmitt |
| 7,920,271 B2 | 4/2011 | Vakoc et al. |
| 7,922,650 B2 | 4/2011 | McWeeney et al. |
| 7,926,562 B2 | 4/2011 | Poitzsch et al. |
| 7,935,060 B2 | 5/2011 | Schmitt et al. |
| 7,940,397 B2 | 5/2011 | Masuda |
| 7,952,718 B2 | 5/2011 | Li et al. |
| 7,969,578 B2 | 6/2011 | Yun et al. |
| 7,982,879 B2 | 7/2011 | Desjardins et al. |
| 8,018,598 B2 | 9/2011 | Cense et al. |
| 8,029,446 B2 | 10/2011 | Horiike et al. |
| 8,029,447 B2 | 10/2011 | Kanz et al. |
| 8,032,200 B2 | 10/2011 | Tearney et al. |
| 8,040,524 B2 | 10/2011 | Ozawa |
| 8,047,996 B2 | 11/2011 | Goodnow et al. |
| 8,049,900 B2 | 11/2011 | Kemp et al. |
| 8,052,605 B2 | 11/2011 | Muller et al. |
| 8,055,107 B2 | 11/2011 | Masuda |
| 8,081,316 B2 | 12/2011 | De Boer et al. |
| 8,094,319 B2 | 1/2012 | Onimura |
| 8,100,833 B2 | 1/2012 | Hirota |
| 8,108,032 B2 | 1/2012 | Onimura et al. |
| 8,116,605 B2 | 2/2012 | Petersen et al. |
| 8,125,648 B2 | 2/2012 | Milner et al. |
| 8,149,418 B2 | 4/2012 | Tearney et al. |
| 8,157,741 B2 | 4/2012 | Hirota |
| 8,157,742 B2 | 4/2012 | Taylor |
| 8,174,702 B2 | 5/2012 | Tearney et al. |
| 8,206,372 B2 | 6/2012 | Larson et al. |
| 8,206,377 B2 | 6/2012 | Petroff |
| 8,208,995 B2 | 6/2012 | Tearney et al. |
| 8,231,516 B2 | 7/2012 | Maschke |
| 8,241,196 B2 | 8/2012 | Scibona |
| 8,289,522 B2 | 10/2012 | Tearney et al. |
| RE43,875 E | 12/2012 | Shishkov et al. |
| 8,322,932 B2 | 12/2012 | Irisawa |
| 8,325,419 B2 | 12/2012 | Schmitt |
| 8,337,379 B2 | 12/2012 | Fletcher et al. |
| 8,339,592 B2 | 12/2012 | Hlavinka et al. |
| 8,346,348 B2 | 1/2013 | Onimura |
| 8,351,665 B2 | 1/2013 | Tearney et al. |
| 8,355,138 B2 | 1/2013 | Yun et al. |
| 8,384,907 B2 | 2/2013 | Tearney et al. |
| 8,384,909 B2 | 2/2013 | Yun et al. |
| 8,412,312 B2 | 4/2013 | Judell et al. |
| 8,414,496 B2 | 4/2013 | Goodnow et al. |
| 8,449,439 B2 | 5/2013 | Fletcher et al. |
| 8,449,468 B2 | 5/2013 | Petersen et al. |
| 8,452,371 B2 | 5/2013 | Feldman et al. |
| 8,473,037 B2 | 6/2013 | Irisawa |
| 8,473,073 B2 | 6/2013 | Vardiman |
| 8,478,384 B2 | 7/2013 | Schmitt et al. |
| 8,478,387 B2 | 7/2013 | Xu |
| 8,493,567 B2 | 7/2013 | Inoue |
| 8,501,015 B2 | 8/2013 | Fletcher et al. |
| 8,503,844 B2 | 8/2013 | Petersen et al. |
| 8,531,676 B2 | 9/2013 | Condit et al. |
| 8,535,210 B2 | 9/2013 | Kolenbrander et al. |
| 8,556,820 B2 | 10/2013 | Alpert et al. |
| 8,559,012 B2 | 10/2013 | Tearney et al. |
| 8,581,643 B1 | 11/2013 | Schmitt |
| 8,582,109 B1 | 11/2013 | Schmitt |
| 8,582,619 B2 | 11/2013 | Adler |
| 8,582,934 B2 | 11/2013 | Adler et al. |
| 8,585,592 B2 | 11/2013 | Luevano et al. |
| 8,593,619 B2 | 11/2013 | Colice et al. |
| 8,593,641 B2 | 11/2013 | Kemp et al. |
| 8,618,032 B2 | 12/2013 | Kurita |
| 8,626,453 B2 | 1/2014 | Myoujou et al. |
| 8,636,659 B2 | 1/2014 | Alpert et al. |
| 8,676,013 B2 | 3/2014 | Bouma et al. |
| 8,676,299 B2 | 3/2014 | Schmitt et al. |
| 8,687,201 B2 | 4/2014 | Adler |
| 8,705,046 B2 | 4/2014 | Yun et al. |
| 8,712,506 B2 | 4/2014 | Courtney et al. |
| 8,753,281 B2 | 6/2014 | Schmitt et al. |
| 8,760,663 B2 | 6/2014 | Tearney et al. |
| 8,761,469 B2 | 6/2014 | Kemp et al. |
| 8,786,336 B1 | 7/2014 | Schmitt |
| 8,804,126 B2 | 8/2014 | Tearney et al. |
| 8,808,186 B2 | 8/2014 | Fruland et al. |
| 8,810,901 B2 | 8/2014 | Huber et al. |
| 8,825,142 B2 | 9/2014 | Suehara |
| 8,827,926 B2 | 9/2014 | Kinoshita et al. |
| 8,831,321 B1 | 9/2014 | Elbasiony |
| 8,868,159 B2 | 10/2014 | Onimura |
| 8,885,171 B2 | 11/2014 | Watanabe et al. |
| 8,896,838 B2 | 11/2014 | Tearney et al. |
| 8,902,941 B2 | 12/2014 | Schmitt |
| 8,909,324 B2 | 12/2014 | Furuichi |
| 8,911,357 B2 | 12/2014 | Omori |
| 8,926,590 B2 | 1/2015 | Petroff |
| 8,928,889 B2 | 1/2015 | Tearney et al. |
| 8,945,526 B2 | 2/2015 | Akitsu et al. |
| 8,948,228 B2 | 2/2015 | Adler |
| 8,948,613 B2 | 2/2015 | Schmitt et al. |
| 8,953,911 B1 | 2/2015 | Xu et al. |
| 8,983,582 B2 | 3/2015 | Webler |
| 8,989,849 B2 | 3/2015 | Milner et al. |
| 8,994,803 B2 | 3/2015 | Kaneko |
| 8,996,099 B2 | 3/2015 | Feldman et al. |
| 8,998,797 B2 | 4/2015 | Omori |
| 9,007,696 B2 | 4/2015 | Petersen et al. |
| 9,033,890 B2 | 5/2015 | Furuichi |
| 9,036,966 B2 | 5/2015 | Bhagavatula et al. |
| 9,039,626 B2 | 5/2015 | Courtney |
| 9,060,689 B2 | 6/2015 | Tearney et al. |
| 9,069,396 B2 | 6/2015 | Adler et al. |
| 9,076,202 B2 | 7/2015 | Courtney et al. |
| 9,081,148 B2 | 7/2015 | Tearney et al. |
| 9,084,532 B2 | 7/2015 | Horiike |
| 9,087,368 B2 | 7/2015 | Tearney et al. |
| 9,091,524 B2 | 7/2015 | Adler et al. |
| 9,101,298 B2 | 8/2015 | Hossack et al. |
| 9,107,682 B2 | 8/2015 | Scheller et al. |
| 9,107,687 B2 | 8/2015 | Kinoshita et al. |
| 9,121,926 B2 | 9/2015 | Nair et al. |
| 9,131,850 B2 | 9/2015 | Liu et al. |
| 9,138,147 B2 | 9/2015 | Schmitt et al. |
| 9,164,240 B2 | 10/2015 | Schmitt et al. |
| 9,168,003 B2 | 10/2015 | Suzuki et al. |
| 9,173,572 B2 | 11/2015 | Colice et al. |
| 9,173,591 B2 | 11/2015 | Elbasiony et al. |
| 9,194,690 B2 | 11/2015 | Bhagavatula et al. |
| 9,207,064 B2 | 12/2015 | Inoue |
| 9,226,660 B2 | 1/2016 | De Boer et al. |
| 9,226,665 B2 | 1/2016 | Tearney et al. |
| 9,254,102 B2 | 2/2016 | Tearney et al. |
| 9,289,127 B2 | 3/2016 | Mitsuhashi et al. |
| 9,289,582 B2 | 3/2016 | Suehara |
| 9,295,450 B2 | 3/2016 | Furuichi et al. |
| 9,295,455 B2 | 3/2016 | Karino et al. |
| 9,301,687 B2 | 4/2016 | Kemp |
| 9,304,121 B2 | 4/2016 | Tearney et al. |
| 9,322,639 B2 | 4/2016 | Watanabe et al. |

(56) References Cited

U.S. PATENT DOCUMENTS

| | | |
|---|---|---|
| 9,326,789 B2 | 5/2016 | Fruland et al. |
| 9,330,092 B2 | 5/2016 | Vakoc et al. |
| 9,339,173 B2 | 5/2016 | McWeeney et al. |
| 9,339,348 B2 | 5/2016 | Davies et al. |
| 9,345,864 B2 | 5/2016 | Suehara |
| 9,347,765 B2 | 5/2016 | Kemp et al. |
| 9,351,698 B2 | 5/2016 | Dascal et al. |
| 9,357,923 B2 | 6/2016 | Courtney et al. |
| 9,375,148 B2 | 6/2016 | Senoo |
| 9,375,158 B2 | 6/2016 | Vakoc et al. |
| 9,375,164 B2 | 6/2016 | Tolkowsky et al. |
| 9,377,290 B2 | 6/2016 | Yun et al. |
| 9,404,731 B2 | 8/2016 | Adler et al. |
| 9,408,539 B2 | 8/2016 | Tearney et al. |
| 9,417,052 B2 | 8/2016 | Adler |
| 9,435,736 B2 | 9/2016 | Kolenbrander et al. |
| 9,435,956 B1 | 9/2016 | Xu et al. |
| 9,439,570 B2 | 9/2016 | Vertikov |
| 9,441,948 B2 | 9/2016 | Vakoc et al. |
| 9,462,950 B2 | 10/2016 | Xu |
| 9,464,883 B2 | 10/2016 | Swanson et al. |
| 9,488,464 B1 | 11/2016 | Schmitt |
| 9,507,074 B2 | 11/2016 | Zhu et al. |
| 9,513,276 B2 | 12/2016 | Tearney et al. |
| 9,526,424 B2 | 12/2016 | Judell et al. |
| 9,566,752 B2 | 2/2017 | Hartkorn |
| 9,572,495 B2 | 2/2017 | Schmitt et al. |
| 9,572,496 B2 | 2/2017 | Furuichi et al. |
| 9,574,870 B2 | 2/2017 | Yamazaki et al. |
| 9,591,967 B2 | 3/2017 | Nishiyama et al. |
| 9,605,942 B2 | 3/2017 | Staloff |
| 9,610,064 B2 | 4/2017 | Adler et al. |
| 9,615,771 B2 | 4/2017 | Furuichi et al. |
| 9,622,706 B2 | 4/2017 | Dick et al. |
| 9,638,862 B2 | 5/2017 | Bhagavatula et al. |
| 9,642,531 B2 | 5/2017 | Tearney et al. |
| 9,645,322 B2 | 5/2017 | Murashima et al. |
| 9,646,377 B2 | 5/2017 | Tearney et al. |
| 9,659,375 B2 | 5/2017 | Zagrodsky et al. |
| 9,702,687 B2 | 7/2017 | Schmitt |
| 9,702,762 B2 | 7/2017 | Friedman et al. |
| 9,704,240 B2 | 7/2017 | Lam et al. |
| 9,710,891 B2 | 7/2017 | Sakamoto |
| 9,730,613 B2 | 8/2017 | Stigall et al. |
| 9,763,623 B2 | 9/2017 | Tearney et al. |
| 9,778,020 B2 | 10/2017 | Tumlinson et al. |
| 9,788,790 B2 | 10/2017 | Black et al. |
| 9,808,303 B2 | 11/2017 | Ryba et al. |
| 9,812,846 B2 | 11/2017 | Yun et al. |
| 9,833,221 B2 | 12/2017 | Hutchins et al. |
| 9,836,835 B2 | 12/2017 | Furuichi et al. |
| 9,843,159 B2 | 12/2017 | Cable et al. |
| 9,855,020 B2 | 1/2018 | Nair et al. |
| 9,858,387 B2 | 1/2018 | Lavi et al. |
| 9,864,140 B2 | 1/2018 | Adler et al. |
| 9,872,665 B2 | 1/2018 | Okubo et al. |
| 9,891,044 B2 | 2/2018 | Tu et al. |
| 9,897,538 B2 | 2/2018 | Tearney et al. |
| 9,907,527 B2 | 3/2018 | Dascal et al. |
| 9,933,244 B2 | 4/2018 | Krol et al. |
| 9,940,723 B2 | 4/2018 | Gopinath et al. |
| 9,943,233 B2 | 4/2018 | Lavi et al. |
| 9,962,127 B2 | 5/2018 | Wang et al. |
| 9,980,648 B2 | 5/2018 | Itoh et al. |
| 9,983,356 B2 | 5/2018 | Schmitt et al. |
| 9,986,938 B2 | 6/2018 | Tu et al. |
| 9,989,945 B2 | 6/2018 | Adler et al. |
| 9,996,921 B2 | 6/2018 | Ambwani et al. |
| 10,004,400 B2 | 6/2018 | Nakamoto et al. |
| 10,004,863 B2 | 6/2018 | Vazales et al. |
| 10,006,753 B2 | 6/2018 | Schmitt et al. |
| 10,028,725 B2 | 7/2018 | Petroff |
| 10,089,755 B2 | 10/2018 | Griffin et al. |
| 10,092,188 B2 | 10/2018 | Jaffer et al. |
| 10,109,058 B2 | 10/2018 | Ambwani et al. |
| 10,124,153 B2 | 11/2018 | Feig et al. |
| 10,140,712 B2 | 11/2018 | Ambwani |
| 10,162,114 B2 | 12/2018 | Bhagavatula et al. |
| 10,172,582 B2 | 1/2019 | Dascal et al. |
| 10,186,056 B2 | 1/2019 | Senzig et al. |
| 10,207,124 B2 | 2/2019 | Shimizu et al. |
| 10,213,109 B2 | 2/2019 | Itoh et al. |
| 10,213,186 B2 | 2/2019 | Inoue et al. |
| 10,219,780 B2 | 3/2019 | Castella et al. |
| 10,222,956 B2 | 3/2019 | Gopinath et al. |
| 10,238,349 B2 | 3/2019 | Furuichi et al. |
| 10,238,816 B2 | 3/2019 | Matsubara et al. |
| 10,261,223 B2 | 4/2019 | Tearney et al. |
| 10,271,818 B2 | 4/2019 | Kobayashi |
| 10,285,568 B2 | 5/2019 | Tearney et al. |
| 10,327,726 B2 | 6/2019 | Dascal et al. |
| 10,331,099 B2 | 6/2019 | Adler et al. |
| 10,335,039 B2 | 7/2019 | Xu |
| 10,338,795 B2 | 7/2019 | Gopinath et al. |
| 10,342,502 B2 | 7/2019 | Dascal et al. |
| 10,387,013 B2 | 8/2019 | Jamello |
| 10,453,190 B2 | 10/2019 | Griffin |
| 10,453,191 B2 | 10/2019 | Shalev et al. |
| 10,453,196 B2 | 10/2019 | Ambwani |
| 10,463,254 B2 | 11/2019 | Tearney et al. |
| 10,499,813 B2 | 12/2019 | Adler |
| 10,529,093 B2 | 1/2020 | Griffin et al. |
| 10,551,251 B2 | 2/2020 | Friedman et al. |
| 10,593,037 B2 | 3/2020 | Gopinath |
| 10,631,718 B2 | 4/2020 | Petroff et al. |
| 10,631,754 B2 | 4/2020 | Gopinath |
| 10,646,198 B2 | 5/2020 | Peterson et al. |
| 10,648,918 B2 | 5/2020 | Schmitt |
| 10,687,777 B2 | 6/2020 | Dascal et al. |
| 10,713,786 B2 | 7/2020 | Ambwani et al. |
| 10,729,376 B2 | 8/2020 | Courtney |
| 10,792,012 B2 | 10/2020 | Hutchins et al. |
| 10,806,421 B2 | 10/2020 | Keller |
| 10,878,572 B2 | 12/2020 | Gopinath et al. |
| 10,902,599 B2 | 1/2021 | Ambwani et al. |
| 11,058,385 B2 | 7/2021 | Kunio |
| 11,064,873 B2 | 7/2021 | Petroff et al. |
| 11,278,206 B2 | 3/2022 | Petroff et al. |
| 11,583,172 B2 | 2/2023 | Petroff et al. |
| 11,684,242 B2 | 6/2023 | Petroff et al. |
| 2002/0041724 A1 | 4/2002 | Ronnekleiv et al. |
| 2002/0045811 A1 | 4/2002 | Kittrell et al. |
| 2002/0072880 A1 | 6/2002 | Svanerudh et al. |
| 2002/0099289 A1 | 7/2002 | Crowley |
| 2002/0131049 A1 | 9/2002 | Schmitt |
| 2002/0151799 A1 | 10/2002 | Pantages et al. |
| 2002/0151823 A1 | 10/2002 | Miyata et al. |
| 2002/0163622 A1 | 11/2002 | Magnin et al. |
| 2002/0183601 A1 | 12/2002 | Tearney et al. |
| 2002/0183622 A1 | 12/2002 | Zuluaga et al. |
| 2002/0188204 A1 | 12/2002 | McNamara et al. |
| 2002/0198457 A1 | 12/2002 | Tearney et al. |
| 2003/0004417 A1 | 1/2003 | Ariura et al. |
| 2003/0013952 A1 | 1/2003 | Iizuka et al. |
| 2003/0032863 A1 | 2/2003 | Kazakevich |
| 2003/0073909 A1 | 4/2003 | Gruhl |
| 2003/0081875 A1 | 5/2003 | Kochergin et al. |
| 2003/0147551 A1 | 8/2003 | Sathyanarayana |
| 2003/0165291 A1 | 9/2003 | Bhagavatula et al. |
| 2003/0216621 A1 | 11/2003 | Alpert et al. |
| 2004/0017961 A1 | 1/2004 | Petersen et al. |
| 2004/0034290 A1 | 2/2004 | Zuluaga |
| 2004/0082861 A1 | 4/2004 | Gruhl |
| 2004/0092913 A1 | 5/2004 | Hennings et al. |
| 2004/0215166 A1 | 10/2004 | Atlas |
| 2005/0004453 A1 | 1/2005 | Tearney et al. |
| 2005/0038406 A1 | 2/2005 | Epstein et al. |
| 2005/0101870 A1 | 5/2005 | Yamaguchi et al. |
| 2005/0128488 A1 | 6/2005 | Yelin et al. |
| 2005/0163426 A1 | 7/2005 | Fermann et al. |
| 2005/0168751 A1 | 8/2005 | Horii et al. |
| 2005/0187422 A1 | 8/2005 | Maschke |
| 2005/0201662 A1* | 9/2005 | Petersen ............ G01B 9/0205 385/12 |

(56) References Cited

U.S. PATENT DOCUMENTS

| | | |
|---|---|---|
| 2005/0221277 A1 | 10/2005 | Kawanishi |
| 2005/0259242 A1 | 11/2005 | Bridge et al. |
| 2005/0272975 A1 | 12/2005 | McWeeney et al. |
| 2005/0288583 A1 | 12/2005 | Hirota |
| 2006/0039004 A1 | 2/2006 | De Boer et al. |
| 2006/0055936 A1 | 3/2006 | Yun et al. |
| 2006/0058622 A1 | 3/2006 | Tearney et al. |
| 2006/0067620 A1 | 3/2006 | Shishkov et al. |
| 2006/0091566 A1 | 5/2006 | Yang et al. |
| 2006/0093276 A1 | 5/2006 | Bouma et al. |
| 2006/0095065 A1 | 5/2006 | Tanimura et al. |
| 2006/0135870 A1 | 6/2006 | Webler |
| 2006/0166176 A1 | 7/2006 | Lakin et al. |
| 2006/0227333 A1 | 10/2006 | Tearney et al. |
| 2006/0241484 A1 | 10/2006 | Horiike et al. |
| 2006/0241493 A1 | 10/2006 | Feldman et al. |
| 2006/0241503 A1 | 10/2006 | Schmitt et al. |
| 2006/0244973 A1 | 11/2006 | Yun et al. |
| 2006/0247743 A1 | 11/2006 | Hayakawa et al. |
| 2006/0279742 A1 | 12/2006 | Tearney et al. |
| 2007/0012886 A1 | 1/2007 | Tearney et al. |
| 2007/0015969 A1 | 1/2007 | Feldman et al. |
| 2007/0035743 A1 | 2/2007 | Vakoc et al. |
| 2007/0038040 A1 | 2/2007 | Cense et al. |
| 2007/0038274 A1 | 2/2007 | Ishii et al. |
| 2007/0060822 A1 | 3/2007 | Alpert et al. |
| 2007/0073162 A1 | 3/2007 | Tearney et al. |
| 2007/0081236 A1 | 4/2007 | Tearney et al. |
| 2007/0106155 A1 | 5/2007 | Goodnow et al. |
| 2007/0121196 A1 | 5/2007 | Tearney et al. |
| 2007/0201033 A1 | 8/2007 | Desjardins et al. |
| 2007/0229801 A1 | 10/2007 | Tearney et al. |
| 2007/0232890 A1 | 10/2007 | Hirota |
| 2007/0232891 A1 | 10/2007 | Hirota |
| 2007/0232892 A1 | 10/2007 | Hirota |
| 2007/0232893 A1 | 10/2007 | Tanioka |
| 2007/0233396 A1 | 10/2007 | Tearney et al. |
| 2007/0236700 A1 | 10/2007 | Yun et al. |
| 2007/0244391 A1 | 10/2007 | Hirota |
| 2007/0260198 A1 | 11/2007 | Atlas |
| 2007/0268456 A1 | 11/2007 | Ohbayshi et al. |
| 2008/0002211 A1 | 1/2008 | Park et al. |
| 2008/0004530 A1 | 1/2008 | Feldman et al. |
| 2008/0007734 A1 | 1/2008 | Park et al. |
| 2008/0019908 A1 | 1/2008 | Akitsu et al. |
| 2008/0021275 A1 | 1/2008 | Tearney et al. |
| 2008/0045394 A1 | 2/2008 | Fletcher et al. |
| 2008/0049232 A1 | 2/2008 | Vakoc et al. |
| 2008/0161696 A1 | 7/2008 | Schmitt et al. |
| 2008/0165366 A1 | 7/2008 | Schmitt |
| 2008/0177139 A1 | 7/2008 | Courtney et al. |
| 2008/0181263 A1 | 7/2008 | Bouma et al. |
| 2008/0208227 A1 | 8/2008 | Kadykowski et al. |
| 2008/0225301 A1 | 9/2008 | Yamaguchi |
| 2008/0262346 A1 | 10/2008 | Assis et al. |
| 2008/0269572 A1 | 10/2008 | Kanz et al. |
| 2008/0291463 A1 | 11/2008 | Milner et al. |
| 2008/0297806 A1 | 12/2008 | Motaghiannezam et al. |
| 2009/0018393 A1 | 1/2009 | Dick et al. |
| 2009/0027689 A1 | 1/2009 | Yun et al. |
| 2009/0036782 A1 | 2/2009 | Vakoc et al. |
| 2009/0043191 A1 | 2/2009 | Castella et al. |
| 2009/0046295 A1 | 2/2009 | Kemp et al. |
| 2009/0046980 A1 | 2/2009 | Rohlen |
| 2009/0073454 A1 | 3/2009 | Ozawa |
| 2009/0073455 A1 | 3/2009 | Onimura |
| 2009/0093980 A1 | 4/2009 | Kemp et al. |
| 2009/0122320 A1 | 5/2009 | Petersen et al. |
| 2009/0131801 A1 | 5/2009 | Suter et al. |
| 2009/0135429 A1 | 5/2009 | Masuda |
| 2009/0143686 A1 | 6/2009 | Onimura et al. |
| 2009/0182246 A1 | 7/2009 | Kinoshita et al. |
| 2009/0192519 A1 | 7/2009 | Omori |
| 2009/0196477 A1 | 8/2009 | Cense et al. |
| 2009/0196554 A1 | 8/2009 | Irisawa |
| 2009/0251704 A1 | 10/2009 | Masuda |
| 2009/0261240 A1 | 10/2009 | Watanabe et al. |
| 2009/0262361 A1 | 10/2009 | Tanioka et al. |
| 2009/0283258 A1 | 11/2009 | Poitzsch et al. |
| 2009/0299195 A1 | 12/2009 | Muller et al. |
| 2009/0306520 A1 | 12/2009 | Schmitt et al. |
| 2009/0323076 A1 | 12/2009 | Li et al. |
| 2010/0019189 A1 | 1/2010 | Kurita |
| 2010/0042084 A1 | 2/2010 | Nariyuki et al. |
| 2010/0073682 A1 | 3/2010 | Inoue |
| 2010/0076320 A1 | 3/2010 | Petersen et al. |
| 2010/0094127 A1 | 4/2010 | Xu |
| 2010/0110414 A1 | 5/2010 | Colice et al. |
| 2010/0130872 A1 | 5/2010 | Irisawa |
| 2010/0157309 A1 | 6/2010 | Tearney et al. |
| 2010/0158339 A1 | 6/2010 | Omori |
| 2010/0160134 A1 | 6/2010 | Scibona |
| 2010/0160780 A1 | 6/2010 | Swan et al. |
| 2010/0168587 A1 | 7/2010 | Feldman et al. |
| 2010/0220334 A1 | 9/2010 | Condit et al. |
| 2010/0241154 A1 | 9/2010 | Larson et al. |
| 2010/0249588 A1 | 9/2010 | Knight |
| 2010/0249601 A1 | 9/2010 | Courtney |
| 2010/0253949 A1 | 10/2010 | Adler et al. |
| 2010/0298908 A1 | 11/2010 | Vardiman |
| 2010/0305452 A1 | 12/2010 | Black et al. |
| 2010/0309477 A1 | 12/2010 | Yun et al. |
| 2011/0007315 A1 | 1/2011 | Petersen et al. |
| 2011/0009741 A1* | 1/2011 | Matthews ............ A61B 5/0084 600/425 |
| 2011/0019182 A1 | 1/2011 | Hlavinka et al. |
| 2011/0058178 A1 | 3/2011 | Tearney et al. |
| 2011/0071404 A1 | 3/2011 | Schmitt et al. |
| 2011/0071405 A1 | 3/2011 | Judell et al. |
| 2011/0092823 A1 | 4/2011 | Tearney et al. |
| 2011/0101207 A1 | 5/2011 | Schmitt |
| 2011/0143905 A1 | 6/2011 | Kolenbrander et al. |
| 2011/0144504 A1 | 6/2011 | Tearney et al. |
| 2011/0149296 A1 | 6/2011 | Tearney et al. |
| 2011/0151980 A1 | 6/2011 | Petroff |
| 2011/0152771 A1 | 6/2011 | Milner et al. |
| 2011/0157686 A1 | 6/2011 | Huber et al. |
| 2011/0172511 A1 | 7/2011 | Petersen et al. |
| 2011/0178398 A1 | 7/2011 | Tearney et al. |
| 2011/0178413 A1 | 7/2011 | Schmitt et al. |
| 2011/0190586 A1 | 8/2011 | Kemp |
| 2011/0196217 A1 | 8/2011 | Myoujou et al. |
| 2011/0201924 A1 | 8/2011 | Tearney et al. |
| 2011/0216325 A1 | 9/2011 | Schmitt |
| 2011/0218403 A1 | 9/2011 | Tearney et al. |
| 2011/0224541 A1 | 9/2011 | Yun et al. |
| 2011/0228280 A1 | 9/2011 | Schmitt et al. |
| 2011/0237958 A1 | 9/2011 | Onimura |
| 2011/0245683 A1 | 10/2011 | Onimura |
| 2011/0245684 A1 | 10/2011 | Onimura |
| 2011/0261366 A1 | 10/2011 | Tearney et al. |
| 2011/0267340 A1 | 11/2011 | Kraus et al. |
| 2011/0270091 A1 | 11/2011 | Hossack et al. |
| 2011/0292400 A1 | 12/2011 | Fleming et al. |
| 2011/0299091 A1 | 12/2011 | Yun et al. |
| 2012/0002928 A1 | 1/2012 | Irisawa |
| 2012/0004506 A1 | 1/2012 | Tearney et al. |
| 2012/0007974 A1 | 1/2012 | Kaneko |
| 2012/0008146 A1 | 1/2012 | Tearney et al. |
| 2012/0013914 A1 | 1/2012 | Kemp et al. |
| 2012/0022360 A1* | 1/2012 | Kemp ................. A61B 5/1459 600/407 |
| 2012/0035454 A1 | 2/2012 | Tearney et al. |
| 2012/0053918 A1 | 3/2012 | Taylor |
| 2012/0057157 A1 | 3/2012 | Petersen et al. |
| 2012/0063570 A1 | 3/2012 | Furuichi et al. |
| 2012/0065517 A1 | 3/2012 | Goodnow et al. |
| 2012/0071736 A1 | 3/2012 | Luevano et al. |
| 2012/0123352 A1 | 5/2012 | Fruland et al. |
| 2012/0127476 A1 | 5/2012 | De Boer et al. |
| 2012/0135384 A1 | 5/2012 | Nakao |
| 2012/0170848 A1 | 7/2012 | Kemp et al. |
| 2012/0190974 A1 | 7/2012 | Suehara |
| 2012/0215091 A1 | 8/2012 | Suzuki et al. |

(56) References Cited

U.S. PATENT DOCUMENTS

| | | |
|---|---|---|
| 2012/0220836 A1 | 8/2012 | Alpert et al. |
| 2012/0226151 A1 | 9/2012 | Irisawa |
| 2012/0236883 A1 | 9/2012 | Adler |
| 2012/0238869 A1 | 9/2012 | Schmitt et al. |
| 2012/0243761 A1 | 9/2012 | Senzig et al. |
| 2012/0245459 A1 | 9/2012 | Senoo |
| 2012/0250028 A1 | 10/2012 | Schmitt et al. |
| 2012/0253114 A1 | 10/2012 | Kinoshita et al. |
| 2012/0253123 A1 | 10/2012 | Shimizu et al. |
| 2012/0253184 A1 | 10/2012 | Furuichi et al. |
| 2012/0253185 A1 | 10/2012 | Furuichi |
| 2012/0281237 A1 | 11/2012 | Tearney et al. |
| 2012/0310081 A1 | 12/2012 | Adler et al. |
| 2012/0330101 A1 | 12/2012 | Brennan et al. |
| 2013/0002843 A1 | 1/2013 | Horiike |
| 2013/0006104 A1 | 1/2013 | Mitsuhashi et al. |
| 2013/0006105 A1 | 1/2013 | Furuichi |
| 2013/0010303 A1 | 1/2013 | Petersen et al. |
| 2013/0012810 A1 | 1/2013 | Nakamoto et al. |
| 2013/0012811 A1 | 1/2013 | Schmitt et al. |
| 2013/0023760 A1 | 1/2013 | Liu et al. |
| 2013/0023761 A1 | 1/2013 | Petroff |
| 2013/0046190 A1 | 2/2013 | Davies et al. |
| 2013/0051728 A1 | 2/2013 | Petroff et al. |
| 2013/0072367 A1 | 3/2013 | Fletcher et al. |
| 2013/0072805 A1 | 3/2013 | Schmitt et al. |
| 2013/0079630 A1 | 3/2013 | Horiike |
| 2013/0079631 A1 | 3/2013 | Horiike et al. |
| 2013/0100455 A1 | 4/2013 | Tearney et al. |
| 2013/0107043 A1 | 5/2013 | Fletcher et al. |
| 2013/0116671 A1 | 5/2013 | Scheller et al. |
| 2013/0128274 A1 | 5/2013 | Yun et al. |
| 2013/0148106 A1 | 6/2013 | Tearney et al. |
| 2013/0176571 A1 | 7/2013 | Tearney et al. |
| 2013/0185023 A1 | 7/2013 | Vakoc et al. |
| 2013/0188850 A1 | 7/2013 | Tearney et al. |
| 2013/0215427 A1 | 8/2013 | Bouma et al. |
| 2013/0216114 A1 | 8/2013 | Courtney et al. |
| 2013/0217964 A1 | 8/2013 | Kumoyama et al. |
| 2013/0222813 A1 | 8/2013 | Watanabe et al. |
| 2013/0246034 A1 | 9/2013 | Sharma et al. |
| 2013/0266259 A1 | 10/2013 | Bhagavatula et al. |
| 2013/0278936 A1 | 10/2013 | Inoue |
| 2013/0281844 A1 | 10/2013 | Karino et al. |
| 2013/0303907 A1 | 11/2013 | Corl |
| 2013/0310698 A1 | 11/2013 | Judell et al. |
| 2013/0314716 A1 | 11/2013 | Tearney et al. |
| 2013/0331689 A1 | 12/2013 | Le et al. |
| 2014/0005023 A1 | 1/2014 | Kolenbrander et al. |
| 2014/0018669 A1 | 1/2014 | Xu |
| 2014/0024930 A1 | 1/2014 | Furuichi et al. |
| 2014/0024931 A1 | 1/2014 | Winston et al. |
| 2014/0031677 A1 | 1/2014 | Iftimia et al. |
| 2014/0031679 A1 | 1/2014 | Tashiro et al. |
| 2014/0036941 A1 | 2/2014 | Adler |
| 2014/0063488 A1 | 3/2014 | Adler |
| 2014/0066706 A1 | 3/2014 | McWeeney et al. |
| 2014/0066756 A1 | 3/2014 | Sinclair et al. |
| 2014/0083970 A1 | 3/2014 | Kumar et al. |
| 2014/0088411 A1 | 3/2014 | Suehara et al. |
| 2014/0094697 A1* | 4/2014 | Petroff ................. A61B 5/0066 600/427 |
| 2014/0100451 A1 | 4/2014 | Tolkowsky et al. |
| 2014/0114182 A1 | 4/2014 | Petersen et al. |
| 2014/0142427 A1 | 5/2014 | Petroff |
| 2014/0142432 A1 | 5/2014 | Hutchins et al. |
| 2014/0142436 A1 | 5/2014 | Hutchins et al. |
| 2014/0150782 A1 | 6/2014 | Vazales et al. |
| 2014/0177935 A1 | 6/2014 | Nair et al. |
| 2014/0180071 A1 | 6/2014 | Stigall et al. |
| 2014/0180083 A1 | 6/2014 | Hoseit |
| 2014/0187929 A1 | 7/2014 | Schmitt et al. |
| 2014/0200867 A1 | 7/2014 | Lavi et al. |
| 2014/0206989 A1 | 7/2014 | Colice et al. |
| 2014/0207168 A1 | 7/2014 | Kawaura et al. |
| 2014/0218742 A1 | 8/2014 | Adler |
| 2014/0243876 A1 | 8/2014 | Suehara |
| 2014/0247454 A1 | 9/2014 | Bhagavatula et al. |
| 2014/0249407 A1 | 9/2014 | Adler et al. |
| 2014/0257087 A1 | 9/2014 | Elbasiony et al. |
| 2014/0267038 A1 | 9/2014 | Adler et al. |
| 2014/0268167 A1 | 9/2014 | Friedman et al. |
| 2014/0270436 A1 | 9/2014 | Dascal et al. |
| 2014/0270445 A1 | 9/2014 | Kemp |
| 2014/0276020 A1 | 9/2014 | Hutchins et al. |
| 2014/0276108 A1 | 9/2014 | Vertikov |
| 2014/0277072 A1 | 9/2014 | Suehara |
| 2014/0301620 A1 | 10/2014 | Tearney et al. |
| 2014/0323877 A1 | 10/2014 | Courtney et al. |
| 2014/0346693 A1 | 11/2014 | Hartkorn |
| 2014/0371598 A1 | 12/2014 | Okubo et al. |
| 2014/0376000 A1 | 12/2014 | Swanson et al. |
| 2014/0378845 A1 | 12/2014 | Nadkarni |
| 2014/0379269 A1 | 12/2014 | Schmitt |
| 2015/0005615 A1 | 1/2015 | Inoue et al. |
| 2015/0005626 A1 | 1/2015 | Kaneko |
| 2015/0005627 A1 | 1/2015 | Itoh et al. |
| 2015/0005628 A1 | 1/2015 | Itoh et al. |
| 2015/0025369 A1 | 1/2015 | Bhagavatula et al. |
| 2015/0029513 A1 | 1/2015 | Tearney et al. |
| 2015/0036146 A1 | 2/2015 | Staloff |
| 2015/0049339 A1 | 2/2015 | Tearney et al. |
| 2015/0051485 A1 | 2/2015 | Itoh et al. |
| 2015/0057958 A1 | 2/2015 | Watanabe et al. |
| 2015/0077755 A1 | 3/2015 | Yun et al. |
| 2015/0080700 A1 | 3/2015 | Fruland et al. |
| 2015/0099968 A1 | 4/2015 | Jamello |
| 2015/0099975 A1 | 4/2015 | Lam et al. |
| 2015/0119707 A1 | 4/2015 | Petroff |
| 2015/0133773 A1 | 5/2015 | Jaffer et al. |
| 2015/0133776 A1 | 5/2015 | Hoffman |
| 2015/0133789 A1 | 5/2015 | Ariura et al. |
| 2015/0153157 A1 | 6/2015 | Schmitt et al. |
| 2015/0164331 A1 | 6/2015 | Burgess et al. |
| 2015/0164423 A1 | 6/2015 | Webler |
| 2015/0182192 A1 | 7/2015 | Kaneko |
| 2015/0190054 A1 | 7/2015 | Kaneko |
| 2015/0192405 A1 | 7/2015 | Schmitt |
| 2015/0196285 A1 | 7/2015 | Mori |
| 2015/0209526 A1 | 7/2015 | Matsubara et al. |
| 2015/0216415 A1 | 8/2015 | Uribe-Patarroyo et al. |
| 2015/0219854 A1 | 8/2015 | Bhagavatula et al. |
| 2015/0230775 A1 | 8/2015 | Kobayashi |
| 2015/0238084 A1 | 8/2015 | Tearney et al. |
| 2015/0238121 A1 | 8/2015 | Tu et al. |
| 2015/0245768 A1 | 9/2015 | Hasegawa et al. |
| 2015/0257704 A1 | 9/2015 | Courtney |
| 2015/0257850 A1 | 9/2015 | Sakamoto |
| 2015/0265152 A1 | 9/2015 | Feldman et al. |
| 2015/0265162 A1 | 9/2015 | Lavi et al. |
| 2015/0268039 A1 | 9/2015 | Tu et al. |
| 2015/0282737 A1 | 10/2015 | Tolkowsky et al. |
| 2015/0297373 A1 | 10/2015 | Schmitt et al. |
| 2015/0306361 A1 | 10/2015 | Feig et al. |
| 2015/0320317 A1 | 11/2015 | Furuichi et al. |
| 2015/0366534 A1 | 12/2015 | Nair et al. |
| 2015/0370229 A1 | 12/2015 | Adler et al. |
| 2015/0371382 A1 | 12/2015 | Furuichi et al. |
| 2016/0000406 A1 | 1/2016 | Petroff |
| 2016/0007838 A1 | 1/2016 | Ariura et al. |
| 2016/0008090 A1 | 1/2016 | Yokoi et al. |
| 2016/0015337 A1 | 1/2016 | Inoue et al. |
| 2016/0018211 A1 | 1/2016 | Adler et al. |
| 2016/0022208 A1 | 1/2016 | Gopinath |
| 2016/0022248 A1 | 1/2016 | Mori et al. |
| 2016/0070066 A1 | 3/2016 | Schmitt et al. |
| 2016/0073885 A1 | 3/2016 | Adler |
| 2016/0089203 A1 | 3/2016 | Shimizu et al. |
| 2016/0089547 A1 | 3/2016 | Shimizu et al. |
| 2016/0092749 A1 | 3/2016 | Sakamoto |
| 2016/0093049 A1 | 3/2016 | Kobayashi |
| 2016/0095577 A1 | 4/2016 | Itoh et al. |
| 2016/0113485 A1 | 4/2016 | Nishiyama et al. |
| 2016/0120408 A1 | 5/2016 | Bhagavatula et al. |

(56) References Cited

U.S. PATENT DOCUMENTS

| | | |
|---|---|---|
| 2016/0120492 A1 | 5/2016 | Honma et al. |
| 2016/0124134 A1 | 5/2016 | Zhu et al. |
| 2016/0153765 A1 | 6/2016 | Yamazaki et al. |
| 2016/0157803 A1 | 6/2016 | Keller |
| 2016/0166815 A1 | 6/2016 | Suehara |
| 2016/0171701 A1 | 6/2016 | Zagrodsky et al. |
| 2016/0171711 A1 | 6/2016 | Gopinath et al. |
| 2016/0174925 A1 | 6/2016 | Dascal et al. |
| 2016/0199017 A1 | 7/2016 | Shimizu et al. |
| 2016/0202417 A1 | 7/2016 | Bhagavatula et al. |
| 2016/0206208 A1 | 7/2016 | Yamamoto et al. |
| 2016/0206267 A1 | 7/2016 | Shimizu et al. |
| 2016/0206290 A1 | 7/2016 | Itoh et al. |
| 2016/0228071 A1 | 8/2016 | Wang et al. |
| 2016/0270766 A1 | 9/2016 | Kobayashi |
| 2016/0301189 A1 | 10/2016 | Cable et al. |
| 2016/0313507 A1 | 10/2016 | Adler et al. |
| 2016/0320170 A1 | 11/2016 | Yun et al. |
| 2016/0320564 A1 | 11/2016 | Murashima et al. |
| 2016/0335763 A1 | 11/2016 | Ambwani et al. |
| 2016/0335766 A1 | 11/2016 | Ambwani et al. |
| 2016/0338753 A1 | 11/2016 | Ryba et al. |
| 2016/0341538 A1 | 11/2016 | Tumlinson et al. |
| 2016/0349417 A1 | 12/2016 | Tearney et al. |
| 2016/0370168 A1 | 12/2016 | Krol et al. |
| 2017/0014100 A1 | 1/2017 | Mori |
| 2017/0020392 A1 | 1/2017 | Xu |
| 2017/0024532 A1 | 1/2017 | Gopinath et al. |
| 2017/0024910 A1 | 1/2017 | Griffin et al. |
| 2017/0103520 A1 | 4/2017 | Gopinath et al. |
| 2017/0135663 A1 | 5/2017 | Dascal et al. |
| 2017/0140243 A1 | 5/2017 | Ambwani |
| 2017/0140531 A1 | 5/2017 | Dascal et al. |
| 2017/0140532 A1 | 5/2017 | Dascal et al. |
| 2017/0140560 A1 | 5/2017 | Kraus et al. |
| 2017/0143296 A1 | 5/2017 | Peterson et al. |
| 2017/0148161 A1 | 5/2017 | Griffin |
| 2017/0153439 A1 | 6/2017 | Horiike |
| 2017/0188831 A1 | 7/2017 | Adler et al. |
| 2017/0238809 A1 | 8/2017 | Tearney et al. |
| 2017/0261378 A1 | 9/2017 | Friedman et al. |
| 2017/0301084 A1 | 10/2017 | Gopinath |
| 2017/0309018 A1 | 10/2017 | Shalev et al. |
| 2017/0311806 A1 | 11/2017 | Comstock, II et al. |
| 2017/0325712 A1 | 11/2017 | Gopinath |
| 2017/0367581 A1 | 12/2017 | Tearney et al. |
| 2018/0003482 A1 | 1/2018 | Schmitt |
| 2018/0085095 A1 | 3/2018 | Hutchins et al. |
| 2018/0085170 A1 | 3/2018 | Gopinath |
| 2018/0125372 A1* | 5/2018 | Petroff .................. A61B 5/6852 |
| 2018/0172424 A1 | 6/2018 | Comstock, II et al. |
| 2018/0177404 A1 | 6/2018 | Liu |
| 2018/0192957 A1 | 7/2018 | Schmitt et al. |
| 2018/0192983 A1 | 7/2018 | Dascal et al. |
| 2018/0225830 A1 | 8/2018 | Gopinath et al. |
| 2018/0226773 A1 | 8/2018 | Yun et al. |
| 2018/0275622 A1 | 9/2018 | Adler et al. |
| 2018/0293730 A1 | 10/2018 | Ambwani et al. |
| 2018/0306569 A1 | 10/2018 | Schmitt et al. |
| 2018/0344173 A1 | 12/2018 | Tu et al. |
| 2018/0344174 A9 | 12/2018 | Schmitt et al. |
| 2018/0353241 A1 | 12/2018 | Tu et al. |
| 2019/0029623 A1 | 1/2019 | Kunio |
| 2019/0035114 A1 | 1/2019 | Griffin et al. |
| 2019/0096063 A1 | 3/2019 | Ambwani |
| 2019/0099237 A1 | 4/2019 | Booker et al. |
| 2019/0220980 A1 | 7/2019 | Ambwani et al. |
| 2019/0274528 A1 | 9/2019 | Petroff et al. |
| 2019/0307412 A1 | 10/2019 | Dascal et al. |
| 2019/0365480 A1 | 12/2019 | Gopinath et al. |
| 2019/0380594 A1 | 12/2019 | Schmitt et al. |
| 2020/0129067 A1 | 4/2020 | Krug et al. |
| 2020/0142575 A1 | 5/2020 | Gopinath et al. |
| 2020/0167923 A1 | 5/2020 | Gopinath |
| 2020/0288950 A1 | 9/2020 | Petroff et al. |
| 2020/0355557 A1 | 11/2020 | Friedman et al. |
| 2020/0397405 A1 | 12/2020 | Hutchins et al. |
| 2021/0004955 A1 | 1/2021 | Ambwani et al. |
| 2021/0045622 A1 | 2/2021 | Petroff et al. |
| 2021/0177282 A1 | 6/2021 | Ahmed et al. |
| 2021/0267442 A1 | 9/2021 | Petersen et al. |
| 2021/0318111 A1 | 10/2021 | Vakoc et al. |
| 2022/0142462 A1 | 5/2022 | Douk et al. |
| 2022/0142464 A1 | 5/2022 | Petroff et al. |
| 2022/0218206 A1 | 7/2022 | Petroff et al. |
| 2023/0000321 A1 | 1/2023 | Ughi et al. |
| 2023/0181016 A1 | 6/2023 | Ughi et al. |
| 2024/0000302 A1 | 1/2024 | Petroff et al. |
| 2024/0099564 A1 | 3/2024 | Petroff et al. |

FOREIGN PATENT DOCUMENTS

| | | |
|---|---|---|
| CN | 1780584 | 5/2006 |
| CN | 203801215 | 9/2014 |
| CN | 203801216 | 9/2014 |
| CN | 203805643 | 9/2014 |
| CN | 203805646 | 9/2014 |
| CN | 104126111 | 10/2014 |
| CN | 105019592 | 11/2015 |
| CN | 204826364 | 12/2015 |
| CN | 105662387 | 6/2016 |
| CN | 106570313 | 4/2017 |
| CN | 106650029 | 5/2017 |
| CN | 106805989 | 6/2017 |
| CN | 106974622 | 7/2017 |
| CN | 107115108 | 9/2017 |
| CN | 107133959 | 9/2017 |
| CN | 107233106 | 10/2017 |
| CN | 107745346 | 3/2018 |
| CN | 107978371 | 5/2018 |
| CN | 108022650 | 5/2018 |
| CN | 108038848 | 5/2018 |
| CN | 207464715 | 6/2018 |
| DE | 69738291 | 9/2008 |
| DE | 112016005442 | 8/2018 |
| DE | 112016005603 | 10/2018 |
| EP | 0883793 | 12/1998 |
| EP | 1685366 | 8/2006 |
| EP | 2505129 | 10/2012 |
| EP | 2803973 | 11/2014 |
| GB | 2512077 | 9/2014 |
| JP | 09168539 | 6/1997 |
| JP | 2000503237 | 3/2000 |
| JP | 2000097845 | 4/2000 |
| JP | 2000097846 | 4/2000 |
| JP | 2002214127 | 7/2002 |
| JP | 2005224399 | 8/2005 |
| JP | 2005230552 | 9/2005 |
| JP | 2005533610 | 11/2005 |
| JP | 2006271869 | 10/2006 |
| JP | 2007268131 | 10/2007 |
| JP | 20077267866 | 10/2007 |
| JP | 2008510586 | 4/2008 |
| JP | 2008523954 | 7/2008 |
| JP | 2009072291 | 4/2009 |
| JP | 4494203 | 6/2010 |
| JP | 2010167029 | 8/2010 |
| JP | 2010188138 | 9/2010 |
| JP | 2010533052 | 10/2010 |
| JP | 2011078550 | 4/2011 |
| JP | 2012147860 | 8/2012 |
| JP | 2012521852 | 9/2012 |
| JP | 2012205661 | 10/2012 |
| JP | 5093787 | 12/2012 |
| JP | 2012254211 | 12/2012 |
| JP | 2013500142 | 1/2013 |
| JP | 2013506136 | 2/2013 |
| JP | 2013521070 | 6/2013 |
| JP | 5269809 | 8/2013 |
| JP | 2014505496 | 3/2014 |
| JP | 5474190 | 4/2014 |
| JP | 2014180575 | 9/2014 |
| JP | 2014526283 | 10/2014 |
| JP | 5622796 | 11/2014 |

(56) References Cited

FOREIGN PATENT DOCUMENTS

| | | |
|---|---|---|
| JP | 5635149 | 12/2014 |
| JP | 5643315 | 12/2014 |
| JP | 2015013217 | 1/2015 |
| JP | 5689728 | 3/2015 |
| JP | 2015062638 | 4/2015 |
| JP | 5721721 | 5/2015 |
| JP | 2015518393 | 7/2015 |
| JP | 5778579 | 9/2015 |
| JP | 2015164660 | 9/2015 |
| JP | 5814860 | 11/2015 |
| JP | 2015532717 | 11/2015 |
| JP | 5856605 | 2/2016 |
| JP | 2016038329 | 3/2016 |
| JP | 2016508750 | 3/2016 |
| JP | 2016514996 | 5/2016 |
| JP | 5987025 | 9/2016 |
| JP | 5997232 | 9/2016 |
| JP | 2017524422 | 8/2017 |
| JP | 2018020158 | 2/2018 |
| JP | 2018507400 | 3/2018 |
| JP | 2018516147 | 6/2018 |
| JP | 2018527961 | 9/2018 |
| JP | 2018527995 | 9/2018 |
| JP | 2018192287 | 12/2018 |
| WO | 9732182 | 2/1997 |
| WO | 2004010856 | 2/2004 |
| WO | 2004096049 | 11/2004 |
| WO | 2005047813 | 5/2005 |
| WO | 2006022342 | 3/2006 |
| WO | 2006024015 | 3/2006 |
| WO | 2006068927 | 6/2006 |
| WO | 2008134449 | 11/2008 |
| WO | 2009009799 | 1/2009 |
| WO | 2009009802 | 1/2009 |
| WO | 2009010963 | 1/2009 |
| WO | 2010095370 | 8/2010 |
| WO | 2010113374 | 10/2010 |
| WO | 2011038010 | 3/2011 |
| WO | 2011059829 | 5/2011 |
| WO | 2012002302 | 1/2012 |
| WO | 2012064966 | 5/2012 |
| WO | 2013033415 | 3/2013 |
| WO | 2013126390 | 8/2013 |
| WO | 2014055908 | 4/2014 |
| WO | 2014142789 | 9/2014 |
| WO | 2014142815 | 9/2014 |
| WO | 2014149127 | 9/2014 |
| WO | 2014163601 | 10/2014 |
| WO | 2014175853 | 10/2014 |
| WO | 2015022760 | 2/2015 |
| WO | 2015044978 | 4/2015 |
| WO | 2015044982 | 4/2015 |
| WO | 2015044983 | 4/2015 |
| WO | 2015044984 | 4/2015 |
| WO | 2015074018 | 5/2015 |
| WO | 2015103277 | 7/2015 |
| WO | 2015136853 | 9/2015 |
| WO | 2015141136 | 9/2015 |
| WO | 2016168605 | 10/2016 |
| WO | 2016187218 | 11/2016 |
| WO | 2016187231 | 11/2016 |
| WO | 2016210132 | 12/2016 |
| WO | 2017011587 | 1/2017 |
| WO | 2017019626 | 2/2017 |
| WO | 2017019634 | 2/2017 |
| WO | 2015044987 | 3/2017 |
| WO | 2015045368 | 3/2017 |
| WO | 2017040484 | 3/2017 |
| WO | 2017097074 | 6/2017 |
| WO | 2017189942 | 11/2017 |
| WO | 2017200381 | 11/2017 |
| WO | 2019108598 | 6/2019 |
| WO | 2020061001 | 3/2020 |
| WO | 2020223433 | 11/2020 |
| WO | 2020237024 | 11/2020 |
| WO | 2021222530 | 11/2021 |
| WO | 2023133355 | 7/2023 |
| WO | 2024081414 | 4/2024 |

OTHER PUBLICATIONS

Athanasiou, L.S. et al. "Fully automated lumen segmentation of intracoronary optical coherence tomography images", Medical Imaging 2017, vol. 10133, pp. 101332I-1-101332I-7. Downloaded from the internet on Mar. 6, 2017: http://proceedings.spiedigitallibrary.org/.

Berger, J.D. et al. "Widely tunable external cavity diode laser based on a MEMS electrostatic rotary actuator", OSA/OFC 2001, pp. TuJ2-1-TuJ2-3.

BlazePhotonics. "NL-2.4-800 Highly nonlinear PCF" technical specification sheet.

Buus, J. et al. "Tunable Lasers in Optical Networks", Journal of Lightwave Technology, vol. 24, No. 1 (Jan. 2006), pp. 5-11.

Chang-Hasnain, C.J. "Tunable VCSEL", IEEE Journal on Selected Topics in Quantum Electronics, vol. 6, No. 6 (Nov./Dec. 2000), pp. 978-987.

Chang-Hasnain, C.J., "Progress and Prospects of Long-Wavelength VCSELs", IEEE Optical Communications (Feb. 2003), pp. S30-S34.

Chinn, S.R. et al. "Optical coherence tomography using a frequency-tunable optical source", Optics Letters, vol. 22, No. 5 (Mar. 1, 1997), pp. 340-342.

Chinese Notice of Allowance and Supplementary Search Report dated Jan. 13, 2021 issued in related Chinese Application No. 201680034490.4.

Chinese Office Action dated Aug. 28, 2019 issued in related Chinese Application No. 201680034490.4, with English translation.

Chinese Office Action dated Feb. 27, 2019 issued in related Chinese Application No. 201680034490.4, with English translation.

Chinese Office Action dated May 25, 2020 issued in related Chinese Application No. 201680034490.4, with English summary.

European Office Action dated Apr. 21, 2021 issued in corresponding European Application No. 16842796.1.

European Office Action dated Feb. 4, 2020 issued in related European Application No. 16780839.3.

Extended European Search Report dated Apr. 9, 2019 issued in related European Application No. 16842796.1.

Extended European Search Report dated Jan. 2, 2019 issued in related European Application No. 16780839.3.

Extended European Search Report dated Nov. 26, 2021 issued in corresponding European Application No. 18883166.3.

International Preliminary Report on Patentability dated Jun. 11, 2020 issued in related International Application No. PCT/US2018/062766.

International Preliminary Report on Patentability dated Mar. 15, 2018 issued in related International Application No. PCT/US2016/049415.

International Preliminary Report on Patentability dated Nov. 11, 2021 issued in corresponding International Application No. PCT/US20/30616.

International Preliminary Report on Patentability dated Oct. 17, 2017 issued in related International Application No. PCT/US2016/027764.

International Search Report & Written Opinion dated Feb. 11, 2019, issued in related International Application No. PCT/US2018/062766.

International Search Report and Written Opinion dated Aug. 2, 2021 issued in corresponding International Application No. PCT/US2021/029836.

International Search Report and Written Opinion dated Jan. 31, 2020 issued in related International Application No. PCT/US2019/051447.

International Search Report and Written Opinion dated Jul. 30, 2020 issued in related International Application No. PCT/US20/33953.

International Search Report and Written Opinion dated Sep. 14, 2020 issued in related International Application No. PCT/US20/30616.

(56) References Cited

OTHER PUBLICATIONS

International Search Report and Written Opinion dated Jul. 14, 2016 issued in related International Application No. PCT/US2016/027764.
International Search Report and Written Opinion dated Nov. 7, 2016, issued in related International Application No. PCT/US2016/049415.
Japanese Office Action dated Mar. 16, 2021 issued in related Japanese Application No. 2018-510969, with English language summary.
Japanese Office Action dated Mar. 31, 2020 issued in related Japanese Application No. 2018-505582, with English translation.
Japanese Office Action dated Nov. 17, 2020 issued in related Japanese Application No. 2018-505582, with English translation.
Japanese Office Action dated Sep. 15, 2020 issued in related Japanese Application No. 2018-510969, with English language summary.
Fermann, M.E. et al. "Ultrawide tunable Er solition fiber laser amplified in Yb-doped fiber", Optics Letters, vol. 24, No. 20 (Oct. 15, 1999), pp. 1428-1430.
Focabex, "Core Structure of Optical Cables" Article (online). Feb. 1, 2002 (retrieved Jan. 8, 2020). Retrieved from the Internet: URL: http://www.focabex.com/library-n/CORE-STRUCTURE-OF-OPTICAL-FIBER-CABLES.pdf.
Ghannam, M.T., et al. "Rheological Properties of Poly(dimethylsiloxane)". Industrial & Engineering Chemistry Research vol. 37, No. 4 (1998) pp. 1335-1340.
Golubovic, B. et al. "Optical frequency-domain reflectometry using rapid wavelength tuning of a Cr4+:forsterite laser", Optics Letters, vol. 22, No. 22 (Nov. 15, 1997), pp. 1704-1706.
Harris Jr., J.S. "Tunable Long-Wavelength Vertical-Cavity Lasers: The Engine of Next Generation Optical Networks?", IEEE Journal on Selected Topics in Quantum Electronics, vol. 6, No. 6 (Nov./Dec. 2000), pp. 1145-1160.
Introduction to silicone fluids (https://www.clearcoproducts.com/introduction-to-silicone-fluids.html), retrieved Sep. 24, 2020.
Xi, et al. "Diffractive catheter for ultrahigh-resolution spectral-domain volumetric OCT imaging", Optics Letters, vol. 39, No. 7, Optical Society of America, Mar. 26, 2014, pp. 2016-2019.
Kakuta, T. et al. "Behavior of optical fibers under heavy irradiation", Fusion Engineering and Design, vol. 41 (1998), pp. 201-205.
Madigan, Jeremy. "Vascular access: guide catheter selection, usage, and compatibility." Interventional Neuroradiology, Springer, London (2014), pp. 27-38.
Meuwissen, M. et al. "Role of Variability in Microvascular Resistance onFractional Flow Reserve and Coronary Blood Flow Velocity Reserve in Intermediate Coronary Lesions", Circulation, 103 (2001), pp. 184-187 [online—retrieved on Mar. 7, 2018]. Retrieved from the Internet URL: http://circ.ahajournals.org/content/103/2/184.
NKT Photonics. "ESM-12 Single0mode 12 um core fiber" technical specification sheet.
NKT Photonics. "HC-1550-02 Hollow Core Photonic Bandgap Fiber" technical specification sheet.
NKT Photonics. "HC-800-02 Hollow Core Photonic Bandgap Fiber" technical specification sheet.
Ofili, E.O. et al. "Differential characterization of blood flow, velocity, and vascular resistance between proximal and distal normal epicardial human coronary arteries: Analysis by intracoronary Doppler spectral flow velocity", American Heart Journal (Jul. 1995), pp. 37-46.
Reed, W.A. et al. "Gradient-index fiber-optic microprobes for minimally invasive in vivo low-coherence interferometry", Optics Letters, vol. 27, No. 20 (Oct. 15, 2002), pp. 1794-1796.
Tearney, G.J. et al. "High-speed phase- and group-delay scanning with a grating-based phase control delay line", Optics Letters, vol. 22, No. 23 (Dec. 1, 1997), pp. 1811-1813.

Thorlabs, "Single Wavelength Graded-Index (GRIN) Lenses" Product Catalogue (online). Apr. 9, 2016 (retrieved Jan. 8, 2020). Retrieved from the Internet: URL: https://www.thorlabs.com/NewGroupPage9.cfm?ObjectGroup_ID=1209.
Von der Weid, J.P. et al. "On the Characterization of Optical Fiber Network Components with Optical Frequency Domain Reflectometry", Journal of Lightwave Technology, vol. 15, No. 7 (Jul. 1997), pp. 1131-1141.
Youngquist, R.C. et al."Optical coherence-domain reflectometry: a new optical evaluation technique", Optics Letters, vol. 12, No. 3 (Mar. 1987), pp. 158-160.
Yun, S.H. et al. "High-speed optical frequency-domain imaging", Optics Express, vol. 11, No. 22 (Nov. 3, 2003), pp. 2953-2963.
Zheng, W. "Optic Lenses Manufactured on Fiber Ends", IEEE, 978-1-4673-7732-4/15, 2015, pp. 1-10.
International Report on Patentability dated Dec. 2, 2021 issued in corresponding International Application No. PCT/US2020/033953.
International Search Report and Written Opinion dated Apr. 14, 2023 issued in related International Application No. PCT/US2023/010508.
Atif et al. "Catheters for optical coherence tomography", Laser Physics Letters, vol. 8, No. 9, (Jul. 1, 2011), pp. 629-646.
Extended European Search Report dated Apr. 21, 2023 issued in corresponding European Application No. 20810126.1.
Japanese Office Action dated Apr. 25, 2023 issued in related Japanese Application No. 2021-514598, with English summary.
Japanese Office Action dated Feb. 21, 2023 issued in corresponding Japanese Application No. 2021-117103, with English summary.
Extended European Search Report dated Apr. 21, 2022 issued in corresponding European Application No. 19862071.8.
Tran et al. "In vivo endoscopic optical coherence tomography by use of a rotational microelectromechanical system probe", Optics Letters, vol. 29 No. 11 (Jun. 1, 2004), p. 1236-1238.
Japanese Office Action dated Apr. 26, 2022 issued in corresponding Japanese Application No. 2021-068226, with English translation.
Extended European Search Report dated Jun. 8, 2022 issued in related European Application No. 21217738.0.
Jung et al. "Handheld Optical Coherence Tomography Scanner for Primary Care Diagnostics", IEEE Transactions on Biomedical Engineering, Mar. 2011, vol. 58, No. 3, p. 741-744.
Japanese Office Action dated Aug. 2, 2022 issued in corresponding Japanese Application No. 2021-117103, with English translation.
Summons to Attend Oral Proceedings dated Mar. 17, 2023 issued in related European Application No. 16842796.1.
Brezinski et al. "Optical Coherence Tomography: High-Resolution Imaging in Nontransparent Tissue", IEEE Journal of Selected Topics in Quantum Electronics, vol. 5, No. 4, Jul./Aug. 1999, pp. 1185-1192.
Extended European Search Report dated Mar. 21, 2023 issued in related European Application No. 20798343.8.
Japanese Office Action dated Nov. 15, 2022 issued in related Japanese Application No. 2021-068226, with English translation.
International Preliminary Report on Patentability electronically transmitted to Applicant on Nov. 10, 2022, issued in related International Application No. PCT/US2021/029836.
Chinese Office Action dated Oct. 13, 2023 issued in Chinese Application No. 202110324448.9, with English summary.
Japanese Office Action dated Sep. 26, 2023 issued in Japanese Application No. 2022164724, with English summary.
International Search Report and Written Opinion dated Feb. 9, 2024 issued in International Application No. PCT/US2023/035132.
International Preliminary Report on Patentability dated Jul. 25, 2024 issued in International Application No. PCT/US2023/010508.
Japanese Office Action dated Nov. 12, 2024 issued in Japanese Application No. 2021568915, with English summary.

* cited by examiner

Flow Field i) Capture both angio data and t-wave trigger signals ii) Capture first sequence before pullback starts iii) Capture second sequence during pullback (contrast media flowing)

iv) Capture third sequence after pullback ends

SYSTEMS AND METHODS FOR OCT-GUIDED TREATMENT OF A PATIENT

RELATED APPLICATIONS

This application claims benefit of U.S. Provisional Application Ser. No. 62/850,945, titled "OCT-Guided Treatment of a Patient", filed May 21, 2019, the content of which is incorporated by reference in its entirety.

This application claims benefit of U.S. Provisional Application Ser. No. 62/906,353, titled "OCT-Guided Treatment of a Patient", filed Sep. 26, 2019, the content of which is incorporated by reference in its entirety.

This application claims benefit of U.S. Provisional Application Ser. No. 63/017,258, titled "Imaging System", filed Apr. 29, 2020, the content of which is incorporated by reference in its entirety.

This application is related to U.S. Provisional Application Ser. No. 62/148,355, titled "Micro-Optic Probes for Neurology", filed Apr. 16, 2015, the content of which is incorporated by reference in its entirety.

This application is related to U.S. Provisional Application Ser. No. 62/322,182, titled "Micro-Optic Probes for Neurology", filed Apr. 13, 2016, the content of which is incorporated by reference in its entirety.

This application is related to International PCT Patent Application Serial Number PCT/US2016/027764, titled "Micro-Optic Probes for Neurology" filed Apr. 15, 2016, Publication Number WO 2016/168605, published Oct. 20, 2016, the content of which is incorporated by reference in its entirety.

This application is related to U.S. patent application Ser. No. 15/566,041, titled "Micro-Optic Probes for Neurology", filed Oct. 12, 2017, United States Publication Number 2018-0125372, published May 10, 2018, the content of which is incorporated by reference in its entirety.

This application is related to U.S. Provisional Application Ser. No. 62/212,173, titled "Imaging System Includes Imaging Probe and Delivery Devices", filed Aug. 31, 2015, the content of which is incorporated by reference in its entirety.

This application is related to U.S. Provisional Application Ser. No. 62/368,387, titled "Imaging System Includes Imaging Probe and Delivery Devices", filed Jul. 29, 2016, the content of which is incorporated by reference in its entirety.

This application is related to International PCT Patent Application Serial Number PCT/US2016/049415, titled "Imaging System Includes Imaging Probe and Delivery Devices", filed Aug. 30, 2016, Publication Number WO 2017/040484, published Mar. 9, 2017, the content of which is incorporated by reference in its entirety.

This application is related to U.S. patent application Ser. No. 15/751,570, titled "Imaging System Includes Imaging Probe and Delivery Devices", filed Feb. 9, 2018, U.S. Pat. No. 10,631,718, issued Apr. 28, 2020, the content of which is incorporated by reference in its entirety.

This application is related to U.S. patent application Ser. No. 16/820,991, titled "Imaging System Includes Imaging Probe and Delivery Devices", filed Mar. 17, 2020, Publication Number 2021-0045622, published Feb. 18, 2021, the content of which is incorporated by reference in its entirety.

This application is related to U.S. Provisional Application Ser. No. 62/591,403, titled "Imaging System", filed Nov. 28, 2017, the content of which is incorporated by reference in its entirety.

This application is related to U.S. Provisional Application Ser. No. 62/671,142, titled "Imaging System", filed May 14, 2018, the content of which is incorporated by reference in its entirety.

This application is related to International PCT Patent Application Serial Number PCT/US2018/062766, titled "Imaging System", filed Nov. 28, 2018, Publication Number WO 2019/108598, published Jun. 6, 2019, the content of which is incorporated by reference in its entirety.

This application is related to U.S. Provisional Application Ser. No. 62/732,114, titled "Imaging System with Optical Pathway", filed Sep. 17, 2018, the content of which is incorporated by reference in its entirety.

This application is related to International PCT Patent Application Serial Number PCT/US2019/051447, titled "Imaging System with Optical Pathway", filed Sep. 17, 2019, Publication Number WO 2020/061001, published Mar. 26, 2020, the content of which is incorporated by reference in its entirety.

This application is related to U.S. Provisional Application Ser. No. 62/840,450, titled "Imaging Probe with Fluid Pressurization Element", filed Apr. 30, 2019, the content of which is incorporated by reference in its entirety.

This application is related to International PCT Patent Application Serial Number PCT/US2020/030616, titled "Imaging Probe with Fluid Pressurization Element", filed Apr. 30, 2020, Publication Number WO 2020/223433, published Nov. 5, 2020, the content of which is incorporated by reference in its entirety.

FIELD OF THE INVENTION

The present invention relates generally to optical coherence tomography (OCT) imaging systems, and in particular, to systems that provide guidance for therapeutic treatment of a patient.

BACKGROUND

Imaging probes have been commercialized for imaging various internal locations of a patient, such as an intravascular probe for imaging a patient's heart. Current imaging probes are limited in their ability to reach certain anatomical locations due to their size and rigidity. Current imaging probes are inserted over a guidewire, which can compromise their placement and limit use of one or more delivery catheters through which the imaging probe is inserted. There is a need for imaging systems that include probes with reduced diameter and high flexibility, as well as systems with one or more delivery devices compatible with these improved imaging probes.

SUMMARY

According to an aspect of the present inventive concepts, an imaging system for a patient comprises an imaging probe, an optical assembly, and an imaging assembly. The imaging probe comprises: an elongate shaft comprising a proximal end, a distal portion, and a lumen extending between the proximal end and the distal portion; a rotatable optical core comprising a proximal end and a distal end, and at least a portion of the rotatable optical core is positioned within the lumen of the elongate shaft. The optical assembly is positioned proximate the distal end of the rotatable optical core and is configured to direct light to tissue and collect reflected light from the tissue. The imaging assembly is constructed and arranged to optically couple to the imaging probe and is configured to emit light into the imaging probe and receive the reflected light collected by the optical assembly. The system can be configured to provide treatment information, and the treatment information can be used by an operator to plan a treatment and/or predict a treatment outcome.

In some embodiments, the imaging probe further comprises a damping fluid positioned between the elongate shaft and the rotatable optical core and configured to reduce non-uniform rotation of the optical assembly. The imaging probe can further comprise a fluid pressurization element configured to increase the pressure of the damping fluid to reduce the presence of bubbles proximate the optical assembly.

In some embodiments, the treatment information is based on OCT data gathered by the imaging probe. The system can further comprise a second imaging device configured to gather non-OCT data, and the treatment information can be further based on the non-OCT data. The second imaging device can be configured to gather non-OCT data comprising angiography data.

In some embodiments, the system is configured to produce an assessment of disease severity. The assessment can comprise a quantified assessment and/or a qualitative assessment.

In some embodiments, the system is configured to accurately capture a clot of 5 µm or more, 10 µm or more, or 30 µm or more.

The technology described herein, along with the attributes and attendant advantages thereof, will best be appreciated and understood in view of the following detailed description taken in conjunction with the accompanying drawings in which representative embodiments are described by way of example.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE DRAWINGS

Figure 1:
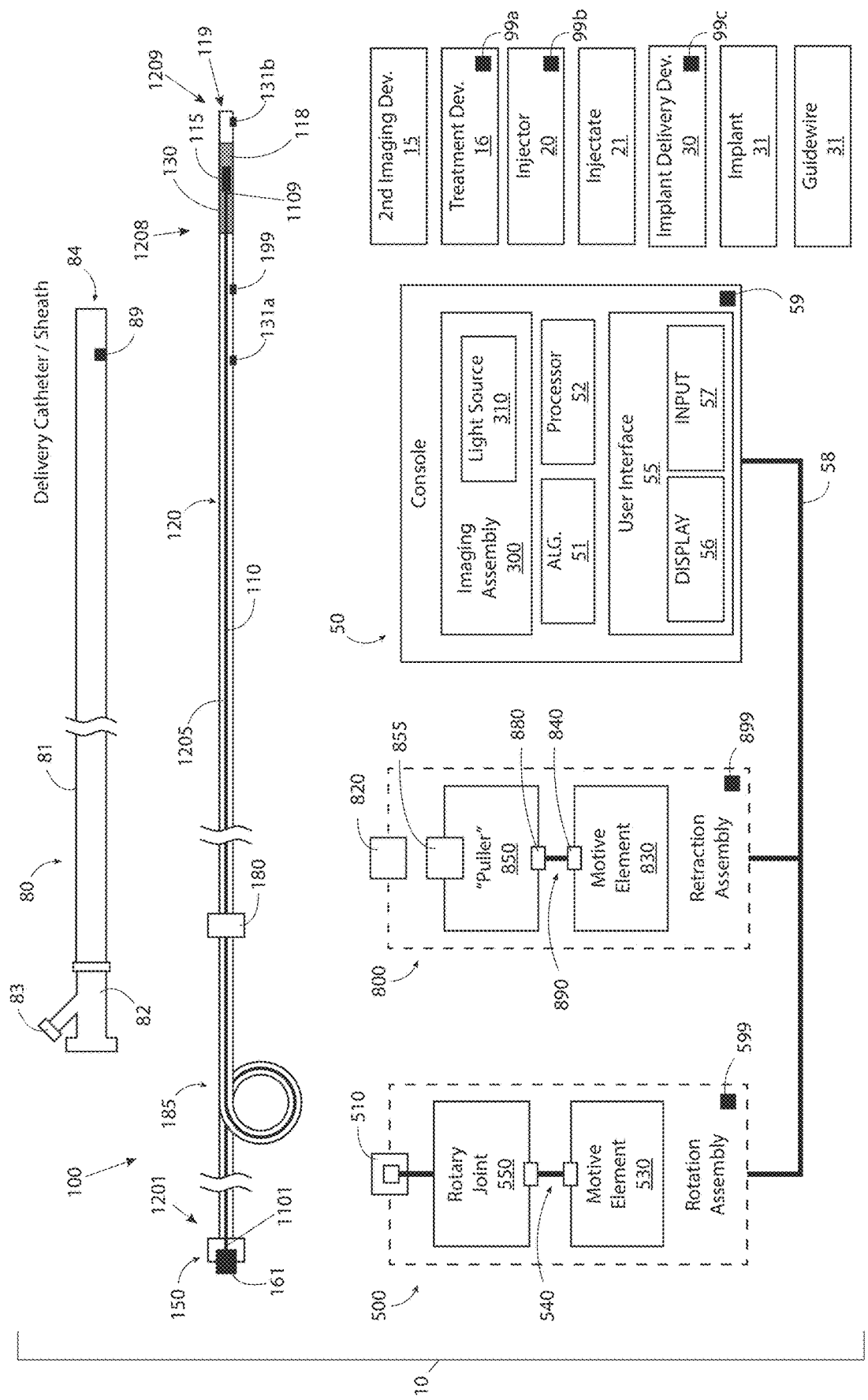
FIG. 1 illustrates a schematic view of an imaging system comprising an imaging probe and independent retraction and rotation assemblies, consistent with the present inventive concepts.

Reference will now be made in detail to the present embodiments of the technology, examples of which are illustrated in the accompanying drawings. Similar reference numbers may be used to refer to similar components. However, the description is not intended to limit the present disclosure to particular embodiments, and it should be construed as including various modifications, equivalents, and/or alternatives of the embodiments described herein.

It will be understood that the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") when used herein, specify the presence of stated features, integers, steps, operations, elements, and/or components, but do not preclude the presence or addition of one or more other features, integers, steps, operations, elements, components, and/or groups thereof.

It will be further understood that, although the terms first, second, third, etc. may be used herein to describe various limitations, elements, components, regions, layers and/or sections, these limitations, elements, components, regions, layers and/or sections should not be limited by these terms. These terms are only used to distinguish one limitation, element, component, region, layer or section from another limitation, element, component, region, layer or section. Thus, a first limitation, element, component, region, layer or section discussed below could be termed a second limitation, element, component, region, layer or section without departing from the teachings of the present application.

It will be further understood that when an element is referred to as being "on", "attached", "connected" or "coupled" to another element, it can be directly on or above, or connected or coupled to, the other element, or one or more intervening elements can be present. In contrast, when an element is referred to as being "directly on", "directly attached", "directly connected" or "directly coupled" to another element, there are no intervening elements present. Other words used to describe the relationship between elements should be interpreted in a like fashion (e.g. "between" versus "directly between," "adjacent" versus "directly adjacent," etc.).

It will be further understood that when a first element is referred to as being "in", "on" and/or "within" a second element, the first element can be positioned: within an internal space of the second element, within a portion of the second element (e.g. within a wall of the second element); positioned on an external and/or internal surface of the second element; and combinations of one or more of these.

As used herein, the term "proximate", when used to describe proximity of a first component or location to a second component or location, is to be taken to include one or more locations near to the second component or location, as well as locations in, on and/or within the second component or location. For example, a component positioned proximate an anatomical site (e.g. a target tissue location), shall include components positioned near to the anatomical site, as well as components positioned in, on and/or within the anatomical site.

Spatially relative terms, such as "beneath," "below," "lower," "above," "upper" and the like may be used to describe an element and/or feature's relationship to another element(s) and/or feature(s) as, for example, illustrated in the figures. It will be further understood that the spatially relative terms are intended to encompass different orientations of the device in use and/or operation in addition to the orientation depicted in the figures. For example, if the device in a figure is turned over, elements described as "below" and/or "beneath" other elements or features would then be oriented "above" the other elements or features. The device can be otherwise oriented (e.g. rotated 90 degrees or at other orientations) and the spatially relative descriptors used herein interpreted accordingly.

The terms "reduce", "reducing", "reduction" and the like, where used herein, are to include a reduction in a quantity, including a reduction to zero. Reducing the likelihood of an occurrence shall include prevention of the occurrence. Correspondingly, the terms "prevent", "preventing", and "prevention" shall include the acts of "reduce", "reducing", and "reduction", respectively.

The term "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

The term "one or more", where used herein can mean one, two, three, four, five, six, seven, eight, nine, ten, or more, up to any number.

The terms "and combinations thereof" and "and combinations of these" can each be used herein after a list of items that are to be included singly or collectively. For example, a component, process, and/or other item selected from the group consisting of: A; B; C; and combinations thereof, shall include a set of one or more components that comprise: one, two, three or more of item A; one, two, three or more of item B; and/or one, two, three, or more of item C.

In this specification, unless explicitly stated otherwise, "and" can mean "or", and "or" can mean "and". For example, if a feature is described as having A, B, or C, the feature can have A, B, and C, or any combination of A, B, and C. Similarly, if a feature is described as having A, B, and C, the feature can have only one or two of A, B, or C.

As used herein, when a quantifiable parameter is described as having a value "between" a first value X and a second value Y, it shall include the parameter having a value of: at least X, no more than Y, and/or at least X and no more than Y. For example, a length of between 1 and 10 shall include a length of at least 1 (including values greater than 10), a length of less than 10 (including values less than 1), and/or values greater than 1 and less than 10.

The expression "configured (or set) to" used in the present disclosure may be used interchangeably with, for example, the expressions "suitable for", "having the capacity to", "designed to", "adapted to", "made to" and "capable of" according to a situation. The expression "configured (or set) to" does not mean only "specifically designed to" in hardware. Alternatively, in some situations, the expression "a device configured to" may mean that the device "can" operate together with another device or component.

As used herein, the terms "about" or "approximately" shall refer to +30%.

As used herein, the term "threshold" refers to a maximum level, a minimum level, and/or range of values correlating to a desired or undesired state. In some embodiments, a system parameter is maintained above a minimum threshold, below a maximum threshold, within a threshold range of values, and/or outside a threshold range of values, such as to cause a desired effect (e.g. efficacious therapy) and/or to prevent or otherwise reduce (hereinafter "prevent") an undesired event (e.g. a device and/or clinical adverse event). In some embodiments, a system parameter is maintained above a first threshold (e.g. above a first temperature threshold to cause a desired therapeutic effect to tissue) and below a second threshold (e.g. below a second temperature threshold to prevent undesired tissue damage). In some embodiments, a threshold value is determined to include a safety margin, such as to account for patient variability, system variability, tolerances, and the like. As used herein, "exceeding a threshold" relates to a parameter going above a maximum threshold, below a minimum threshold, within a range of threshold values and/or outside of a range of threshold values.

As described herein, "room pressure" shall mean pressure of the environment surrounding the systems and devices of the present inventive concepts. Positive pressure includes pressure above room pressure or simply a pressure that is greater than another pressure, such as a positive differential pressure across a fluid pathway component such as a valve. Negative pressure includes pressure below room pressure or a pressure that is less than another pressure, such as a negative differential pressure across a fluid component pathway such as a valve. Negative pressure can include a vacuum but does not imply a pressure below room pressure. As used herein, the term "vacuum" can be used to refer to a full or partial vacuum, or any negative pressure as described herein.

The term "diameter" where used herein to describe a non-circular geometry is to be taken as the diameter of a hypothetical circle approximating the geometry being described. For example, when describing a cross section, such as the cross section of a component, the term "diameter" shall be taken to represent the diameter of a hypothetical circle with the same cross sectional area as the cross section of the component being described.

The terms "major axis" and "minor axis" of a component where used herein are the length and diameter, respectively, of the smallest volume hypothetical cylinder which can completely surround the component.

As used herein, the term "functional element" is to be taken to include one or more elements constructed and arranged to perform a function. A functional element can comprise a sensor and/or a transducer. In some embodiments, a functional element is configured to deliver energy and/or otherwise treat tissue (e.g. a functional element configured as a treatment element). Alternatively or additionally, a functional element (e.g. a functional element comprising a sensor) can be configured to record one or more parameters, such as a patient physiologic parameter; a patient anatomical parameter (e.g. a tissue geometry parameter); a patient environment parameter; and/or a system parameter. In some embodiments, a sensor or other functional element is configured to perform a diagnostic function (e.g. to gather data used to perform a diagnosis). In some embodiments, a functional element is configured to perform a therapeutic function (e.g. to deliver therapeutic energy and/or a therapeutic agent). In some embodiments, a functional element comprises one or more elements constructed and arranged to perform a function selected from the group consisting of: deliver energy; extract energy (e.g. to cool a component); deliver a drug or other agent; manipulate a system component or patient tissue; record or otherwise sense a parameter such as a patient physiologic parameter or a system parameter; and combinations of one or more of these. A functional element can comprise a fluid and/or a fluid delivery system. A functional element can comprise a reservoir, such as an expandable balloon or other fluid-maintaining reservoir. A "functional assembly" can comprise an assembly constructed and arranged to perform a function, such as a diagnostic and/or therapeutic function. A functional assembly can comprise an expandable assembly. A functional assembly can comprise one or more functional elements.

The term "transducer" where used herein is to be taken to include any component or combination of components that receives energy or any input, and produces an output. For example, a transducer can include an electrode that receives electrical energy, and distributes the electrical energy to tissue (e.g. based on the size of the electrode). In some configurations, a transducer converts an electrical signal into any output, such as: light (e.g. a transducer comprising a light emitting diode or light bulb), sound (e.g. a transducer comprising a piezo crystal configured to deliver ultrasound energy); pressure (e.g. an applied pressure or force); heat energy; cryogenic energy; chemical energy; mechanical energy (e.g. a transducer comprising a motor or a solenoid);

magnetic energy; and/or a different electrical signal (e.g. different than the input signal to the transducer). Alternatively or additionally, a transducer can convert a physical quantity (e.g. variations in a physical quantity) into an electrical signal. A transducer can include any component that delivers energy and/or an agent to tissue, such as a transducer configured to deliver one or more of: electrical energy to tissue (e.g. a transducer comprising one or more electrodes); light energy to tissue (e.g. a transducer comprising a laser, light emitting diode and/or optical component such as a lens or prism); mechanical energy to tissue (e.g. a transducer comprising a tissue manipulating element); sound energy to tissue (e.g. a transducer comprising a piezo crystal); chemical energy; electromagnetic energy; magnetic energy; and combinations of one or more of these.

As used herein, the term "fluid" can refer to a liquid, gas, gel, or any flowable material, such as a material which can be propelled through a lumen and/or opening.

As used herein, the term "material" can refer to a single material, or a combination of two, three, four, or more materials.

As used herein, the term "lesion" comprises a segment of a blood vessel (e.g. an artery) that is in an undesired state. As used herein, lesion shall include a narrowing of a blood vessel (e.g. a stenosis), and/or a segment of a blood vessel, with or without narrowing, that includes a buildup of calcium, lipids, cholesterol, and/or other plaque.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination. For example, it will be appreciated that all features set out in any of the claims (whether independent or dependent) can be combined in any given way.

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Terms defined in the present disclosure are only used for describing specific embodiments of the present disclosure and are not intended to limit the scope of the present disclosure. Terms provided in singular forms are intended to include plural forms as well, unless the context clearly indicates otherwise. All of the terms used herein, including technical or scientific terms, have the same meanings as those generally understood by an ordinary person skilled in the related art, unless otherwise defined herein. Terms defined in a generally used dictionary should be interpreted as having meanings that are the same as or similar to the contextual meanings of the relevant technology and should not be interpreted as having ideal or exaggerated meanings, unless expressly so defined herein. In some cases, terms defined in the present disclosure should not be interpreted to exclude the embodiments of the present disclosure.

Provided herein are imaging systems for a patient comprising an imaging probe and an imaging assembly. The imaging probe comprises an elongate shaft comprising a proximal end, a distal portion, and a lumen extending between the proximal end and the distal portion; a rotatable optical core comprising a proximal end and a distal end, wherein at least a portion of the rotatable optical core is positioned within the lumen of the elongate shaft; and an optical assembly positioned proximate the distal end of the rotatable optical core, the optical assembly configured to direct light to tissue and collect reflected light from the tissue.

The imaging systems of the present inventive concepts can be used to provide image data representing arteries, veins, and/or other body conduits, and to image one or more devices inserted into those conduits. The imaging systems can provide image data related to healthy tissue, as well as diseased tissue, such as blood vessels including a stenosis, lesion, myocardial bridge, and/or other vessel narrowing ("stenosis" herein) and/or blood vessels including an aneurysm. The system can be configured to provide treatment information, wherein the treatment information is used by an operator to plan a treatment and/or predict a treatment outcome.

Referring now to FIG. 1, a schematic view of an imaging system comprising an imaging probe and independent retraction and rotation assemblies is illustrated, consistent with the present inventive concepts. Imaging system 10 is constructed and arranged to collect image data and produce one or more images based on the recorded data, such as when imaging system 10 comprises an Optical Coherence Tomography (OCT) imaging system constructed and arranged to collect image data of an imaging location (e.g. a segment of a blood vessel, such as during a pullback procedure). Imaging system 10 comprises a catheter-based probe, imaging probe 100, as well as a rotation assembly 500 and a retraction assembly 800, each of which can operably attach to imaging probe 100. Imaging system 10 can further comprise console 50 which is configured to operably connect to imaging probe 100, such as via rotation assembly 500 and/or retraction assembly 800. Imaging probe 100 can be introduced into a conduit of the patient, such as a blood vessel or other conduit of the patient, using one or more delivery catheters, for example delivery catheter 80 shown. Additionally or alternatively, imaging probe 100 can be introduced through an introducer device, such as an endoscope, arthroscope, balloon dilator, or the like. In some embodiments, imaging probe 100 is configured to be introduced into a conduit selected from the group consisting of: an artery; a vein; an artery within or proximate the heart; a vein within or proximate the heart; an artery within or proximate the brain; a vein within or proximate the brain; a peripheral artery; a peripheral vein; through a natural body orifice into a conduit, such as the esophagus; through a surgically created orifice into a body cavity, such as the abdomen; and combinations of one or more of these. Imaging system 10 can further comprise multiple imaging devices, second imaging device 15 shown. Imaging system 10 can further comprise a device configured to treat the patient, treatment device 16. Imaging system 10 can further comprise a fluid injector, such as injector 20, which can be configured to inject one or more fluids, such as a flushing fluid, an imaging contrast agent (e.g. a radiopaque contrast agent, hereinafter "contrast") and/or other fluid, such as injectate 21 shown. Imaging system 10 can further comprise an implant, such as implant 31, which can be implanted in the patient via a delivery device, such as an implant delivery device 30 and/or delivery catheter 80.

In some embodiments, imaging probe 100 and/or another component of imaging system 10 can be of similar construction and arrangement to the similar components described in applicants co-pending U.S. patent application Ser. No. 15/566,041, titled "Micro-Optic Probes for Neurology", filed Oct. 12, 2017; the content of which is incorporated herein by reference in its entirety for all purposes. Imaging probe 100 can be constructed and arranged to collect image data from a patient site, such as an intravascular cardiac site, an intracranial site, or other site accessible via the vasculature of the patient. In some embodiments, imaging system 10 can be of similar construction and arrangement to the similar systems and their methods of use described in applicants co-pending U.S. patent application Ser. No. 15/751,570, titled "Imaging System Includes Imaging Probe and Delivery Devices", filed Feb. 9, 2018; the content of which is incorporated herein by reference in its entirety for all purposes.

Delivery catheter 80 comprises an elongate shaft, shaft 81, with a lumen 84 therethrough, and a connector 82 positioned on its proximal end. Connector 82 can comprise a Touhy or valved connector, such as a valved connector configured to prevent fluid egress from the associated delivery catheter 80 (with and/or without a separate shaft positioned within the connector 82). Connector 82 can comprise a port 83, such as a port constructed and arranged to allow introduction of fluid into delivery catheter 80 and/or for removing fluids from delivery catheter 80. In some embodiments, a flushing fluid, as described herein, is introduced via one or more ports 83, such as to remove blood or other undesired material from locations proximate optical assembly 115 (e.g. from a location proximal to optical assembly 115 to a location distal to optical assembly 115). Port 83 can be positioned on a side of connector 82 and can include a luer fitting and a cap and/or valve. Shafts 81, connectors 82, and ports 83 can each comprise standard materials and be of similar construction to commercially available introducers, guide catheters, diagnostic catheters, intermediate catheters and microcatheters used in interventional procedures. Delivery catheter 80 can comprise a catheter configured to deliver imaging probe 100 to an intracerebral location, an intracardiac location; and/or another location within a patient.

Imaging system 10 can comprise two or more delivery catheters 80, such as three or more delivery catheters 80. Multiple delivery catheters 80 can comprise at least a vascular introducer, and other delivery catheters 80 that can be inserted into the patient therethrough, after the vascular introducer is positioned through the skin of the patient. Two or more delivery catheters 80 can collectively comprise sets of inner diameters (IDs) and outer diameters (ODs) such that a first delivery catheter 80 slidingly receives a second delivery catheter 80 (e.g. the second delivery catheter OD is less than or equal to the first delivery catheter ID), and the second delivery catheter 80 slidingly receives a third delivery catheter 80 (e.g. the third delivery catheter OD is less than or equal to the second delivery catheter ID), and so on. In these configurations, the first delivery catheter 80 can be advanced to a first anatomical location, the second delivery catheter 80 can be advanced through the first delivery catheter to a second anatomical location distal or otherwise remote (hereinafter "distal") to the first anatomical location, and so on as appropriate, using sequentially smaller diameter delivery catheters 80. In some embodiments, delivery catheters 80 can be of similar construction and arrangement to the similar components described in applicants co-pending U.S. patent application Ser. No. 15/751,570, titled "Imaging System Includes Imaging Probe and Delivery Devices", filed Feb. 9, 2018; the content of which is incorporated herein by reference in its entirety for all purposes.

Imaging probe 100 comprises an elongate body, comprising one or more elongate shafts and/or tubes, elongate shaft 120 herein. Shaft 120 comprises a proximal end 1201, distal end 1209, and a lumen 1205 extending therebetween. In some embodiments, lumen 1205 can include multiple coaxial lumens within the one or more elongate shafts 120, such as one or more lumens abutting each other to define a single lumen 1205. In some embodiments, at least a portion of shaft 120 comprises a torque shaft. In some embodiments, a portion of shaft 120 comprises a braided construction. In some embodiments, a portion of shaft 120 comprises a spiral cut tube (e.g. a spiral cut metal tube). In some embodiments, the pitch of the spiral cut can be varied along the length of the cut, such as to vary the stiffness of shaft 120 along the cut. A portion of shaft 120 can comprise a tube constructed of nickel-titanium alloy. Shaft 120 operably surrounds a rotatable optical fiber, optical core 110 (e.g. optical core 110 is positioned within lumen 1205), comprising a proximal end 1101 and a distal end 1109. Optical core 110 can comprise a dispersion shifted optical fiber, such as a depressed cladding dispersion shifted fiber (e.g. a Non-Zero Dispersion Shifted, NZDS, fiber). Shaft 120 further comprises a distal portion 1208, including a transparent window, window 130 (e.g. a window that is relatively transparent to the one or more frequencies of light transmitted through optical core 110). An optical assembly, optical assembly 115, is operably attached to the distal end 1109 of optical core 110. Optical assembly 115 is positioned within window 130 of shaft 120. Optical assembly 115 can comprise a GRIN lens optically coupled to the distal end 1109 of optical core 110. Optical assembly 115 can comprise a construction and arrangement similar to optical assembly 115 as described in applicant's co-pending International PCT Patent Application Serial Number PCT/US2018/062766, titled "Imaging System", filed Nov. 28, 2018, and applicant's co-pending International PCT Patent Application Serial Number PCT/US2019/051447, titled "Imaging System with Optical Pathway", filed Sep. 17, 2019, the content of each of which is incorporated herein by reference in its entirety for all purposes. A connector assembly, connector assembly 150, is positioned on the proximal end of shaft 120. Connector assembly 150 operably attaches imaging probe 100 to rotation assembly 500, as described herein. Connector assembly 150 surrounds and operably attaches to an optical connector 161, fixedly attached to the proximal end of optical core 110. A second connector, pullback connector 180, is positioned on shaft 120. Connector 180 can be removably attached and/or adjustably positioned along the length of shaft 120. Connector 180 can be positioned along shaft 120, such as by a clinician or other user of system 10, proximate the proximal end of delivery catheter 80 after imaging probe 100 has been inserted into a patient via delivery catheter 80. Shaft 120 can comprise a portion between connector assembly 150 and the placement location of connector 180 that accommodates slack in shaft 120, a proximal portion of shaft 120 (e.g. a proximal portion of imaging probe 100), service loop 185.

Imaging probe 100 can comprise one or more visualizable markers along its length (e.g. along shaft 120), markers 131a-b shown (marker 131 herein). Marker 131 can comprise markers selected from the group consisting of: radiopaque markers; ultrasonically reflective markers; magnetic markers; ferrous material; and combinations of one or more of these. In some embodiments, marker 131 comprises a marker positioned at a location (e.g. a location within and/or at least proximate distal portion 1208) to assist a user of imaging system 10 in performing a pullback procedure ("pullback procedure" or "pullback" herein), such as to cause tip 119 to be positioned at a location distal to the proximal end of an implant after the pullback is completed (e.g. so that imaging probe 100 can be safely advanced through the implant after the pullback).

In some embodiments, imaging probe 100 includes a viscous dampening material, gel 118, positioned within shaft 120 and surrounding optical assembly 115 and a distal portion of optical core 110 (e.g. a gel injected or otherwise installed in a manufacturing process). Gel 118 can comprise a non-Newtonian fluid, for example a shear-thinning fluid. In some embodiments, gel 118 comprises a static viscosity of greater than 500 centipoise, and a shear viscosity that is less than the static viscosity. In these embodiments, the ratio of static viscosity to shear viscosity of gel 118 can be between 1.2:1 and 100:1. Gel 118 can comprise a gel as described in reference to applicants co-pending U.S. patent application Ser. No. 15/566,041, titled "Micro-Optic Probes for Neurology", filed Oct. 12, 2017, and applicant's co-pending International PCT Patent Application Serial Number PCT/US2018/062766, titled "Imaging System", filed Nov. 28, 2018, the content of each of which is incorporated herein by reference in its entirety for all purposes.

Imaging probe 100 can include a distal tip portion, distal tip 119. In some embodiments, distal tip 119 can comprise a spring tip, such as a spring tip configured to improve the "navigability" of imaging probe 100 (e.g. to improve "trackability" and/or "steerability" of imaging probe 100), for example within a tortuous pathway (e.g. within a blood vessel of the brain or heart with a tortuous pathway). In some embodiments, tip 119 comprises a length of between 5 mm and 100 mm (e.g. a spring with a length between 5 mm and 100 mm). In some embodiments, spring tip 119 can comprise a user shapeable spring tip (e.g. at least a portion of spring tip 119 is malleable). Imaging probe 100 can be rotated (e.g. via connector 180) to adjust the direction of a non-linear shaped portion of spring tip 119 (e.g. to adjust the trajectory of spring tip 119 in the vasculature of the patient). Alternatively or additionally, tip 119 can comprise a cap, plug, or other element configured to seal the distal opening of window 130. In some embodiments, tip 119 can comprise a radiopaque marker configured to increase the visibility of imaging probe 100 under an X-ray or fluoroscope. In some embodiments, tip 119 can comprise a relatively short luminal guidewire pathway to allow "rapid exchange" translation of imaging probe 100 over a guidewire of system 10 (such as guidewire 31).

In some embodiments, at least the distal portion of imaging probe 100 (e.g. the distal portion of shaft 120 surrounding optical assembly 115) comprises an outer diameter of no more than 0.030", such as no more than 0.025", no more than 0.020", and/or no more than 0.016".

In some embodiments, imaging probe 100 can be constructed and arranged for use in an intravascular neural procedure (e.g. a procedure in which the blood, vasculature, and other tissue proximate the brain are visualized, and/or devices positioned temporarily or permanently proximate the brain are visualized). An imaging probe 100 configured for use in a neural procedure can comprise an overall length of at least 150 cm, such as a length of approximately 300 cm.

Alternatively or additionally, imaging probe 100 can be constructed and arranged for use in an intravascular cardiac procedure (e.g. a procedure in which the blood, vasculature, and other tissue proximate the heart are visualized, and/or devices positioned temporarily or permanently proximate the heart are visualized). An imaging probe 100 configured for use in a cardiovascular procedure can comprise an overall length of at least 120 cm, such as an overall length of approximately 280 cm (e.g. to allow placement of the proximal end of probe 100 outside of the sterile field). In some embodiments, such as for placement outside of the sterile field, imaging probe 100 can comprise a length greater than 220 cm and/or less than 320 cm.

Rotation assembly 500 comprises a connector assembly 510, operably attached to a rotary joint 550. Rotation assembly 500 further comprises a motor or other rotational energy source, motive element 530. Motive element 530 is operably attached to rotary joint 550 via a linkage assembly 540. In some embodiments, linkage assembly 540 comprises one or more gears, belts, pulleys, or other force transfer mechanisms. Motive element 530 can drive (e.g. rotate via linkage assembly 540) rotary joint 550 (and in turn core 110) at speeds of at least 100 rotations per second, such as at least 200 rotations per second, 250 rotations per second, 400 rotations per second, 500 rotations per second, or between 20 rotations per second and 1000 rotations per second. Motive element 530 can comprise a mechanism selected from the group consisting of: a motor; a servo; a stepper motor (e.g. a stepper motor including a gear box); a linear actuator; a hollow core motor; and combinations thereof. In some embodiments, rotation assembly 500 is configured to rotate optical assembly 115 and rotatable optical core 110 in unison.

Connector assembly 510 operably attaches to connector assembly 150 of imaging probe 100, allowing optical connector 161 to operably engage rotary joint 550. In some embodiments, connector assembly 510 operably engages connector assembly 150. In some embodiments, connector assembly 510 operably engages connector assembly 150 such that rotary joint 550 and optical connector 161 are free to rotate within the engaged assemblies.

Retraction assembly 800 comprises a connector assembly 820, that operably attaches to a reference point, for example connector 82 of delivery catheter 80, such as to establish a reference for retraction assembly 800 relative to the patient. Connector assembly 820 can attach to a reference point such as a patient introduction device, surgical table, and/or another fixed or semi fixed point of reference. A retraction element, puller 850, releasably attaches to connector 180 of imaging probe 100, such as via a carrier 855. Retraction assembly 800 retracts at least a portion of imaging probe 100 (e.g. the portion of imaging probe 100 distal to the attached connector 180), relative to the established reference. In some embodiments, retraction assembly 800 is configured to retract at least a portion of imaging probe 100 (e.g. at least optical assembly 115 and a portion of shaft 120) at a rate of between 5 mm/sec and 100 mm/sec, such as 60 mm/sec. In some embodiments, retraction assembly 800 is configured to retract at least a portion of imaging probe 100 at a rate of at least 60 mm/sec, at least 80 mm/sec, at least 100 mm/sec, and/or at least 150 mm/sec. Additionally or alternatively, the pullback procedure can be performed during a time period of between 0.5 sec and 25 sec, for example approximately 20 sec (e.g. over a distance of 100 mm at 5 mm/sec). Service loop 185 of imaging probe 100 can be positioned between retraction assembly 800 and/or at least connector assembly 820, and rotation assembly 500, such that imaging probe 100 can be retracted relative to the patient while rotation assembly 500 remains stationary (e.g. attached to the surgical table and/or to a portion of console 50).

Retraction assembly 800 further comprises a linear drive, motive element 830. In some embodiments, motive element 830 can comprise a linear actuator, a worm drive operably attached to a motor, a pulley system, and/or other linear force transfer mechanisms. Puller 850 can be operably attached to motive element 830 via a linkage assembly 890. In some embodiments, linkage assembly 890 can comprise one or more components of a "pullback assembly", as described in reference to FIGS. 1A and 2A. Alternatively or additionally, linkage assembly 890 can comprise one or more components of an enclosed pullback connector, as described in reference to FIG. 1B. One or more components of linkage assembly 890 can establish a frame of reference (e.g. an internal pullback reference) between puller 850 and the motive element 830, such that motive element 830 applies a pullback force to puller 850 via linkage assembly 890, and puller 850 retracts relative to the distal portion of linkage assembly 890 (e.g. relative to the distal end of sheath 895 as described in reference to FIG. 1A). In some embodiments, the distal end of linkage assembly 890 and connector assembly 820 are fixed relative to each other, and puller 850 translates linearly between the two in reaction to a force applied from motive element 830.

Console 50 comprises an imaging assembly 300, a user interface 55, processor 52, and one or more algorithms 51. Processor 52 can include one or more memory storage components, such as one or more memory circuits which store software routines, algorithms (e.g. algorithm 51), and other operating instructions of system 10, as well as data acquired by imaging probe 100, second imaging device 15, and/or another component of system 10. Imaging assembly 300 can be configured to provide light to optical assembly 115 (e.g. via optical core 110) and collect light from optical assembly 115 (e.g. via optical core 110). Imaging assembly 300 can include a light source 310. Light source 310 can comprise one or more light sources, such as one or more light sources configured to provide one or more wavelengths of light to optical assembly 115 via optical core 110. Light source 310 is configured to provide light to optical assembly 115 (via optical core 110) such that image data can be collected comprising cross-sectional, longitudinal and/or volumetric information related to a patient site or implanted device being imaged. Light source 310 can be configured to provide light such that the image data collected includes characteristics of tissue within the patient site being imaged, such as to quantify, qualify or otherwise provide information related to a patient disease or disorder present within the patient site being imaged. Light source 310 can be configured to deliver broadband light and have a center wavelength in the range from 350 nm to 2500 nm, from 800 nm to 1700 nm, from 1280 nm to 1310 nm, or approximately 1300 nm (e.g. light delivered with a sweep range from 1250 nm to 1350 nm). Light source 310 can comprise a sweep rate of at least 50 KHz. In some embodiments, light source 310 comprises a sweep rate of at least 100 KHz, such as at least 200 Khz, 300 KHz, 400 KHz, and/or 500 KHz. These faster sweep rates provide numerous advantages, such as to provide a higher frame rate, as well as being compatible with rapid pullback and rotation rates. For example, the higher sweep rate enables the requisite sampling density (e.g. the amount of luminal surface area swept by the rotating beam) to be achieved in a shorter time, advantageous in most situations and especially advantageous when there is relative motion between the probe and the surface/tissue being imaged such as arteries in a beating heart. Light source 310 bandwidth can be selected to achieve a desired resolution, which can vary according to the needs of the intended use of imaging system 10. In some embodiments, bandwidths are about 5% to 15% of the center wavelength, which allows resolutions of between 20 μm and 5 μm. Light source 310 can be configured to deliver light at a power level meeting ANSI Class 1 ("eye safe") limits, though higher power levels can be employed. In some embodiments, light source 310 delivers light in the 1.3 μm band at a power level of approximately 20 mW. Tissue light scattering is reduced as the center wavelength of delivered light increases, however water absorption increases. Light source 310 can deliver light at a wavelength approximating 1300 nm to balance these two effects. Light source 310 can be configured to deliver shorter wavelength light (e.g. approximately 800 nm light) to traverse patient sites to be imaged including large amounts of fluid. Alternatively or additionally, light source 310 can be configured to deliver longer wavelengths of light (e.g. approximately 1700 nm light), such as to reduce a high level of scattering within a patient site to be imaged. In some embodiments, light source 310 comprises a tunable light source (e.g. light source 310 emits a single wavelength that changes repetitively over time), and/or a broad-band light source. Light source 310 can comprise a single spatial mode light source or a multimode light source (e.g. a multimode light source with spatial filtering).

Light source 310 can comprise a relatively long effective coherence length, such as a coherence length of greater than 10 mm, such as a length of at least 50 mm, at all frequencies within the bandwidth of the light source. This coherence length capability enables longer effective scan ranges to be achieved by system 10, as the light returning from distant objects to be imaged (e.g. tissue) must remain in phase coherence with the returning reference light, in order to produce detectable interference fringes. In the case of a swept-source laser, the instantaneous linewidth is very narrow (i.e. as the laser is sweeping, it is outputting a very narrow frequency band that changes at the sweep rate). Similarly, in the case of a broad-bandwidth source, the detector arrangement must be able to select very narrow linewidths from the spectrum of the source. The coherence length scales inversely with the linewidth. Longer scan ranges enable larger or more distant objects to be imaged (e.g. more distal tissue to be imaged). Current systems have lower coherence length, which correlates to reduced image capture range as well as artifacts (ghosts) that arise from objects outside the effective scan range.

Console 50 can comprise one or more algorithms, such as algorithm 51 shown, which can be configured to adjust (e.g. automatically and/or semi-automatically adjust) one or more operational parameters of imaging system 10, such as an operational parameter of console 50, imaging probe 100 and/or a delivery catheter 80. Console 50 can further comprise a processing assembly, processor 52, configured to execute algorithm 51, and/or perform any type of data processing, such as digital signal processing, described in reference to FIG. 4. Additionally or alternatively, algorithm 51 can be configured to adjust an operational parameter of a separate device, such as injector 20 or implant delivery device 30 described herein. In some embodiments, algorithm 51 is configured to adjust an operational parameter based on one or more sensor signals, such as a sensor signal provided by a sensor-based functional element of the present inventive concepts as described herein. Algorithm 51 can be configured to adjust an operational parameter selected from the group consisting of: a rotational parameter such as rotational velocity of optical core 110 and/or optical assembly 115; a retraction parameter of shaft 120 and/or optical assembly 115 such as retraction velocity, distance, start position, end position and/or retraction initiation timing (e.g. when retraction is initiated); a position parameter such as position of optical assembly 115; a line spacing parameter such as lines per frame; an image display parameter such as a scaling of display size to vessel diameter; an imaging probe 100 configuration parameter; an injectate 21 parameter such as a saline to contrast ratio configured to determine an appropriate index of refraction; a light source 310 parameter such as power delivered and/or frequency of light delivered; and combinations of one or more of these. In some embodiments, algorithm 51 is configured to adjust a retraction parameter such as a parameter triggering the initiation of the pullback, such as a pullback that is initiated based on a parameter selected from the group consisting of: lumen flushing (the lumen proximate optical assembly 115 has been sufficiently cleared of blood or other matter that would interfere with image creation); an indicator signal is received from injector 20 (e.g. a signal indicating sufficient flushing fluid has been delivered); a change in image data collected (e.g. a change in an image is detected, based on the image data collected, that correlates to proper evacuation of blood from around optical assembly 115); and combinations of one or more of these. In some embodiments, algorithm 51 is configured to adjust an imaging system 10 configuration parameter related to imaging probe 100, such as when algorithm 51 identifies (e.g. automatically identifies via an RF or other embedded ID) the attached imaging probe 100 and adjusts an imaging system 10 parameter, such as an arm path length parameter, a dispersion parameter, and/or other parameter as listed above.

Imaging system 10 can comprise one or more interconnect cables, bus 58 shown. Bus 58 can operably connect rotation assembly 500 to console 50, retraction assembly 800 to console 50, and or rotation assembly 500 to retraction assembly 800. Bus 58 can comprise one or more optical transmission fibers, electrical transmission cables, fluid conduits, and combinations of one or more of these. In some embodiments, bus 58 comprises at least an optical transmission fiber that optically couples rotary joint 550 to imaging assembly 300 of console 50. Additionally or alternatively, bus 58 comprises at least power and/or data transmission cables that transfer power and/or motive information to one or more of motive elements 530 and 830.

Second imaging device 15 can comprise an imaging device such as one or more imaging devices selected from the group consisting of: an X-ray; a fluoroscope such as a single plane or biplane fluoroscope; a CT Scanner; an MRI; a PET Scanner; an ultrasound imager; and combinations of one or more of these. In some embodiments, second imaging device 15 comprises a device configured to perform rotational angiography.

Treatment device 16 can comprise an occlusion treatment or other treatment device selected from the group consisting of: a balloon catheter constructed and arranged to dilate a stenosis or other narrowing of a blood vessel; a drug eluting balloon; an aspiration catheter; a sonolysis device; an atherectomy device; a thrombus removal device such as a stent retriever device; a Trevo™ stentriever; a Solitaire™ stentriever; a Revive™ stentriever; an Eric™ stentriever; a Lazarus™ stentriever; a stent delivery catheter; a microbraid implant; an embolization system; a WEB™ embolization system; a Luna™ embolization system; a Medina™ embolization system; and combinations of one or more of these. In some embodiments, imaging probe 100 is configured to collect data related to treatment device 16 (e.g. treatment device 16 location, orientation and/or other configuration data), after treatment device 16 has been inserted into the patient.

Injector 20 can comprise a power injector, syringe pump, peristaltic pump or other fluid delivery device configured to inject a contrast agent, such as radiopaque contrast, and/or other fluids. In some embodiments, injector 20 is configured to deliver contrast and/or other fluid (e.g. contrast, saline and/or Dextran). In some embodiments, injector 20 delivers fluid in a flushing procedure as described herein. In some embodiments, injector 20 delivers contrast or other fluid through a delivery catheter 80 with an ID of between 5Fr and 9Fr, a delivery catheter 80 with an ID of between 0.53" to 0.70", or a delivery catheter 80 with an ID between 0.0165" and 0.027". In some embodiments, contrast or other fluid is delivered through a delivery catheter as small as 4Fr (e.g. for distal injections). In some embodiments, injector 20 delivers contrast and/or other fluid through the lumen of one or more delivery catheters 80, while one or more smaller delivery catheters 80 also reside within the lumen. In some embodiments, injector 20 is configured to deliver two dissimilar fluids simultaneously and/or sequentially, such as a first fluid delivered from a first reservoir and comprising a first concentration of contrast, and a second fluid from a second reservoir and comprising less or no contrast.

Injectate 21 can comprise fluid selected from the group consisting of: optically transparent material; saline; visualizable material; contrast; Dextran; an ultrasonically reflective material; a magnetic material; and combinations thereof. Injectate 21 can comprise contrast and saline. Injectate 21 can comprise at least 20% contrast. During collection of image data, a flushing procedure can be performed, such as by delivering one or more fluids, injectate 21 (e.g. as propelled by injector 20 or other fluid delivery device), to remove blood or other somewhat opaque material (hereinafter non-transparent material) proximate optical assembly 115 (e.g. to remove non-transparent material between optical assembly 115 and a delivery catheter and/or non-transparent material between optical assembly 115 and a vessel wall), such as to allow light distributed from optical assembly 115 to reach and reflectively return from all tissue and other objects to be imaged. In these flushing embodiments, injectate 21 can comprise an optically transparent material, such as saline. Injectate 21 can comprise one or more visualizable materials, as described herein.

As an alternative or in addition to its use in a flushing procedure, injectate 21 can comprise material configured to be viewed by second imaging device 15, such as when injectate 21 comprises a contrast material configured to be viewed by a second imaging device 15 comprising a fluoroscope or other X-ray device; an ultrasonically reflective material configured to be viewed by a second imaging device 15 comprising an ultrasound imager; and/or a magnetic material configured to be viewed by a second imaging device 15 comprising an MRI.

Implant 31 can comprise an implant (e.g. a temporary or chronic implant) for treating one or more of a vascular occlusion or an aneurysm. In some embodiments, implant 31 comprises one or more implants selected from the group consisting of: a flow diverter; a Pipeline™ flow diverter; a Surpass™ flow diverter; an embolization coil; a stent; a Wingspan™ stent; a covered stent; an aneurysm treatment implant; and combinations of one or more of these.

Implant delivery device 30 can comprise a catheter or other tool used to deliver implant 31, such as when implant 31 comprises a self-expanding or balloon expandable portion. In some embodiments, imaging system 10 comprises imaging probe 100, one or more implants 31 and/or one or more implant delivery devices 30. In some embodiments, imaging probe 100 is configured to collect data related to implant 31 and/or implant delivery device 30 (e.g. implant 31 and/or implant delivery device 30 anatomical location, orientation and/or other configuration data), after implant 31 and/or implant delivery device 30 has been inserted into the patient.

In some embodiments, one or more system components, such as console 50, delivery catheter 80, imaging probe 100, rotation assembly 500, retraction assembly 800, treatment device 16, injector 20, and/or implant delivery device 30, further comprise one or more functional elements ("functional element" herein), such as functional elements 59, 89, 199, 599, 899, 99a, 99b, and/or 99c, respectively, shown. Each functional element can comprise at least two functional elements. Each functional element can comprise one or more elements selected from the group consisting of: sensor; transducer; and combinations thereof. The functional element can comprise a sensor configured to produce a signal. The functional element can comprise a sensor selected from the group consisting of: a physiologic sensor; a pressure sensor; a strain gauge; a position sensor; a GPS sensor; an accelerometer; a temperature sensor; a magnetic sensor; a chemical sensor; a biochemical sensor; a protein sensor; a flow sensor such as an ultrasonic flow sensor; a gas detecting sensor such as an ultrasonic bubble detector; a sound sensor such as an ultrasound sensor; and combinations thereof. The sensor can comprise a physiologic sensor selected from the group consisting of: a pressure sensor such as a blood pressure sensor; a blood gas sensor; a flow sensor such as a blood flow sensor; a temperature sensor such as a blood or other tissue temperature sensor; and combinations thereof. The sensor can comprise a position sensor configured to produce a signal related to a vessel path geometry (e.g. a 2D or 3D vessel path geometry). The sensor can comprise a magnetic sensor. The sensor can comprise a flow sensor. The system can further comprise an algorithm configured to process the signal produced by the sensor-based functional element. Each functional element can comprise one or more transducers. Each functional element can comprise one or more transducers selected from the group consisting of: a heating element such as a heating element configured to deliver sufficient heat to ablate tissue; a cooling element such as a cooling element configured to deliver cryogenic energy to ablate tissue; a sound transducer such as an ultrasound transducer; a vibrational transducer; and combinations thereof.

In some embodiments, imaging probe 100 comprises a fluid propulsion element and/or a fluid pressurization element ("fluid pressurization element" herein), not shown but such as FPE $1500_S$ described in reference to FIGS. 12 and 12A-C. A fluid propulsion element can be configured to prevent and/or reduce the presence of bubbles within gel 118 proximate optical assembly 115. The fluid propulsion element can be fixedly attached to optical core 110, wherein rotation of optical core 110 in turn rotates the fluid propulsion element, such as to generate a pressure increase within gel 118 that is configured to reduce presences of bubbles from locations proximate optical assembly 115. Such one or more fluid pressurization elements can reduce the likelihood of bubble formation within gel 118, reduce the size of bubbles within gel 118, and/or move any bubbles formed within gel 118 away from a location that would adversely impact the collecting of image data by optical assembly 115 (e.g. move bubbles away from optical assembly 115). In some embodiments, a fluid propulsion element of imaging probe 100 comprises a similar construction and arrangement to a fluid propulsion element described in applicant's co-pending U.S. Provisional Patent Application Ser. No. 62/840,450, titled "Imaging Probe with Fluid Pressurization Element", filed Apr. 30, 2019, the content of which is incorporated herein by reference in its entirety for all purposes.

Figure 1A:
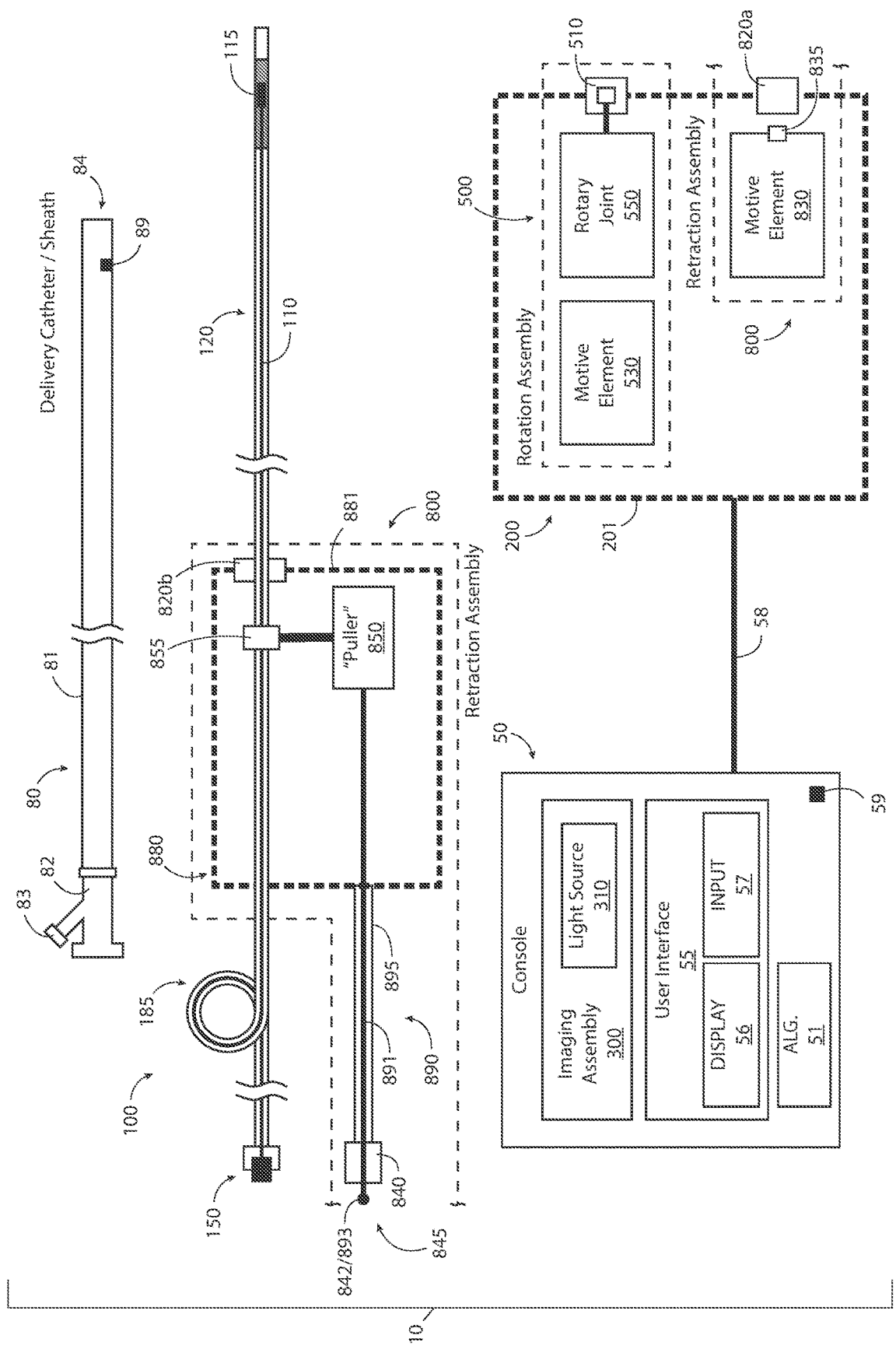
FIG. 1A illustrates a schematic view of an imaging system comprising an imaging probe operably attachable to a patient interface module, and an independent pullback module operably attachable to the patient interface module and the imaging probe, consistent with the present inventive concepts.

Referring now to FIG. 1A, a schematic view of an imaging system is illustrated, the system comprising an imaging probe operably attachable to a patient interface module, and an independent pullback module operably attachable to the patient interface module and the imaging probe, consistent with the present inventive concepts. Imaging system 10 can comprise a patient interface module 200. Patient interface module 200 comprises a housing, housing 201, surrounding at least a portion of rotation assembly 500, and at least a portion of retraction assembly 800. Imaging system 10 can further comprise a second, discrete component, pullback module 880. Pullback module 880 comprises a housing, housing 881, surrounding at least a portion of retraction assembly 800. Pullback module 880 and patient interface module 200 can be operably attached to each other via a connector assembly, linkage assembly 890 described herein. Pullback module 880 and patient interface module 200 can be constructed and arranged (via each having a separate housing) to enable positioning at different locations (e.g. linkage assembly 890 connecting modules 880 and 200 can comprise a length of at least 15 cm such that the two remote locations can be at least 15 cm apart), for example patient interface module 200 can be positioned on or near a surgical bed rail, and pullback module 880 can be positioned near a vascular access site of the patient (e.g. within 30 cm of the vascular access site thru which imaging probe 100 enters the patient). Linkage assembly 890 can comprise a linkage 891 slidingly received within sheath 895. Linkage 891 is operably attached to puller 850, and the proximal end 893 of linkage 891 can comprise a connection point, 842. Motive element 830 can comprise a connector 835 configured to releasably attach to connection point 842. Components shown in FIG. 1A can be of similar construction and arrangement to like components described in reference to FIG. 1, and as described elsewhere herein.

Figure 2A:
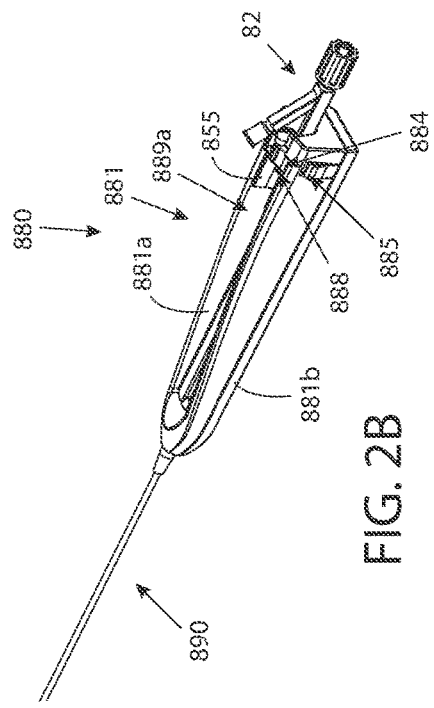
FIG. 2A illustrates a perspective view of connectors being attached to a patient interface module, consistent with the present inventive concepts.
Figure 2B:
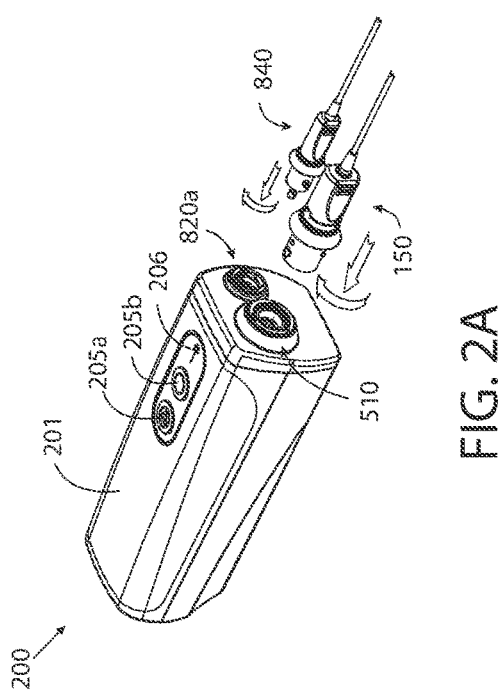
FIG. 2B illustrates a perspective view of a pullback housing, consistent with the present inventive concepts.

Pullback module 880 can comprise a connector assembly 820b that operably attaches to connector 82 of delivery catheter 80, such as described in reference to FIG. 2B. Connector assembly 845 can comprise a connector 840 that operably attaches to a connector assembly 820a of patient interface module 200, as described in reference to FIG. 2A.

Figure 1B:
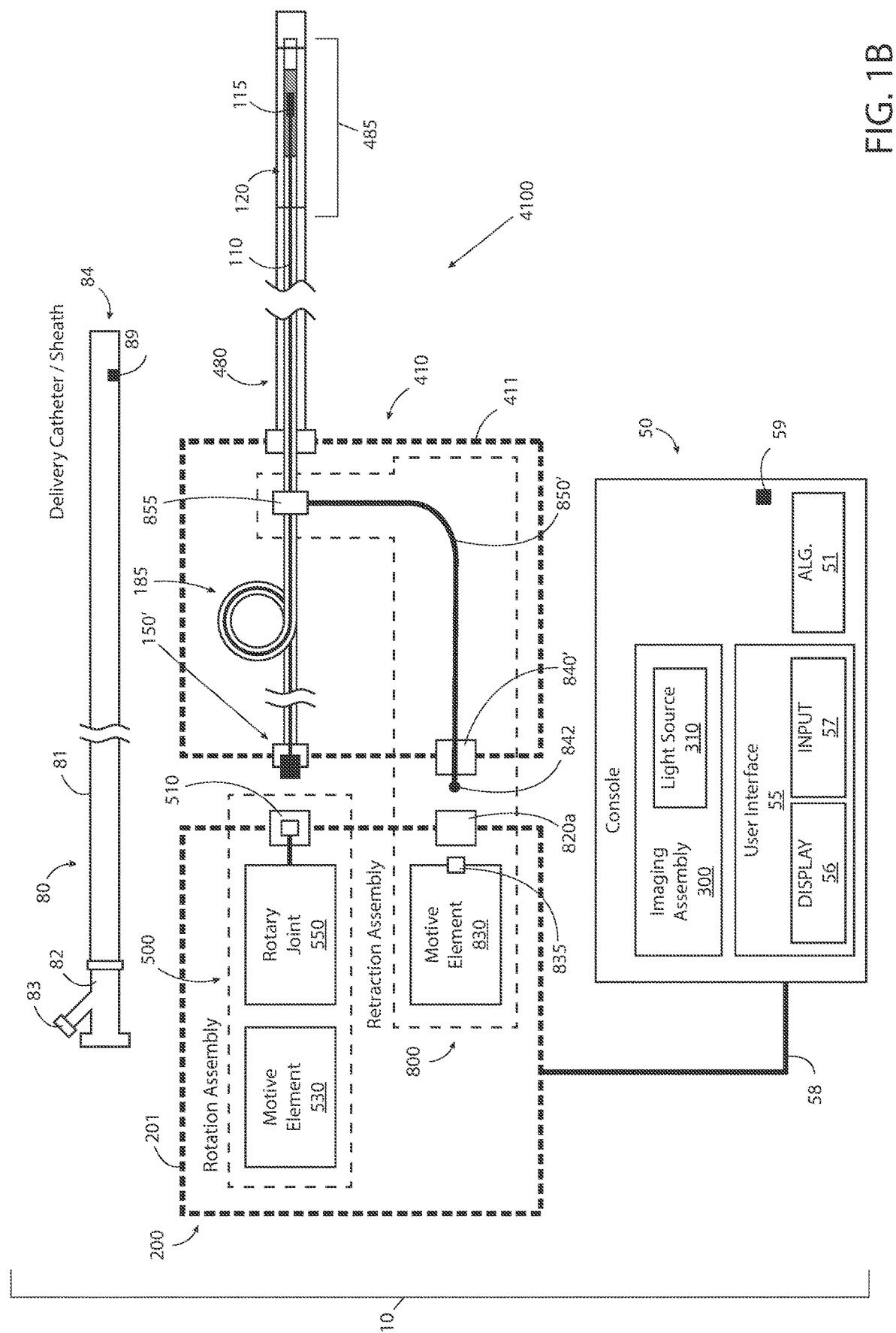
FIG. 1B illustrates a schematic view of an imaging system comprising an imaging probe operably attachable to a module comprising a first connector for attaching to a rotation motive element and a second connector for attaching to a retraction motive element, consistent with the present inventive concepts.

Referring now to FIG. 1B, a schematic view of an imaging system is illustrated, the system comprising an imaging probe operably attachable to a module comprising a first connector for attaching to a rotation motive element and a second connector for attaching to a retraction motive element, consistent with the present inventive concepts. Imaging system 10 can comprise a patient interface module 200 as described herein. Imaging system 10 can further comprise a connector module, module 410. Module 410 comprises a housing, housing 411, surrounding at least a portion of retraction assembly 800, service loop 185 of imaging probe 100, connector assembly 150', and connector 840'. Module 410 can be configured to operably attach both imaging probe 100 and a linkage, puller 850', to patient interface module 200. Components shown in FIG. 1B can be of similar construction and arrangement to like components described in reference to FIG. 1, and as described elsewhere herein. Module 410 can be operably attached to a delivery catheter 480. Delivery catheter 480 can be of similar construction and arrangement to delivery catheter 80 described in reference to FIG. 1. Delivery catheter 480 can comprise at least a portion that is optically transparent, window 485. Window 485 can be positioned at or near a distal portion of delivery catheter 480. Window 485 can comprise a material transparent to imaging modalities utilized by imaging probe 100, such that imaging probe 100 can image through window 485, for example when optical assembly 115 is retracted within window 485. In some embodiments, module 410, delivery catheter 480, and imaging probe 100 collectively form catheter assembly 4100.

Referring now to FIG. 2A, a perspective view of connectors being attached to a patient interface is illustrated, consistent with the present inventive concepts. Patient interface module 200 is configured to provide rotation to a rotatable optical core of an imaging probe, and to provide a motive force to translate at least a portion of the imaging probe, such as is described herein. Patient interface module 200 comprises rotation assembly 500, and at least a portion of retraction assembly 800. A housing 201 surrounds patient interface module 200. Patient interface module 200 can comprise one or more user interface elements, such as one or more inputs, buttons 205a,b, and one or more outputs, indicator 206 shown. Patient interface module 200 comprises a first physical connector assembly, connector assembly 510, for operably connecting to connector assembly 150 as described herein. Patient interface module 200 can further comprise a second physical connector assembly, connector assembly 820a, for operably connecting to connector 840 also as described herein. Connector assembly 150 and connector 840 can each comprise bayonet type connectors, constructed and arranged to be at least partially inserted into connector assemblies 510 and 820a, respectively. Connector assembly 150 and connector 840 can be subsequently rotated (e.g. an approximately 450 rotation) to lock their connections with connector assemblies 510 and 820a, respectively, as described herein. Connector assembly 150 and/or 840 can comprise numerous forms of connectors, such as a bayonet or other locking connectors.

Referring now to FIG. 2B, a perspective view of a pullback assembly is illustrated, consistent with the present inventive concepts. Pullback module 880 can be operably attached to a portion of an imaging probe 100 of the present inventive concepts, and provide a retraction force to the probe, pulling at least a portion of the probe proximally relative to a patient (e.g. relative to a patient introduction device), as described herein. Pullback module 880 can comprise a construction and arrangement similar to pullback module 880 as described in applicant's co-pending International PCT Patent Application Serial Number PCT/US2018/062766, titled "Imaging System", filed Nov. 28, 2018, the content of which is incorporated herein by reference in its entirety. Pullback module 880 can be operably attached to the distal end of a linkage 891 (not shown). Linkage assembly 890 can be slidingly received through pullback module 880. Sheath 895 can be fixedly attached to the proximal end of module 880. Linkage 891 is slidingly received along the length of module 880 and is operably attached at its distal end to puller 850.

Pullback module 880 can comprise a two-part housing 881, including a top housing 881a and bottom housing 881b. Module 880 can contain a translating cart, puller 850 (not shown, but positioned below carrier 855, and as described herein). Puller 850 can be designed to translate within module 880. Module 880 can comprise a biasing element, spring 852 (not shown). Spring 852 can provide a biasing force to puller 850, such as to bias puller 850 distally.

Top housing 881a can comprise a first cavity, retention port 884 and a second cavity, trench 889. Retention port 884 and trench 889 can be separated by a projection, retention wall 888. Physical connector assembly 820b can comprise a retention port 884 of housing 881a, including wall 888, and a retention mechanism, clip 885. Clip 885 can be configured to releasably engage the proximal end of a delivery catheter such as sheath connector 82 of delivery catheter 80, such as when connector 82 comprises a Tuohy Borst connector. Physical connector assembly 820b can further comprise a biasing element, spring 886 (not shown). Spring 886 can provide a biasing force to maintain clip 885 in an engaged position about connector 82.

Pullback module 880 can further comprise a carrier 855. Carrier 855 can operably attach to puller 850, such as through a slot 889a in housing 881a. Carrier 855 can translate within trench 889 in response to puller 850, which translates in response to linkage 891. Carrier 855 can operably attach to a portion of imaging probe 100, such as to a pullback connector 180. Pullback connector 180 can comprise a "torquer", or other device affixed to shaft 120 of imaging probe 100. Sheath 895 of linkage assembly 890 can provide a frame of reference between connector 840 and pullback module 880, such that when the proximal end of linkage 891 is retracted relative to connector 840, the distal end of linkage 891 is retracted towards sheath 895 (i.e. towards the proximal end of pullback module 880). This relative motion transfers motive force applied at connector 840 (e.g. via motive element 830, as described herein), to puller 850. Puller 850 subsequently transfers the motive force to imaging probe 100, and imaging probe 100 is retracted relative to the patient.

In operation, imaging probe 100 can be manually (e.g. by a user) advanced through the vasculature of the patient. Pullback module 880 can be attached to the patient (e.g. to delivery catheter 80 via connector 82, when delivery catheter 80 is inserted into and in a relatively fixed position relative to the patient), and connector 180 can be operably connected to imaging probe 100, and positioned proximate delivery catheter 80 (e.g. a torquer connector 180 can be tightened to imaging probe 100 proximate delivery catheter 80). Connector 180 (not shown) can be operably positioned within carrier 855, and a motive force can be applied to the distal end of linkage 891. Carrier 855 retracts within trench 889, retracting imaging probe 100 relative to the patient. After retraction, connector 180 can be removed from carrier 855 (e.g. lifted out of), and carrier 855 and imaging probe 100 can be re-advanced independently. For example, carrier 855 can re-advance via the bias of spring 852, as the proximal end of linkage 891 is allowed to advance, and imaging probe 100 can be re-advanced manually by a user. Subsequent retractions can be performed by repositioning connector 180 in carrier 855 after both have been re-advanced. Carrier 855 can comprise a capturing portion, such as a "cup-like" geometry, a hook, or other capture-enabling portion, such that carrier 855 can only impart a retraction force on connector 180. In this configuration, if carrier 855 were to translate distally, connector 180 would automatically disengage from carrier 855 (e.g. connector 180 would fall out of the cup portion of carrier 855).

Figure 3:
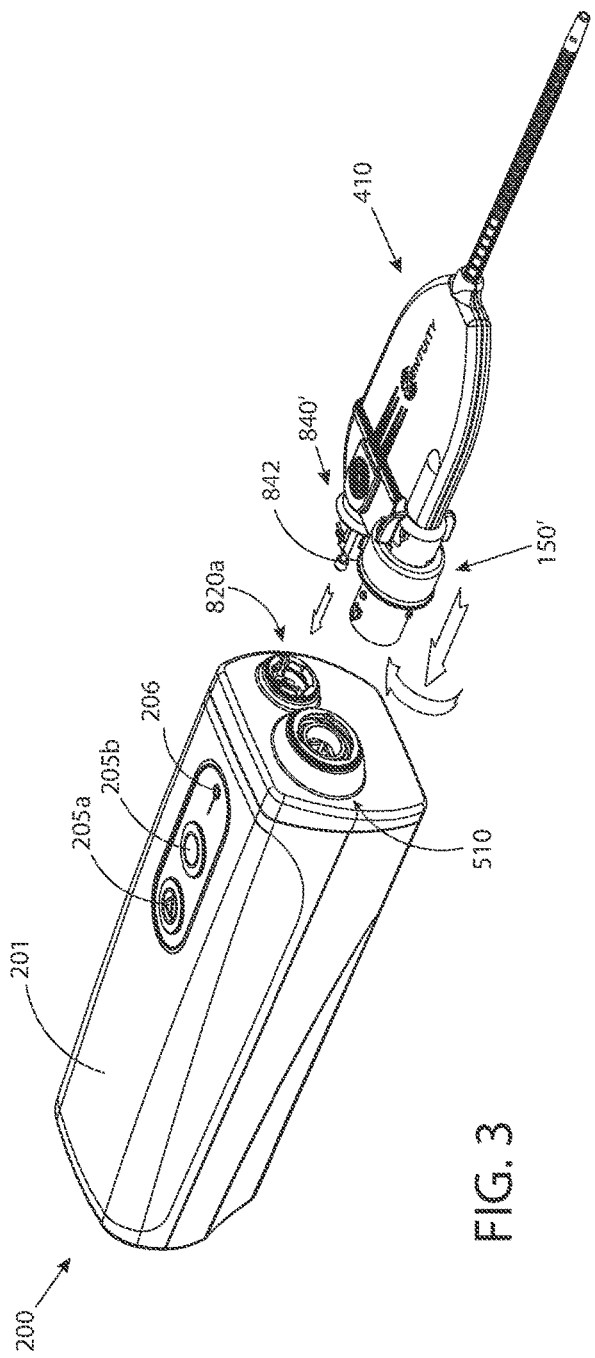
FIG. 3 illustrates a perspective view of connectors being attached to a patient interface module, consistent with the present inventive concepts.

Referring now to FIG. 3, a perspective view of connectors being attached to a patient interface module is illustrated, consistent with the present inventive concepts. Patient interface module 200 can be of similar construction and arrangement to patient interface module 200 as described in reference to FIG. 2A. Patient interface module 200 comprises a first physical connector assembly, connector assembly 510, for operably connecting to connector assembly 150'. Patient interface module 200 can further comprise a second physical connector assembly, connector assembly 820a, for operably connecting to connector 840'. Connector assembly 150' and connector 840' can each comprise bayonet type connectors, constructed and arranged to be at least partially inserted into connector assemblies 510 and 820*a*, respectively.

As described herein, system 10 can be constructed and arranged to provide improved imaging of a patient's anatomy (e.g. of one or more blood vessels of the patient) as well as improved imaging of implants, catheters, and/or other devices positioned in the patient (e.g. positioned in a blood vessel of the patient). In some embodiments, system 10 is configured to provide information that is used (e.g. by a clinician) to perform a treatment (e.g. an intervention), wherein the information is based on, at least, optical coherence tomography data. For example, OCT and other data gathered by system 10, can be used to plan a treatment and/or predict a treatment outcome (e.g. the planning and/or predicting performed by system 10, a user of system 10, or a combination of the two), such as to impact a treatment to be delivered to the patient ("OCT-guided treatment" and/or "OCT-guided therapy" herein).

As described herein, imaging probe 100 can comprise at least one of: size (e.g. diameter and/or length), scan range, flexibility, and/or imaging capability configured to provide the improved imaging. Imaging probe 100 can comprise a size and/or flexibility configured to enable imaging of tight lesions within the vessel. As used herein, a tight lesion can comprise a lesion whose resultant lumen (i.e. the lumen within the lesion) comprises a diameter (e.g. the smallest diameter along the length of the lesion) of less than 2 mm (0.080"). A commercially available OCT catheter positioned to image a lesion with a lumen of this small diameter would effectively block the proximally-applied flush media from propagating to locations distal to the lesion, preventing the use of this commercial device. However, imaging probe 100 can be constructed and arranged to image these tight lesions, for example lesions with a resultant lumen as small as 1.5 mm (0.060"), as low as 1.3 mm (0.053"), 1.1 mm (0.043"), and/or as low as 0.9 mm (0.036") can be imaged by imaging probe 100. For example, the distal portion of imaging probe 100 can comprise an outer diameter of no more than 2.6F (0.034"), such as an outer diameter of no more than 1.7F (0.022"), such as to enable system 10 to be used to image potential vessels (e.g. arteries) to be treated that have a tight lesion, such as when the distal portion of imaging probe 100 is inserted into and through a stenosis, such as in a "pre-treatment" imaging procedure (e.g. a procedure performed prior to intervention or other treatment of the stenosis). As described herein, currently available OCT imaging systems can be too large to provide useful data (e.g. unable to pass thru and/or provide sufficient blood clearing in a tight lesion). Other types of imaging systems, such as angiography, may not provide sufficiently accurate results when imaging tight lesions (e.g. erroneously indicate no treatment is warranted, such as when providing FFR information). In some embodiments, system 10 is used to perform a pre-treatment imaging procedure (e.g. of a tight lesion) to gather data to enable OCT-guided treatment in which the data provided by system 10 (e.g. using images from at least probe 100) is used by an operator (e.g. a clinician) to make decisions about a future treatment to be performed. In these embodiments, system 10 can also be used to image a similar anatomical location, after the treatment has been performed (in a "post-treatment" imaging procedure).

In some embodiments, system 10 is configured to perform a pre-treatment imaging procedure (e.g. of a tight lesion or otherwise) and provide OCT-guided treatment due to the following characteristics of system 10: distal portion of probe 100 (e.g. including optical assembly 115) comprises a diameter of less than 2.6Fr (0.034"), such as a diameter of no more than 2.0Fr (0.026"), such as a diameter of no more than 1.7Fr (0.022")

In some embodiments, system 10 is configured to perform a pre-treatment imaging procedure (e.g. of a tight lesion or otherwise) and provide OCT-guided treatment due to the following characteristics of system 10: optical assembly 115 is rotated (e.g. via rotation assembly 500) at a rate of more than 180 rotations per second, such as a rate of at least 200, 250, 400, and/or 500 rotations per second.

In some embodiments, system 10 is configured to perform a pre-treatment imaging procedure (e.g. of a tight lesion or otherwise) and provide OCT-guided treatment due to the following characteristics of system 10: scan range of system 10 is at least a radius of 7 mm, such as a radius of at least 11 mm. The long scan range of system 10 provides numerous advantages, such as the ability to image from the imaged vessel into any side branches of that vessel, the ability to image large vessels when optical assembly 115 is eccentrically positioned within the vessel lumen (e.g. proximate a portion of the vessel wall), and/or the ability to image larger vessels in general, such as the left main artery, carotid arteries, and large peripheral arteries.

In some embodiments, system 10 is configured to perform a pre-treatment imaging procedure (e.g. of a tight lesion or otherwise) and provide OCT-guided treatment due to the following characteristics of system 10: pullback distance of more than 7.5 cm, such as a pullback of at least 10 cm, or at least 15 cm. The pullback can be performed at a rate of at least 25 mm/sec, and/or within a time period of no more than 4 seconds (e.g. a complete pullback of at least 7.5 cm, 10 cm, and/or 15 cm in no more than 4 seconds). The operable pullback speed of imaging probe 100 can be determined via a relationship between the rotation rate of optical assembly 115 and the desired frame density (e.g. frames/mm) of the OCT image data, such that the pullback speed comprises the rotation rate divided by the frame density. Imaging probe 100 can comprise a rotation rate of greater than 180 Hz, such as at least 200 Hz or at least 250 Hz. Imaging probe 100 can comprise a frame spacing of no more than 0.2 mm (i.e. a frame density of at least 5 frames/mm). Imaging probe 100 can comprise a laser scan frequency of at least 200 KHz.

In some embodiments, system 10 is configured to perform a pre-treatment imaging procedure (e.g. of a tight lesion or otherwise) and provide OCT-guided treatment due to the following characteristics of system 10: pullback speed (the translation rate of optical assembly 115 during a pullback) of at least 50 mm/s. In these embodiments, rotation rate of optical assembly 115 can be at least 180 Hz, 200 Hz, and/or 250 Hz. In these embodiments, the frame spacing can be 0.2 mm minimum.

In some embodiments, system 10 is configured to perform a pre-treatment imaging procedure (e.g. of a tight lesion or otherwise) and provide OCT-guided treatment due to the following characteristics of system 10: lines per frame of at least 400, such as at least 800 lines/frame, where a frame comprises approximately 3600 of continuous image data (i.e. one full rotation of optical assembly 115 provides one frame of image data). In some embodiments, system 10 is configured to capture frames at a rate sufficient to allow down-sampling of the frames (e.g. down sampling performed prior to analog to digital conversion of the data, and/or other bandwidth-limited data processing).

In some embodiments, system 10 is configured to perform a pre-treatment imaging procedure (e.g. of a tight lesion or otherwise) and provide OCT-guided treatment due to the following characteristics of system 10: scan frequency of at least 50 kHz, such as at least 200 kHz, 350 kHz, and/or 500 kHz. In these embodiments, the lines per frame can be at least 400 lines/frame, or at least 800 lines/frame (e.g. where lines per frame equals the scan frequency divided by the rotation rate of optical assembly 115).

In some embodiments, system 10 comprises a laser scan frequency of no less than 200 kHz, a pullback speed of no less than 60 mm/sec or 100 mm/sec, and/or a rotation rate of no less than 250 Hz. System 10 can be configured to allow imaging of at least 50 mm of a vessel, such as at least 50 mm imaged in no more than 0.5 seconds, with no less than 800 scan lines per rotation, with approximately 400 µm pitch and/or a frame density of at least 2.5 frames/mm, and/or at least 5.0 frames/mm. In some embodiments, system 10 is configured to perform a pullback during a resting portion of the heart cycle to minimize motion artifacts. In some embodiments, system 10 comprises a rotation rate of up to 400 kHz, such as no less than 250 kHz, 300 kHz, or 350 kHz.

In some embodiments, system 10 is configured to perform a pre-treatment imaging procedure (e.g. of a tight lesion or otherwise) and provide OCT-guided treatment due to the following characteristics of system 10: processor 52 is configured to identify (e.g. via algorithm 51) a reflection generated at the splice interface between optical assembly 115 and optical core 110. The optical interface between optical assembly 115 (e.g. optical assembly 115 comprising a GRIN lens) and optical core 110 (e.g. optical core 110 comprising a NZDS fiber) can comprise a relatively large index mismatch, providing a clearly differentiable reflection. This reflection can provide a reference point for the OCT image data collected by system 10. In some embodiments, the interface can be identified by algorithm 51 with or without rotating optical core 110.

Figure 4:
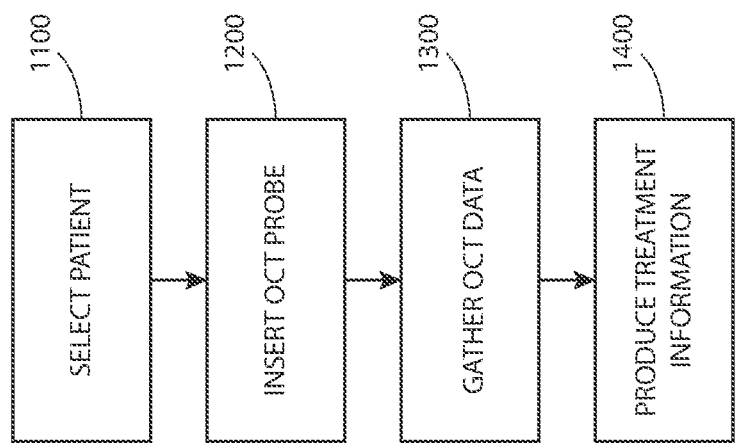
FIG. 4 illustrates a flow chart of a method of planning a treatment procedure for a patient, consistent with the present inventive concepts.

Referring now to FIG. 4, a flowchart of a method of planning a treatment procedure for a patient is illustrated, consistent with the present inventive concepts. Method 1000 of FIG. 4 is described using system 10 described in reference to FIGS. 1-3.

In Step 1100, a patient is selected for potential treatment.

In Step 1200, an OCT probe, such as imaging probe 100, is inserted into the patient.

In Step 1300, OCT data is gathered, such as is described herein. In some embodiments, non-OCT data is also gathered, such as patient physiologic data recorded by one or more physiologic sensors of system 10, and/or angiography data gathered by system 10.

In Step 1400, treatment information is produced, such as by system 10 and/or by a user of system 10 (e.g. the clinician of the patient performing the data gathering procedure of method 1000 or performing the subsequent treatment on the patient based on the treatment information produced via method 1000). In some embodiments, treatment information provided by system 10 is based on a combination of OCT data and non-OCT data.

Figure 5:
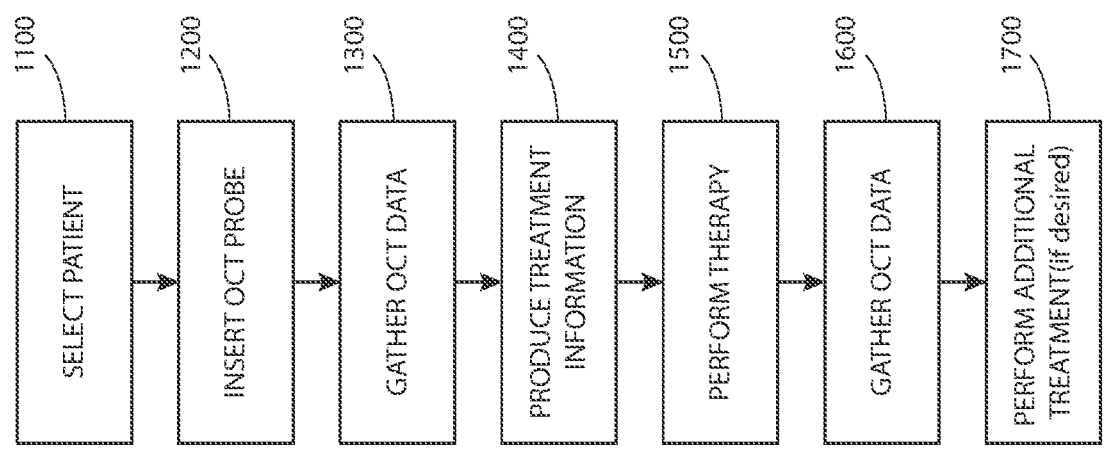
FIG. 5 illustrates a flow chart of a method of planning a treatment procedure, performing a treatment, and assessing the treatment, consistent with the present inventive concepts.

Referring now to FIG. 5, a flowchart of a method of planning a treatment procedure, performing a treatment, and assessing the treatment, is illustrated, consistent with the present inventive concepts. Method 1000 of FIG. 5 is described using system 10 described in reference to FIGS. 1-3.

In Step 1100, a patient is selected for potential treatment.

In Step 1200, an OCT probe, such as imaging probe 100, is inserted into the patient.

In Step 1300, OCT data is gathered, such as is described herein. In some embodiments, non-OCT data (e.g. at least angiographic data) is also gathered in Step 1300, such as is described herein.

In Step 1400, treatment information is produced, such as by system 10 and/or by a user of system 10 (e.g. the clinician of the patient performing the data gathering procedure of method 1000 or performing the subsequent treatment on the patient based on the treatment information produced via method 1000).

In Step 1500, a treatment procedure is performed on the patient, such as is described herein.

In Step 1600, OCT data is gathered, such as is described herein. In some embodiments, non-OCT data (e.g. at least angiographic data) is also gathered in Step 1600, such as is described herein.

In Step 1700, additional treatment can be performed, such as an additional treatment performed based on the OCT data gathered in Step 1600.

Figure 6:
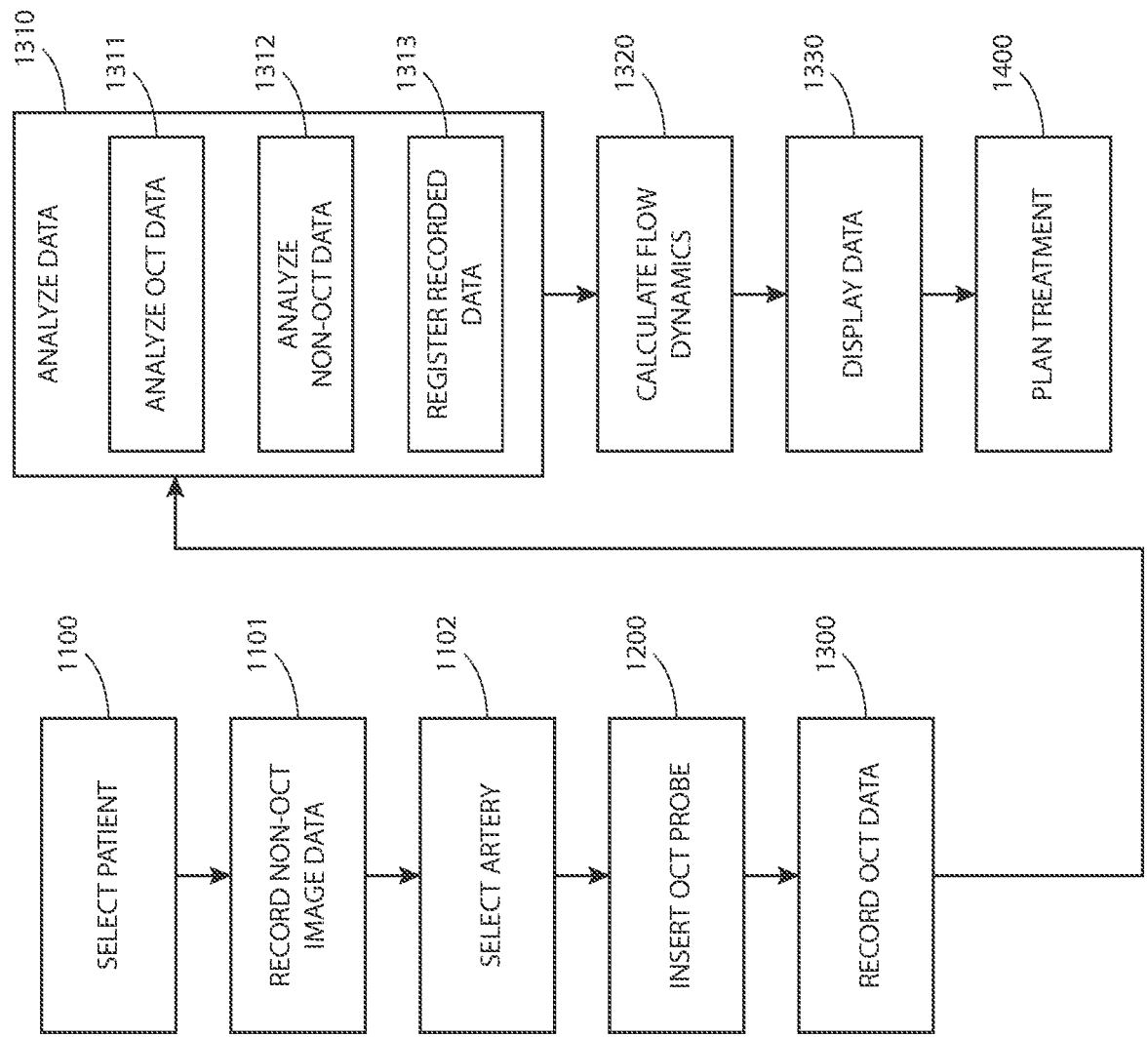
FIG. 6 illustrates a flowchart of a method of planning a treatment procedure for a patient, consistent with the present inventive concepts.

Referring now to FIG. 6, a flowchart of another method of planning a treatment procedure for a patient is illustrated, consistent with the present inventive concepts. Method 1000 of FIG. 6 is described using system 10 described in reference to FIGS. 1-3. The method of FIG. 6 is described where system 10 is used to create image data from one or more arteries of the patient's heart. It should be considered within the spirit and scope of this application that a similar method can be applied to the other blood vessels and/or other locations of the patient's anatomy (e.g. arteries and/or veins of the patient's brain or peripheral vasculature).

In Step 1100 a patient is selected. In some embodiments, the user can enter one or more patient parameters to system 10, such as via user interface 55 of console 50. The one or more patient parameters can be selected from the group consisting of: patient weight; existence of one or more patient diseases (e.g. in addition to cardiovascular disease such as diabetes if applicable); gender; age; height; TIMI score; previous coronary interventions such as stent implants, bypass grafts, and the like; and combinations of one or more of these.

In Step 1101, system 10 can be used to capture non-OCT imaging data of the selected patient, such as via second imaging device 15 described herein. As used herein, "non-OCT data" shall include but not be limited to: angiography image data; ultrasound image data; MRI image data; PET Scan image data; and/or other non-OCT imaging data. In some embodiments, non-OCT data comprises two or more of: angiography image data; ultrasound image data; MRI image data; PET Scan image data; and/or other non-OCT imaging data. In some embodiments, non-OCT data comprises angiography image data, and one or more of: ultrasound image data; MRI image data; PET Scan image data; and/or other non-OCT imaging data.

This non-OCT data can be stored in memory of system 10, such as memory of processor 52 of console 50. For example, angiography images of one or more vessels can be obtained using contrast injections, wherein the angiography data is saved in system 10 memory. Alternatively or additionally, the user may manually enter relevant patient data (e.g. data similar to and/or extracted from angiography data or other non-OCT data) into console 50 (e.g. via a keyboard or other user input component 57 of user interface 55). Step 1101 can be performed (e.g. repeated, in whole or in part) in any of the steps of the method of FIG. 6 described herein.

In Step 1102, one or more arteries, veins, and/or other conduits ("artery" or "arteries" herein) are selected for diagnosis by the user (e.g. a clinician of the patient), such as an artery which may require interventional treatment. In some embodiments, the selected vessel (e.g. a selected artery or selected vein) is manually input into system 10, such as by a user of system 10. In some embodiments, the selected vessel comprises an artery selected from the group consisting of: left circumflex (LCx); right coronary artery (RCA); left anterior descending (LAD); and combinations of one or more of these. In some embodiments, data is input into system 10 by a user during a processing step, such as Step 1310 described herein. For example, while system 10 (e.g. algorithm 51) performs one or more background calculations, system 10 can be configured to accept user input such that overall procedure time is reduced (e.g. while system 10 is processing data, the user performs required and/or other data entry).

In Step 1200, imaging probe 100 is inserted into the selected vessel (referred to herein as the "selected vessel", the "imaged vessel", the "selected artery", the "imaged artery", the "selected vein", or the "imaged vein", as appropriate). When two or more arteries are selected for diagnosis, the following steps can be repeated for each selected artery. Probe 100 placement (e.g. positioning of optical assembly 115) is performed to effectively obtain the images required for one or more various calculations to be performed by system 10 (e.g. flow calculations). The anatomical location at which pullback is to start (e.g. the position of optical assembly 115 at the start of a pullback) is selected to be a location beyond (i.e. distal to) the distal end of the distal-most diseased portion of the artery (e.g. the distal-most portion of a lesion). The location at which the pullback is to end (e.g. the position of optical assembly 115 at the end of a pullback) is selected to be a location within the most distally placed delivery catheter 80 through which imaging probe 100 is inserted (e.g. a distal portion of a delivery catheter 80).

In Step 1300, a pullback is performed in which imaging data comprising OCT data is recorded while probe 100 is retracted through the lumen of the selected artery.

In Step 1310, the OCT recorded data is analyzed. In some embodiments, both OCT data and non-OCT data (e.g. angiography data) is analyzed (e.g. OCT data is analyzed in combination with non-OCT data). Steps 1311, 1312, and/or 1313 (or portions of these) can be performed sequentially, simultaneously, and/or they can be interleaved as the recorded data is analyzed by system 10.

In Step 1311, recorded OCT data is analyzed by system 10. In some embodiments, the OCT data can be analyzed to identify one or more of the following: lumen boundaries; side branches; healthy (e.g. non-diseased) portions of lumen; diseased portions of lumen; type of disease imaged; the location of a guidewire within the image; and combinations of one or more of these. In some embodiments, the guidewire is removed from the OCT data. In some embodiments, system 10 identifies healthy sections of the imaged artery based on the OCT data. Healthy sections can be determined by identifying visible intima, media, and/or adventitia layers within the OCT data. In some embodiments, the myocardial mass can be estimated based on the diameter of one or more identified healthy sections of the imaged artery. In some embodiments, the estimate of the myocardial mass can be based on both OCT data and non-OCT data (e.g. angiography data).

System 10 can comprise a weighting function (e.g. where algorithm 51 comprises the weighting function), where the weighting function is configured to prioritize data (e.g. prioritize a data type) in one or more calculations, for example to preferentially bias a calculation based on OCT data vs non-OCT data, or vice versa. In some embodiments, system 10 (e.g. via algorithm 51) identifies the presence of disease proximate one or more side branches of an imaged artery. For example, if disease is detected proximate a side branch (e.g. disease is detected inside the side branch), the weighting function can be configured to prioritize angiography data related to the diseased side branch (e.g. to preferentially bias a calculation toward weighting angiography above OCT data).

System 10 can be configured to calculate (e.g. via algorithm 51) the branch angle of a side branch from the imaged artery. In some embodiments, the branch angle is used by algorithm 51 to calculate the side branch vessel diameter. System 10 can be configured to reconstruct at least a portion of the side branch from the OCT data (e.g. from the image slices of the OCT data), and/or from non-OCT data (e.g. from angiography data). In some embodiments, system 10 is configured to calculate the relationship between the side branch angle and the diameter of the size of the side branch (e.g. the size of the side branch relative to the size of the imaged artery). In these embodiments, if the relationship between branch angle and branch diameter is outside of an expected range, system 10 can be configured to "flag" this anomaly (e.g. identify the anomaly and store the associated information), and/or to alert the user of this anomaly, such as in Step 1330 described herein.

In some embodiments, system 10 is configured to identify a portion of OCT data representing the minimal lumen diameter (e.g. a portion of healthy tissue with the minimal lumen diameter). Additionally, system 10 can be configured to identify between two and five sections of the OCT data along the length of the lumen imaged during the pullback (e.g. equally spaced sections along the length of the lumen imaged). The identified sections can be used to estimate the non-diseased vessel size (e.g. lumen diameter) of the selected artery. In some embodiments, at least one of the identified sections comprises a proximal section, and at least one of the sections comprises a distal section (e.g. proximal and distal sections proximate the proximal and distal ends, respectively, of the lumen imaged). In some embodiments, the proximal and/or distal sections are within the proximal and distal 10%, respectively, of the length of the lumen imaged. In some embodiments, a weighting function is configured to apply a weight (i.e. a weighting factor) to each section based on a confidence level of the OCT data for that section. Confidence can be determined in several ways, for example the proportion of unambiguous lumen detected in a single frame (for example, at least 75% of the circumference should be unambiguous for high confidence), and/or the amount of change in lumen area from frame to frame (e.g. discontinuous frames should be given less weight). Confidence is also obtained from the deviation of circularity of the cross section of the imaged vessel.

In some embodiments, system 10 (e.g. via algorithm 51) identifies areas of disease based on OCT data and/or non-OCT data. In some embodiments, types of disease can be identified by system 10, such as when system 10 identifies plaque composition of a diseased segment of an artery.

In Step 1312, non-OCT data (e.g. angiography data) can be analyzed. In some embodiments, non-OCT data is analyzed to identify one or more of the following: vessel geometries (e.g. curves, tapers, and/or trajectories); side branch locations (e.g. the size and position of side branches of one or more main arteries to be diagnosed); vessel lengths; vessel diameters; and combinations of one or more of these. In some embodiments, the non-OCT data can be analyzed to estimate one or more of the following: myocardial mass; collateral flow; size of the heart area (myocardium) being supplied by an artery (e.g. a selected artery); and combinations of one or more of these. In some embodiments, the non-OCT data analyzed in Step 1312 comprises angiography image data and one or more of: ultrasound image data; MRI image data; PET Scan image data; and/or other non-OCT imaging data. In some embodiments, non-OCT data comprises angiography data which is converted by system 10 into QCA data. In some embodiments, non-OCT data comprises PET-scan data that system 10 converts into myocardial damage data (e.g. where system 10 adjusts vessel size in a damaged area).

In Step 1313, OCT data and Non-OCT data (e.g. angiography data) can be registered (e.g. correlated). In some embodiments, the data can be registered using the location, size, and shape of one or more side branches of the selected artery. In some embodiments, system 10 can comprise a digital model of the expected branching of one or more of the major vessels of the heart, for example the LCx, RCA, and/or LAD arteries. In some embodiments, the digital model is used by system 10 to register the data.

In Step 1320, cardiovascular flow dynamics can be calculated based on the analyzed data (e.g. the OCT data and/or Non-OCT data collected and/or analyzed). In some embodiments, system 10 is configured to estimate microvascular resistance distal to the selected artery.

In some embodiments, the measured size of the imaged artery is adjusted by system 10 (e.g. the size of the image artery as determined in step 1310 is adjusted by algorithm 51). System 10 can adjust the measured size of the imaged artery based on Murray's Law. For example, system 10 can assume constant sheer stress in all non-diseased areas of the imaged artery. This adjustment can minimize the error function of flow calculated by system 10 using Murray's Law. In some embodiments, flow calculations are adjusted using a weighting function that is based on the confidence of the analyzed data. For example, if Murray's law suggests an adjustment to the measured size and the confidence of the imaged cross section is relatively low then system 10 can be configured to adjust the flow calculations based on the Murray's law suggested adjustments. Alternatively, if the confidence is high, one or more adjustments based on Murray's law can be ignored by system 10.

The size of the myocardium being supplied can be estimated by system 10 (e.g. using algorithm 51) based on the selected artery vessel type and/or calculated size. In some embodiments, the estimated myocardial size can be compared to the estimated size calculated based on non-OCT Data (e.g. angiography data), such as described in Step 1312. In some embodiments, if the Non-OCT-based estimate and the OCT-based estimate vary, the user is alerted by system 10 (e.g. via a user display 56 or other user output component of interface 55). In some embodiments, system 10 accepts user input to adjust the estimate (e.g. via user input 57 of user interface 55). In some embodiments, the OCT-based estimate is given a higher weight (e.g. by a weighting function of system 10) than the angiography-based estimate (e.g. the OCT-based estimate is favored by system 10). In some embodiments, the data displayed in step 1330 can comprise a color map (e.g. a color map shown in display 56). In some embodiments, the color map can indicate the estimated myocardial size being supplied by a selected artery (e.g. the amount of myocardial tissue supplied by a selected artery). In some embodiments, hyperemic microvascular resistance is estimated by system 10 (e.g. via algorithm 51) for all or at least a portion of the heart outside the imaging area.

In some embodiments, the pressure throughout the vasculature of the heart (the "coronary tree") is calculated. In some embodiments, fractional flow reserve (FFR) is calculated (e.g. calculated from the lowest pressure). The FFR can be calculated for a selected artery, such as for each selected artery (e.g. each artery selected and imaged using OCT). In some embodiments, system 10 can be configured to alert the user (via user interface 55) if one or more of the following is detected: significant collateral flow is found (e.g. flow above a system 10 threshold); a myocardial estimate varies significantly (e.g. the variance is above a system 10 threshold) between an OCT-based estimate and a non-OCT-based estimate (e.g. angiography-based estimate); a TIMI score indicates compromised myocardial tissue; a region of no-flow is detected angiographically (e.g. indicating a blockage); and combinations of one or more of these.

In Step 1330, OCT data and/or non-OCT data (e.g. angiography data) is displayed (e.g. on display 56). In some embodiments, the data is shown in an overlay arrangement (e.g. OCT data is overlaid on angiography data and/or other non-OCT data), such as after the multiple sets of data have been registered in Step 1320. In some embodiments, a graph of lumen diameter is displayed. The lumen diameter can comprise the hydraulic diameter (e.g. four times the area of the lumen divided by the perimeter). In some embodiments, one or more side branches (or portions thereof) of the selected artery are displayed. In some embodiments, the user can add data (e.g. manually add data) to system 10 indicating that disease is present proximate the displayed OCT data, for example at the proximal or distal end of the lumen, or within a side branch (e.g. the user visually determines that disease is present via information provided by second imaging device 15 and manually enters associated disease type and/or disease location data into system 10). In some embodiments, calculated vessel sizes are displayed along with the OCT images and/or non-OCT images (e.g. angiography images). In some embodiments, system 10 allows the user to edit the displayed calculated values (e.g. in order to allow a user-initiated manual adjustment of a system 10 calculated value).

In Step 1400, a user of system 10 can plan a treatment procedure based on the displayed data. In some embodiments, the user indicates a length and location of a "treatment area" to be evaluated by system 10 (e.g. the user indicates the treatment area by clicking on the displayed image). In some embodiments, system 10 displays the estimated vessel diameter at the proximal and distal ends of the selected treatment area. In some embodiments, the vessel diameters are estimated by system 10 (e.g. via algorithm 51) using Green's Theorem. In some embodiments, system 10 displays one or more pieces of information related to the selected treatment area, for example any warnings associated with the treatment area and/or the plaque composition within the treatment area. In some embodiments, post-treatment flow dynamics (e.g. FFR) can be estimated assuming the planned treatment (e.g. stenting) opens the treated vessel to the estimated diameter at the proximal and distal ends of the selected treatment area (e.g. where two diameters can be used to indicate vessel tapering). In some embodiments, the post-treatment flow dynamics can be estimated based on the calculated pre-treatment flow dynamics and the proposed treatment. In some embodiments, the user can vary the proposed treatment area, and system 10 can update the flow dynamics based on the new treatment area. In some embodiments, the user can indicate two or more treatment areas (e.g. two or more non-contiguous treatment areas), and post-treatment flow dynamics can be estimated for each treatment area.

Figure 7:
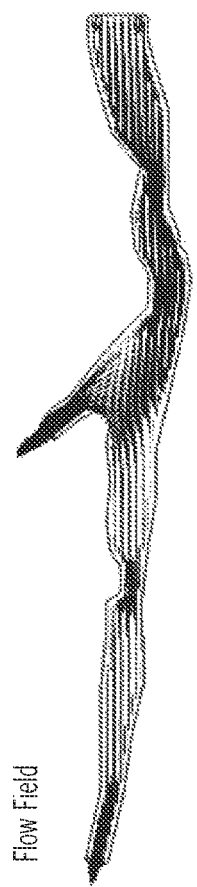
FIG. 7 illustrates a full Navier-Stokes simulation of flow through an artery, and the FFR calculated through the length of the artery, consistent with the present inventive concepts.
Figure 7:
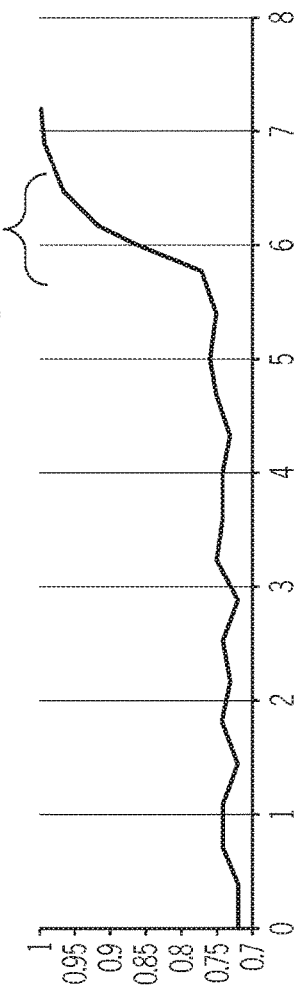

As described herein, system 10 can be configured to calculate the flow characteristics through one or more blood vessels that have been imaged using probe 100 (e.g. via one or more pullbacks). System 10 can be configured to calculate the flow dynamics (e.g. flow field and/or pressure drop) through an imaged vessel (e.g. an artery to which a treatment has been or will be performed). In some embodiments, system 10 calculates the flow and pressure drop of coronary vessels using a full 3D Navier-Stokes simulation of the vessel imaged using probe 100. As shown in FIG. 7 and described herein, system 10 can be configured to include in its analysis (e.g. via algorithm 51) numerous geometric and other features of the imaged area, such as when every significant morphological feature is represented. System 10 can directly measure the pressure in the vessel, and the FFR at the locations along the length of the vessel may be calculated, as described herein. Regions where the rapid changes in FFR occur (e.g. as identified by system 10) can be used to justify intervention (e.g. stenting).

FIG. 7 illustrates a full Navier-Stokes simulation of flow through an artery, and the FFR calculated through the length of the artery.

The use of a full 3-D Navier-Stokes equation is computationally intensive and can require a time duration that is undesirably long. In some embodiments, system 10 utilizes a two dimensional (2-D) scheme that gives results that are sufficiently accurate for the calculation of the FFR, yet require less time than a full three dimensional (3-D) Navier-Stokes-based approach.

In some embodiments, system 10 can be configured to use 3-D Navier-Stokes equations in subsets of a flow field, such as when small morphological features effect the flow. Examples of these include: bifurcation lesions with significant stenosis; locations downstream of a constriction, such as to predict the transition to turbulent flow. These short lengths of vessel can be computed relatively quickly, and the calculated flow resistance can be modeled as resistor elements in the 2-D scheme.

System 10 can be configured to utilize a 2-D scheme that uses the lumen area calculated from OCT data vs the distance and a flow shape parameter to predict pressure drop, flow separation and viscous wall forces.

For fully developed flow in pipes, the relationship between flow and pressure drop is:

$$Q = \frac{-\pi R^4}{8\mu} \frac{dP}{dx}$$

where:
Q=Volumetric flow rate
R=Radius of the pipe (one half the pipe diameter)
μ=blood viscosity
dP/dx=Pressure drop in the pipe along the pipe direction In some embodiments, in order to increase the speed of the calculations performed by system 10, μ is set to a constant (e.g. 3 centipoise), in other words the shear thinning effects of blood are ignored. For correlations to measured FFR, system 10 can be configured to adjust μ to hematocrit, but in general use it is taken as constant.

Figure 8:
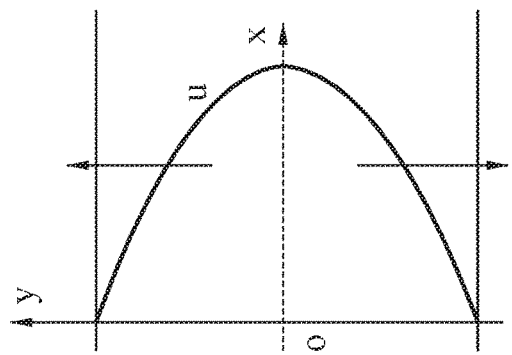
FIG. 8 illustrates a graph of a velocity profile through a pipe.

The velocity profile thru the pipe is shown in FIG. 8. The profile is parabolic, with the highest velocity at the center.

When the diameter of the vessel changes, the velocity profile will change from parabolic to some other shape. In some embodiments, system 10 utilizes a one dimensional (1-D) method, using just these two continuous parameters along the length of the vessel to calculate pressure drop, the vessel diameter and the deviation from the parabolic shape. System 10 calculates other continuous values along the length based on these two parameters. These values can include Reynolds Number, degree of turbulence, rate of pressure gradient change and wall shear stress.

Figure 9:
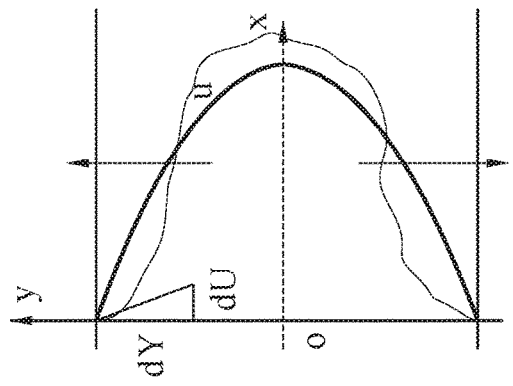
FIG. 9 illustrates the velocity and shear stress of blood near a vessel wall.

In regions where the vessel diameter is rapidly getting larger, the velocity near the walls decreases as shown in FIG. 9. The shear stress μ dU/dy (evaluated at the wall), decreases, which decreases the pressure drop component from viscosity.

In some embodiments, system 10 performs a 1-D solution comprising a fourth order, axially symmetric equation to represent the velocity:

$$U(y)=a+by+cy^2+dy^3+ey^4$$

The coefficients a, b, c, d, and e are calculated along the length from the upstream velocity profile and the rate of pressure change. The coefficients of the higher order terms (third and fourth) may be kept in bounds to keep the solution stable. This limitation greatly speeds up the calculations with minimal loss of precision.

In some embodiments, system 10 uses a 1-D method to calculate the wall shear from the shape function.

In some embodiments, system 10 uses a 2-D method to calculate shear stress directly from the velocity gradient at the wall. For example, the 2-D method can use the polar coordinate form of the Navier-Stokes equation to simplify the calculations. All low Reynolds Number terms can be used. Viscous dissipation terms can be avoided (e.g. not used). The equations are taken at steady state, thus the time dependent terms are not used. Also, gravity can be ignored as it is not significant in this single phase flow.

$$(V \cdot \nabla)V = -\nabla p + \mu \nabla^2 \vec{V}$$

Convective — Pressure gradient — Diffusion term

The pressure gradient is solved in the radial and axial directions as is the velocity equation. The continuity equation is also solved, allowing for radial flow. The radial flow velocity is insignificant and may be ignored for wall shear:

$$\nabla \cdot \vec{V}=0$$

System 10 can include any number of efficient "flow solvers". In some embodiments, system 10 includes a finite volume solver. A 2-D discretization can be performed. Smaller cells can be used in areas of rapidly changing geometry. Flow can be stepped downstream starting from parabolic flow at the inlet. The equations can be solved with an assumed pressure gradient and once the entire flow field is calculated with that pressure, system 10 then recalculates the pressure with the updated flow field. System 10 can be configured to iterate the solution until the force balance in each finite volume is converged to pre-defined tolerance.

In some embodiments, one or more steps are performed to speed up calculations. For example, the length and width of the cells can be increased in areas where the vessel does not change shape. Alternatively or additionally, a pressure drop can be automatically found from the calculated pressure field, such as when the pressure drop includes both the losses from viscosity and momentum. In some embodiments, to speed calculation times, system 10 can calculate the initial pressure field from 1-D equations based on area changes along the length. The equations of Kirkeeide (see Kirkeeide, R. L. (1991). Coronary obstructions, morphology and physiological significance. In *Quantitative Coronary Arteriography* (pp. 229-244). Kluwer Academic1) are especially suited for this application. Areas of reduced cross section are treated as the restrictions in his model. An individual "restriction" is considered a reduced cross section separated by number of diameters away from the next restriction, generally 5 to 10 diameters. If the restrictions are closer than this, then an estimate can be made of their interaction. The equations of Banerjee (see Banerjee, M. K., Nag, D., Ganguly, R., & Datta, A. (2008). Stenotic interaction on hemodynamic parameters in double stenoses. *International Journal of Computational Fluid Dynamics,* 22(9), 609-622. doi:10.1080/10618560802372033) can be used to estimate the interaction.

System 10 can be configured to calculate transition to turbulence from system 10 based correlations related to vessel wall divergence angle, adverse pressure gradient, Reynolds Number and the deviation of the flow profile from the parabolic shape. For all the calculations, the variation through the heart beat can be ignored (e.g. for coronary blood vessel analysis). In these embodiments, the principal concern is the wave free time during diastole when turbulent flow is the most likely.

Once transition to turbulence is determined by system 10, a separate turbulent model can be used. The 2-D Navier-Stokes equations can be (still) solved, but an artificially higher viscosity can be used. The K-Epsilon model can be used to calculate the length of the turbulent section. When the dissipation term drops below a preset threshold of system 10, the entire cross section is returned to laminar flow. The 1-D model can also include tests for transition to turbulence with the associated pressure drop increase.

For the 2-D model, if separation at the walls causes an unsteady solution, the reverse flow is not calculated, and the Navier-Stokes Equations are no longer used. Instead, the pressure drop for fully developed turbulent flow is used. The default length of this section is taken as five diameters and is shortened or lengthened based on whether the geometry is converging or diverging, and the Reynolds number of the flow. After that region, system 10 assumes a laminar parabolic velocity to enter the next section.

A transition to turbulence or a separation of flow along the wall generally means that an intervention needs to be performed (e.g. stenting). Thus, for the calculation of the decision to stent, correct calculation of the transition to turbulence is more important than the accurate calculation of the pressure drop in the turbulent section.

System 10 can be configured to convert non-circular sections to circular cross sections, for the purpose of these calculations. The hydraulic diameter, which is four times the cross-section's perimeter divided by the area, is used for the circular cross section diameter.

For the purposes of calculating FFR, system 10 can set the arterial pressure to 90 mm Hg and the venous pressure to 30 mm Hg. This pressure difference is the driving force for the flow. The FFR at any location is calculated as the local static pressure divided by the arterial pressure.

Figure 10:
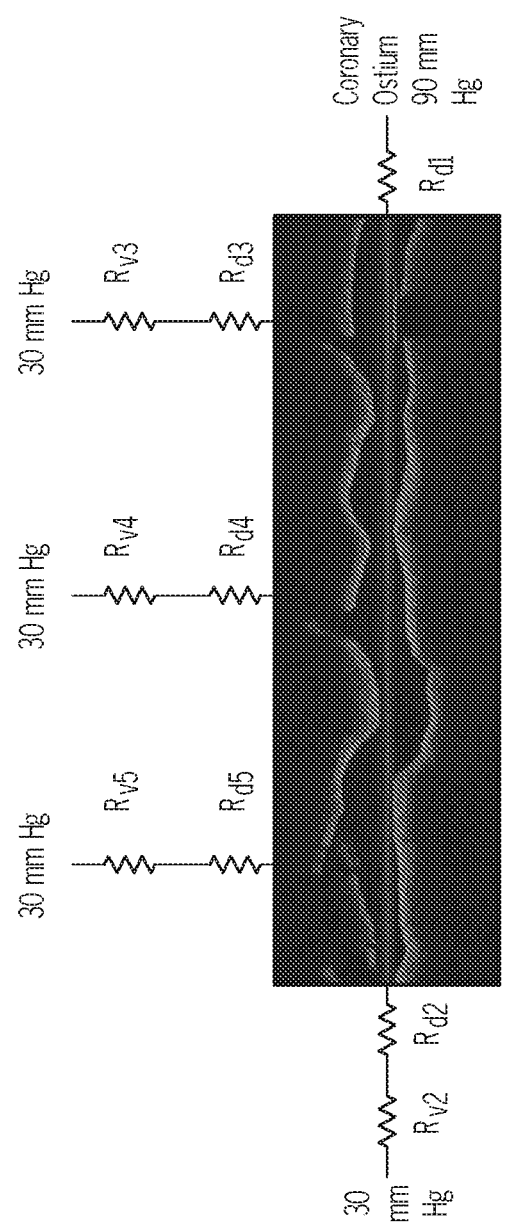
FIG. 10 illustrates a vessel flow schematic, consistent with the present inventive concepts.

Referring now to FIG. 10, a vessel flow schematic is illustrated. If there is disease at a side branch, the unimaged branch resistance from disease, $R_d$, is calculated by system 10. This resistance can be based on the calculated disease shape. The resistance can be estimated from the algebraic equations of Kirkeedee. The microvascular bed resistance R, for each side branch in the OCT image is put in series with $R_d$ for the diseased branches. Side branches below 1 mm diameter can be ignored as they don't significantly contribute to the flow. If the vessel ostium (e.g. the ostium of the imaged vessel, or an ostium proximal to the imaged vessel, vessel ostium herein) isn't imaged, a resistance is assigned to it, $R_{d1}$, based on other imaging (e.g. angiography) of the vessel ostium, if available, or based on a standard ostium shape, if not. The distal end of the image is assigned a microvascular resistance of $R_{v2}$, and diseased resistance assigned to it, $R_{d2}$, (if there is disease distal to the imaged area). $R_{d2}$ can be estimated from angiography or from a more distal OCT pullback.

System 10 can assume (e.g. for calculations) an initial flow at the vessel ostium of 3 ml/s for an artery on the right side of the heart, and an initial flow at the vessel ostium of 4 ml/s for a vessel on the left side of the heart. Starting from the vessel ostium, system 10 can determine an initial flow estimate by splitting up the ostial flow based on branch resistances, with no resistance applied to the imaged area. The imaged area can be broken into sections divided at each side branch as well as the distal and proximal ends. Then, Kirkeeide's and Banerjee's equations can be applied to each section and resistance at that flow can be calculated. Flow in each section can then be calculated from an explicit equation. The resistances can then be adjusted for that flow, and the flow recalculated from Kirkeedee's equations until a converged solution is obtained. If the calculated flow goes above 6 ml/s, the flow can be limited to a 6 ml/s maximum as these higher flows are not physiologic (i.e. not expected). A high flow estimate can be due to a slight misestimate of the microvascular resistance. This slight error does not have a significant effect on the FFR results as they relate to FFR values upon which treatment (e.g. stenting) decisions are made.

The flow and pressure at each side branch are the output of this calculation performed by system 10. The calculated pressure is used by the Navier-Stokes 2-D solver with a linear interpolation of pressure between each side branch. The non-imaged section(s) can still use Kirkeedee's and Banerjee's equations for $R_d$. System 10 can use the 1-D solver as an option.

To create an image using probe 100, blood must be flushed from the vessel being imaged. Currently available OCT catheters have a diameter that blocks a large part of the vessel, making decisions about whether to intervene (e.g. stent) difficult. Probe 100 of the present inventive concepts can comprise a significantly reduced diameter (e.g. a distal portion of no more than 0.030", no more than 0.023", no more than 0.020", and/or no more than 0.016"). Combined with a 0.014" guidewire, probe 100 and the guidewire take up no more than 0.044" of the vessel.

An FFR of 0.8 is generally accepted as the value above which the vessel is not to be treated (e.g. stented). To make decisions whether or not to stent an artery, OCT must be safe and effective at imaging vessels above and below this cutoff FFR. The cutoff FFR of 0.8 is associated with an MLA of 3.07 mm² (see Waksman, R., Legutko, J., Singh, J., Orlando, Q., Marso, S., Schloss, T., . . . Torguson, R. (2013). FIRST: Fractional Flow Reserve and Intravascular Ultrasound Relationship Study. *Journal of the American College of Cardiology,* 61(9), 917-923. doi:10.1016/j.jacc.2012.12.012). For a round vessel, this correlates to a 1.98 mm diameter vessel. Currently, the smallest commercially available OCT catheter is 2.6 F. Using this device and a 0.014 guidewire, most of the vessel (1.23 mm) is taken up by the combined devices. Occluding the vessel with this large of a catheter and guidewire makes it difficult to flush blood from the vessel to get a clear image, and otherwise complicates the imaging procedure.

System 10 can incorporate (e.g. take into account) the disease of the artery being investigated (e.g. at least imaged). If there is disease distal or proximal to an imaged area, its resistance to flow would need to be estimated, such as from angiography data, which is not as accurate as OCT data provided by system 10. Probe 100 and retraction assembly 800 can be configured to provide up to a 10 cm pullback, which can image from the vessel ostium to locations beyond the diseased areas for most coronary lesions (e.g. all lesions on the left side and for most of the lesions on the right side). System 10 can be configured to perform the pullback at a rapid rate, such as a rate that is faster than commercially available systems. System 10 (e.g. retraction assembly 800) can be configured to perform a pullback at a rate of 50 mm/sec (i.e. 10 cm in two seconds), such as with a 0.2 mm frame spacing. Two seconds is about the maximum time a vessel can be cleared with a safe dose of contrast (e.g. correlating to about 14 ml). Thus, probe 100, for almost all coronary lesion locations, is able to capture continuous images between a location distal to the lesion(s) and the vessel ostium. The 0.2 mm frame spacing provides sufficient resolution in imaging a stenosis to accurately calculate FFR.

System 10 can be configured to provide a long scan range, such as a scan range of up to 8.7 mm, such as to provide better identification of side branches. Typical coronary arteries do not exceed 5 mm in diameter (e.g. the left main is typically 5 mm diameter). System 10 can identify (e.g. via algorithm 51) a side branch, such as by the detected wall being significantly further away than the surrounding wall. Without a long scan range (e.g. a scan range that only reaches to the wall), side branch detection is more difficult.

The long scan range provided by system 10 also improves on estimating the diameter of a side branch. Imaging a significant length of side branch (at least 2 mm) allows finding the side branch direction and thus providing a better estimate of its diameter. The side branch size is correlated with branch angle. The larger the side branch, the smaller the angle to the main vessel. As disease tends to occur at bifurcations, system 10's ability to image beyond the bifurcation to determine the non-diseased diameter of the side branch, improves the estimation of the size of the vascular bed supplied by the side branch and thus the microvascular resistance assigned to that side branch.

The diameter of imaging probe 100 is sufficiently small to allow imaging of stenotic vessels or otherwise reduced diameter vessels in a pre-treatment procedure. Probe 100 can comprise a diameter of less than or equal to 1.7 F (0.022"). An imaging probe comprising a diameter of less than or equal to 2.2 Fr (0.029") allows for pre-intervention OCT imaging (e.g. can be used to image a reduced diameter portion of a blood vessel). In some embodiments, system 10 comprises a frame rate of 250 Hz, which allows for rapid pullbacks of extended lengths that can be used to capture lesion information, as well as information about the vessel ostium, in a single pullback. In some embodiments, system 10 also provides a scan range of no less than 6 mm, which allows for side branch detection and size estimation.

Fibrotic tissue, calcium, and lipids each have distinct attenuation and brightness values (e.g. when imaged by imaging probe 100 of system 10). Calcium is imaged via OCT as an area with a low backscattering coefficient and low attenuation; lipid shows high-attenuation and high-backscattering; and fibrotic tissue shows low attenuation and high backscattering (see Xu, C., Schmitt, J. M., Carlier, S. G., & Virmani, R. (2008). Characterization of atherosclerosis plaques by measuring both backscattering and attenuation coefficients in optical coherence tomography. *Journal of Biomedical Optics,* 13(3), 034003. doi:10.1117/1.2927464; see also Yabushita, H., Bouma, B. E., Houser, S. L., Aretz, H. T., Jang, I., Schlendorf, K. H., . . . Tearney, G. J. (2002). Characterization of Human Atherosclerosis by Optical Coherence Tomography. *Circulation,* 106(13), 1640-1645. doi:10.1161/01.cir.0000029927.92825.f6). Normal, non-diseased tissue can be identified by its three characteristic layers of the media, adventitia, and intima (see Tearney, G. J., Regar, E., Akasaka, T., Adriaenssens, T., Barlis, P., Bezerra, H. G., . . . Weisz, G. (2012). Consensus Standards for Acquisition, Measurement, and Reporting of Intravascular Optical Coherence Tomography Studies. *Journal of the American College of Cardiology,* 59(12), 1058-1072. doi: 10.1016/j.jacc.2011.09.079).

In some embodiments calcium and/or lipid deposits are automatically identified by system 10, such as by using 1-D (e.g. A-line classification), 2-D, and/or 3-D methods to analyze the OCT data. Machine learning approaches such as deep learning (e.g. convolutional networks) and/or supervised classification (e.g. support vector machine or random forest) can be used (e.g. by algorithm 51 of system 10) to automatically classify tissue types in OCT images. Image features such as optical backscattering, optical attenuation, layer analysis and texture analysis can be used. In some embodiments, automated and/or manual detection of calcium, lipid and normal tissue layers allows for improved calculation of flow (e.g. FFR) and/or procedure planning (e.g. determining the proper position of a stent to be implanted).

An estimate of microvascular resistance can be made by system 10, such as an estimation based on the size of a non-diseased vessel. Identification of the non-diseased sections would help microvascular resistance calculations. In some embodiments, the user can manually identify and/or correct the identified non-diseased sections, such as via user interface 55. In some embodiments, if too few non-diseased sections are identified in an OCT image (e.g. none or a limited number of normal sections can be found), algorithm 51 of system 10 can use information from one or more diseased sections for estimating microvascular resistance.

When treating cardiovascular disease, stents are sometimes placed across all diseased areas. Ideally the stent begins and ends in normal tissue. A stent placement algorithm (e.g. algorithm 51 of system 10) could consider not only FFR, but also one or more properties of the vessel wall. In some embodiments, stent placement algorithm 51 does not allow the user to place a proposed stent at a location that begins or terminates on diseased tissue (e.g. during a planning process, stents are only allowed to be placed spanning from healthy tissue to healthy tissue), and/or algorithm 51 warns the user that the selected stent ends are in a diseased portion of a vessel. Studies have shown that stenting onto lipid can be dangerous, as it can cause an embolic event. In some embodiments, if lipids are detected at one or more locations to be covered by a stent, a stent placement-based algorithm 51 prevents or alerts the user about positioning either end of the stent in lipid.

It may be difficult to fully dilate a vessel with a stent if calcium takes up the majority of the circumference of a wall. In some embodiments, if a significantly calcified section is identified by algorithm 51, the user is alerted that stenting may not be sufficient to open the stenosis. In some embodiments, after significant calcification has been identified, system 10 provides (e.g. suggests) alternate treatment methods, such as an atherectomy procedure (e.g. a rotational atherectomy procedure). In some embodiments, if circumferential calcifications are identified, this information is used when calculating post-treatment FFR values when simulating results post-stent implantation. Circumferential calcification may prevent the stent from fully expanding and calcium distribution information can provide a more detailed estimated lumen area to be achieved by stenting, providing improved guidance to the user.

In some embodiments, such as when algorithm 51 is configured to estimate the size of a side branch of an imaged vessel, the non-diseased vessel size of the imaged vessel is calculated. Sections of the imaged area that are significantly below this diameter may be checked for disease. If no disease is found in these areas, the vessel is likely in spasm, and should not be stented. In these instances, system 10 can alert the user that a spasm is likely. In some embodiments, when a spasm is identified by system 10, FFR can be calculated with and without the spasm, with both values being displayed to the user by system 10 (e.g. such that the user decides whether to stent based on the displayed information).

The improved pullback (e.g. longer length and/or increased speed) of the present inventive concepts increases the imaged vessel length (e.g. a greater length of a selected vessel can be imaged than with other imaging devices). In some instances, due to difficulty clearing blood, the vessel wall cannot be detected for the entire length of the pullback. System 10 can be configured to delineate the portion of a pullback which is clear, and the ends of the delineated length can be checked for presence of normal tissue. If the tissue at the end portions is diseased, angiography data can be analyzed to determine the extent of stenosis proximal and distal to the clear portion of the pullback. Subsequently, $R_d$ is calculated for these areas outside of the delineated pullback. Alternatively or additionally, the user can be notified that disease may exist outside of the imaged area and be prompted to enter the minimum diameter. The use of a user entered minimum diameter may not be as accurate as a more detailed lumen (as calculated from OCT data), but it allows for some input with limited information. If a portion of a pullback is unclear (e.g. due to poor blood clearing), the user can re-image the vessel. In some embodiments, the two images are combined by system 10 to create a hybrid image.

In some embodiments, the distal end of delivery catheter 80 is easily identified in the OCT data (e.g. when imaging assembly 115 is retracted into delivery catheter 80 during a pullback procedure). System 10 can assume that the vessel ostium is proximal to the distal end of delivery catheter 80, such as when system 10 assumes that delivery catheter 80 is placed a standard distance distal to the vessel ostium, such as a distance of approximately 5 mm. If there is disease at the ostium of the imaged vessel, the user may enter the minimum diameter at the ostium. The vessel display may show the anticipated size and location of the ostium. System 10 can enable the user to input a stenosed ostium's size.

In some embodiments, system 10 can comprise a digital model of the expected branching of one or more of the major vessels of the heart, such as described in reference to Step 1313 of Method 1000 of FIG. 6. Identification of major branches of the imaged vessel takes place from the vessel ostium. For example, if the LCx is imaged, the LAD is expected within 5 to 15 mm of the vessel ostium (see Abedin, Z., & Goldberg, J. (1978). Origin and length of left main coronary artery: Its relation to height, weight, sex, age, pattern of coronary distribution, and presence or absence of coronary artery disease. *Catheterization and Cardiovascular Diagnosis,* 4(3), 335-340. doi:10.1002/ccd.1810040318). Alternatively, if the LAD is imaged, the LCx is expected in the same region. If the branch detection-based algorithm 51 is unable to detect a branch in this region, the user can be warned and/or allowed to input the branch size and location, if in fact the branch was missed.

In some embodiments, non-OCT data (e.g. angiography data) can be analyzed by system 10 (e.g. by algorithm 51 of system 10) to determine microvascular resistance. Microvascular resistance estimation can be adjusted by system 10 for the vessel selected. The right-side heart microvascular resistance is lower for the same sized vessel. Instead of or in addition to determining the microvascular resistance based on the branch diameter, the non-OCT data can be analyzed by algorithm 51 of system 10, and a vessel territory can be assigned to each branch. The right side of the heart can be more complicated because the right side may or may not supply the left side of the heart (e.g. when the patient is right-side or left-side dominated). Automated and/or manual algorithms (e.g. algorithms 51) can allow assignment of the entire heart to particular vessels. This method is most accurate when both the left and right sides are imaged, which is not always done.

In some embodiments, system 10 obtains OCT image data by placing optical assembly 115 of probe 100 within a selected blood vessel, and this data can include vessel information such as vessel geometry information, vessel location information (e.g. with respect to anatomical landmarks), and the like. Second imaging device 15 can comprise a fluoroscope, positioned outside the selected vessel, which can gather non-OCT data that is similar or dissimilar to the OCT data gathered by probe 100. The angiographic data can include data representing an entire coronary tree, but at relatively low resolution (e.g. 150 µm to 250 µm resolution), for example captured at the same time as the OCT data. The OCT data can comprise data representing much higher resolution (e.g. approximately 10 µm resolution), with frames captured at rates of 250 frames/second. The OCT data can be used to create a 3-D model of the selected vessel, over a relatively long time span (e.g. from 0.5 seconds to 4.0 seconds). Either the OCT data or the non-OCT data can be used to calculate flow. Algorithm 51 can use techniques incorporating 3-D models, as described herein, such as native 3-D (e.g. using OCT data) or constructed 3-D (e.g. cat-scans and/or bi-plane angiography data).

In some embodiments, algorithm 51 analyzes data (e.g. OCT data captured over time) and creates a 2-D image set (e.g. a series of 2-D snapshots, or image frames, at well-defined points in time). Algorithm 51 can reduce the 2-D information to a descriptive single number, such as a hydraulic diameter or similar variable. This descriptive single number can be very effective for calculating flow drops and/or pressure drops. The calculation can depend on detection of a well-defined lumen contour, and algorithm 51 can incorporate image analysis techniques, machine-learning techniques, or a combination of these. Algorithm 51 can convert time information to a distance using various techniques to reduce error. For example, high-speed pullbacks (e.g. at least 50 cm/sec), gated pullbacks, angiographic co-registration, landmark co-registration (e.g. side branch co-registration), and the like. Algorithm 51 can include side branch information in a model, such as in the form of additional resistive elements, and/or flow modifiers. Additional information can be included (e.g. OCT data and/or non-OCT data) in a 1-D or 2-D straight-line model, such as when curvatures from angiographic images are included. In some embodiments, system 10 avoids the use of externally derived vessel geometries (e.g. curvatures or other geometry information from angiography data) when calculating flow and/or pressure (e.g. based solely on OCT data), such as to reduce calculation time.

In some embodiments, system 10 captures data in the form of r, theta, and, t where r is the radial distance from the zero-point and theta is the angle relative to a defined zero-angle. It is useful to transform r and theta to rectangular coordinates x, and y; t is the timepoint of the particular snap-shot (e.g. image frame). System 10 can calculate the local derivatives (slopes) for x and y:

$$x'_n = x_n - x_{n-1}; y'_n = y_n - y_{n-1} \text{(or other similar method)}.$$

With x, y, x', and y', system 10 can calculate the area and perimeter of the vessel cross section:

$$\text{Area} = A = \sum_{n=1}^{N} (x_n y'_n - y_n x'_n),$$

where N is the number of points in the circumference, and $$\text{Perimeter} = P = \sum_{1}^{N} \sqrt{(x'^2_n + y'^2_n)},$$

which is simply the sum of the 'little hypotenuses' around the shape.

System 10 can calculate these results as the OCT data is collected, and from that system 10 can calculate the hydraulic diameter:

$D_H$ 4A/p which reduces to the simple diameter for a circular section. This can be used to obtain accurate flow calculations using just a 1-D number.

Figure 11:
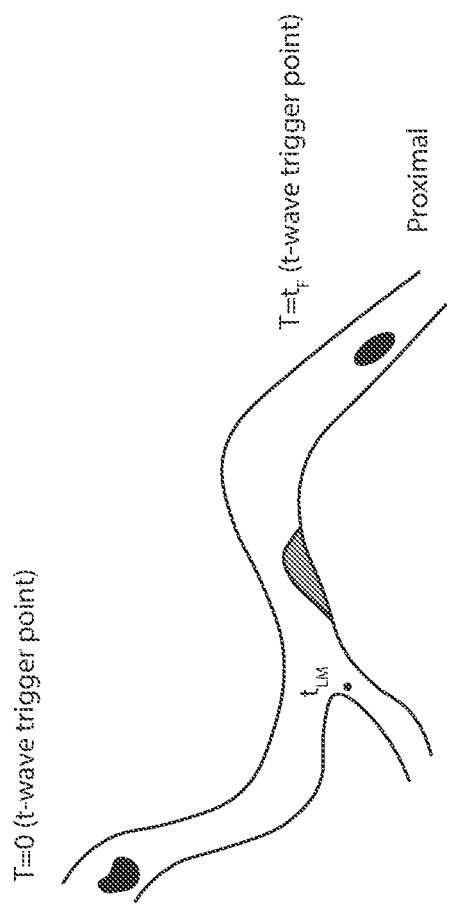
FIG. 11 illustrates a sequence of steps for performing a pullback procedure, consistent with the present inventive concepts.

System 10 can add lengths, by turning the time-points of each snap-shot into distances. For example, for a zero-order: the pullback speed is used to convert to distance. For first order: the start of the pullback is gated (e.g. with EKG T wave) with a low motion portion of the heart cycle, and a pullback speed is used to capture the relevant section of vessel length in approximately 50% of the heart cycle or less (e.g. 30 mm to 60 mm at a 100 mm/sec pullback rate). For second order: a gated pullback can be used, with semi or fully automated simplified co-registration (single plane angiographic image), see FIG. 11. With three sequences captured (sequences ii thru iv as shown in FIG. 11), a radiopaque marker of probe 100 can be identified at the start of pullback and at the end of the pullback, and an angiography image (frame) closest in time to the respective trigger (e.g. T-wave trigger correlating to the point in the heart cycle that the tissue is relatively motionless). Note that in sequences (ii) and (iv) there is no contrast flow (e.g. the vessel walls are not visible, but the radiopaque marker is visible). With the sequence captured during pullback, sequence (iii), the vessel walls are visible, but the radiopaque marker may be obscured. This sequence provides the shape curvature information, such as by using the best projection plane standard practice, such as to minimize out-of-plane issues. The distance traversed between the radiopaque marker at sequence (ii) and (iv) is the pullback distance (e.g. a distance of 50 mm). System 10 can map this known pullback distance along the artery shape, such as in a linear fashion. If landmarks are detected in the OCT image at time $t_{tm}$, system 10 can add further corrections, where the distance moved is $t_{tm}$ times the pullback speed.

In some embodiments, system 10 obtains non-OCT data comprising angiography data from second imaging device 15 (e.g. a device 15 comprising a fluoroscope). The non-OCT data can comprise sequential image frames that show the advancement of contrast agent through a blood vessel (e.g. through a coronary artery). System 10, via algorithm 51, can determine the change of contrast location from frame to frame, such as to estimate the velocity of the blood through the vessel, also referred to as the TIMI frame count, or TIMI score, where TIMI stands for thrombolysis in myocardial infarction. This frame count velocity can be for a location in the coronary tree, such as flow at the vessel ostium. System 10 can be used in an analysis using a resistor model of the coronary tree. For example, instead of a pressure estimation (e.g. 90 mmHg input pressure), the TIMI-based velocity is input into the resistor model. The input flow rate is the TIMI velocity times the vessel cross sectional area near the vessel ostium. Inlet pressure is allowed to rise or fall to cause the velocity to match the TIMI velocity. In this method, microvascular resistance does not change. System 10 can calculate FFR, as the local pressure is divided by the inlet pressure.

In some embodiments, system 10 is configured (e.g. via algorithm 51), to identify which particular vessel is the vessel being imaged (e.g. based on one or more side branches detected and/or the vessel geometric information (e.g. shape, trajectory, and/or size information)). This vessel identification can be made autonomously by system 10, and/or it can be confirmed by a user of system 10. In some embodiments, system 10 identifies the vessel, and/or confirms the vessel, using non-OCT data (e.g. using angiography data acquired from second imaging device 15 comprising a fluoroscope).

While the systems of the present inventive concepts have primarily been described in imaging and creating treatment information for arteries, and in particular coronary arteries, all blood vessels, and other body conduits should be considered within the spirit and scope of this application and its claims.

In some embodiments, system 10 is configured to compensate for cardiac motion. For example, a pullback can be performed (e.g. in a time period of no more than 0.3 seconds, or 0.2 seconds) that is synchronized to be started (e.g. via an EKG-based trigger) during a portion of a cardiac cycle that has minimal motion of heart tissue.

In some embodiments, imaging probe 100 comprises a unique identifier, such as an RFID or other identifier that can be read by console 50 (e.g. when imaging probe 100 is attached to patient interface module 200 (PIM 200)). In some embodiments, system 10 comprises a first imaging probe 100a and a second imaging probe 100b that are each identified with a unique identifier used to differentiate the two probes. In these embodiments, probe 100a and probe 100b can be of similar or dissimilar construction. For example, probe 100a and probe 100b can be of similar construction (e.g. the same construction), but each probe model results in a different configuration of system parameters (e.g. an automatic configuration that is established when the probe 100 is attached to PIM 200). In some embodiments, when probe 100a is attached to PIM 200, system 10 is enabled to calculate FFR values (e.g. on demand by a user), but when probe 100b is attached to PTM 200, FFR functionality of system 10 is disabled. In other words, an FFR-enabled probe 100 is required to enable FFR functionality of system 10, even if the only difference between an FFR-enabled probe 100a and a non-FFR-enabled probe 100*b* is the information included in an RFID or other model-identifying component of probe 100.

In some embodiments, when system 10 and/or probe 100 is enabled for FFR calculation, one or more system 10 parameters can be different than (e.g. modified from) a non-FFR enabled system and/or probe. For example, an FFR enabled system can be configured to rotate optical core 110 at a faster rate than a non-FFR system, such as at least 1.5 times faster, or at least 2 times faster. Faster rotation of core 110 can enable faster pullback speeds, longer pullback distances, and/or combinations of these, without a reduction in resolution of the collected image data. Additionally or alternatively, the faster rotation of core 110 enables light source 310 to deliver a higher output power without increasing tissue exposure. In some embodiments, an FFR enabled probe 100 can comprise more markers 131 than a non-FFR probe 100 includes, such as to enhance image-based tracking and/or improve registration accuracy (e.g. registration with fluoroscopy images and/or images from other imaging modalities).

In some embodiments, an FFR enabled probe 100 can be configured such that probe 100 extends beyond the tip of a delivery catheter, for example delivery catheter 480 described in reference to FIG. 1B herein. In some embodiments, probe 100 is configured to extend beyond a guidewire lumen, such as a rapid exchange guidewire tip of a delivery catheter. In these embodiments, probe 100 can be configured to capture image data distal to the distal end of a guidewire over which the delivery catheter has been advanced, such that the image data does not comprise any guidewire data (known as guidewire shadows). In some embodiments, extending probe 100 beyond the distal end of a delivery catheter allows imaging of a vessel with a smaller device (e.g. probe 100 has a smaller diameter than the delivery catheter), allowing for a minimal disruption of flow within the imaged vessel. Additionally or alternatively, the lack of any guidewire shadows in the image data allows for improved imaging, improved lumen reconstruction, and/or improved calculation of flow dynamics of the vessel.

In some embodiments, vessel identification information regarding one or more vessels to be imaged is captured by system 10, such as to associate vessel image, flow and/or other data to that identification. In some embodiments, a user enters the vessel identification information, and system 10 is configured to perform an assessment of the accuracy of this user-provided identification. For example, if system 10 determines that vessel information entered by the user is or at least may be inaccurate, an alert can be provided to the user. Alternatively or additionally, system 10 can be configured to identify a blood vessel, such as when system 10 automatically enters the blood vessel name into system 10 without user input (e.g. to save time). This automatic identification can be confirmed and/or adjusted by a user. In some embodiments, the vessel identification performed by system 10 is based on OCT data, non-OCT data (e.g. angiography information), or both.

In some embodiments, system 10 is used to image a blood vessel (e.g. create OCT data) both prior to and after a treatment procedure has been performed (e.g. a lesion has been stented). For example, system 10 can be configured to produce pre and post-treatment FFR data. In some embodiments, system 10 compares information produced based on image data (e.g. OCT data and/or non-OCT data) gathered prior to treatment, to information produced based on image data (e.g. OCT Data and/or non-OCT data) gathered after a treatment has been performed. This comparison can result in system 10 alerting the user of potential inaccuracies or other issues with the information provided by system 10. In some embodiments, probe 100 and other components of system 10 are configured to gather at least OCT data and produce a pre-treatment FFR value that is used to make a treatment decision (e.g. whether or not to stent or otherwise treat).

In some embodiments, system 10 is configured to provide information related to plaque-content of a lesion.

In some embodiments, information produced by system 10 based on OCT data and/or non-OCT data (e.g. at least angiography data) is used as "training sets" for a CT approach.

In some embodiments, information produced by system 10 is determined using OCT data and/or non-OCT data that is processed using machine learning or other artificial intelligence. In some embodiments, information produced by system 10 is determined using a cloud-based approach.

As described herein, system 10 can be configured to produce information (e.g. at least FFR values) prior to a treatment, that is used to determine whether or not to treat and/or how to treat. Imaging probe 100 can comprise a small profile (e.g. a distal portion with a diameter less than 0.034″) for accessing tight lesions, as described herein. System 10 can provide high resolution morphological images and other high-resolution morphological information, such as are produced using at least OCT data gathered by probe 100. In some embodiments, the high-resolution information produced by system 10 is based on OCT data and non-OCT data (e.g. at least angiography data).

In some embodiments, system 10 is configured to produce FFR information based on an OCT-derived lumen profile. The FFR information can also be based on side branch information. The FFR information can be based on combined OCT and non-OCT (e.g. angiography) information. The produced FFR information can be used (e.g. by a clinician of the patient) to decide whether or not to treat (e.g. whether or not to stent or otherwise treat a lesion).

In some embodiments, system 10 produces OCT image data (e.g. morphologic and/or lumen) and FFR data, and this combination of information is used (e.g. by a clinician) in planning a treatment procedure (including a decision of whether or not to treat). The provided information can also be based on non-OCT image data (e.g. angiography data) as described herein. The provided information can include morphological characteristics of a region of interest (e.g. a lesion), including the presence of calcium and/or lipids. The provided information can be used to determine which type of treatment should be performed (e.g. whether to perform an atherectomy procedure), and/or which size (e.g. diameter and/or length) of stent to implant. The provided information can include a prediction of results post-treatment (e.g. prediction of FFR post-treatment). For example, system 10 can be used to reduce delta FFR across a lesion and/or to achieve a desired FFR value (e.g. a value above 0.90).

In some embodiments, system 10 is used to treat multiple lesions (e.g. one or more serial lesions).

System 10 can utilize computational flow dynamics to model one or more lesions (e.g. each image using imaging probe 100 and/or second imaging device 15 of system 10), such as to determine which lesion to treat first. System 10 can be configured to provide information related to which of the one or more lesions to treat, such as when system 10 models each lesion's contribution to flow, such as to provide a clinician with information to decide which lesions to treat, and/or in which order to treat them.

In some embodiments, system 10 is configured to assess the outcome of a treatment of one or more lesions, such as when system 10 provides a quantitative or qualitative "score" of treatment success (e.g. efficacy and/or safety achieved via stenting and/or other treatment procedure). As described herein, such an assessment can include a post-treatment FFR calculation (e.g. including FFR value and/or delta FFR value), as well as post-treatment device assessment (e.g. an assessment of expansion, apposition, and/or position) and/or morphologic parameter assessment.

As described herein, system 10 is configured to predict the outcome of a treatment of one or more lesions, such as when system 10 provides a quantitative or qualitative "score" of predicted treatment success (e.g. efficacy and/or safety predicted to be achieved via stenting and/or other proposed treatment procedure). As described herein, such information can include a predicted post-treatment FFR calculation (e.g. including FFR value and/or delta FFR value), as well as a predicted post-treatment device assessment (e.g. a prediction of expansion, apposition, and/or position) and/or a morphologic parameter prediction. In some embodiments, if a prediction is below a threshold (e.g. a user or system 10 determined safety level), system 10 alerts the clinician of the potential issue. For example, system 10 can be configured to predict the likelihood of an acute event (e.g. an undesired acute event).

In some embodiments, system 10 is configured to provide blood vessel lumen contour images and/or other information, as described herein, such as when system 10 gathers OCT data and non-OCT data to produce the information. In some embodiments, system 10 utilizes one or more algorithms (e.g. algorithm 51), such as an algorithm utilizing artificial intelligence, to improve vessel contour information and/or other information determined by system 10. In some embodiments, algorithm 51 is configured to correct (e.g. allow a user to correct and/or automatically correct) blood vessel information. In some embodiments, system 10 is configured to alert a user of blood vessel information that is determined by algorithm 51 to have a low "confidence level", such as when a portion of calculated blood vessel information has been identified by system 10 as potentially being not sufficiently accurate (e.g. has a confidence level below a threshold). This identification of potential issues allows a rapid correction and/or accuracy confirmation by a user. Correction and/or confirmation ("correction" herein) can be accomplished in various ways, such as: frame-by-frame, L-mode (e.g. longitudinal display) and/or other 2D view; and/or a 3D view.

In some embodiments, system 10 is configured to identify one or more side branches of the imaged vessel, such as when algorithm 51 is configured to identify side branches. Algorithm 51 can utilize artificial intelligence and/or user input to identify the side branches. In some embodiments, system 10 is configured to identify side branches based on both OCT data and non-OCT data (e.g. angiography data). In some embodiments, system 10 is configured to alert a user of calculated side branch information that is determined by algorithm 51 to have a low confidence level, as described herein. In some embodiments, ostial diameter of a side branch is calculated by system 10. Alternatively or additionally, side branch ostial diameter of a side branch can be input and/or corrected by a user.

In some embodiments, system 10 is configured to provide 3-D lumen information, as described herein. In these embodiments, system 10 can include a triggered pullback, such as a pullback that is triggered based on a patient physiologic parameter such as cardiac cycle and/or respiration. For example, triggering a pullback during a low motion phase of a cardiac cycle can be used to limit motion artifacts and/or improve accuracy of implant and/or vessel information.

In some embodiments, system 10 assumes flow velocity and/or other physiologic conditions to be constant in healthy vessels.

In some embodiments, system 10 is configured to alert the user if a pullback is inadequate (e.g. OCT data gathered during the pullback is inadequate), such as when system 10 identifies that the entire length of a lesion has not been captured.

In some embodiments, system 10 is configured to image tandem lesions and/or bifurcation lesions.

The final location of a pullback (e.g. the most-proximal location) can be within a delivery catheter 80 through which probe 100 has been inserted, such as to gather ostial information of the imaged vessel(s). In some embodiments, system 10 is configured to analyze OCT data to determine that a pullback has ended at a location within delivery catheter 80 (e.g. a distal portion of delivery catheter 80 has been imaged). In some embodiments, system 10 is configured to alert the user if the final pullback location (pre or post-pullback) is not within delivery catheter 80 (e.g. distal to the distal end of delivery catheter 80). For example, such an alert can be performed to prevent (if pre-pullback) or indicate (if post-pullback) an insufficient amount of ostial information will be or is included in the OCT-data. In some embodiments, system 10 is configured to automatically identify an imaged delivery catheter 80 (e.g. model information and/or construction information regarding delivery catheter 80). In some embodiments, system 10 is configured to "crop" (e.g. remove) the image of delivery catheter 80 from provided vessel images (e.g. to reduce file size, provide a simplified luminal view, and the like). In some embodiments, system 10 is configured to assess the positioning of the guide within the imaged vessel, such as when system 10 is configured to alert the user if "improper seating" of the guide is suspected.

In some embodiments, system 10 comprises pre-set configuration information, such as "image acquisition recipes" comprising one or more imaging parameter values (e.g. pullback distances and/or rates, a flush parameter, rotation rate, frame density, and/or other probe 100 use parameters) that is correlated to a particular situation, such as imaging of a particular artery or other blood vessel.

In some embodiments, system 10 is configured to assess a flush procedure that is performed while gathering OCT data (e.g. during a pullback). For example, system 10 can provide quantitative and/or qualitative information regarding the flush procedure, such as to alert a clinician if the assessment is below a threshold of acceptability (e.g. when system 10 applies a low confidence to collected image data due to an improper flush procedure). In some embodiments, FFR and/or other calculated information is not provided unless an adequate flush is determined by system 10.

In some embodiments, system 10 is configured to assess the presence of vessel spasm (e.g. during pullback or other image data collection period). For example, system 10 can, via algorithm 51, detect presence of spasm and alert the user. Alternatively or additionally, system 10 can apply a low confidence to collected image data due to the detected presence of spasm. In some embodiments, FFR and/or other calculated information is not provided when vessel spasm is determined to be present by system 10.

In some embodiments, system 10 is configured to assess the presence of thrombus (e.g. during pullback or other image data collection period). For example, system 10 can, via algorithm 51, detect presence of thrombus and alert the user. Alternatively or additionally, system 10 can apply a low confidence to collected image data due to the detected presence of thrombus. In some embodiments, FFR and/or other calculated information is not provided when thrombus is determined to be present by system 10.

In some embodiments, system 10 is configured to assess the presence of vessel dissection and/or other vessel injury (e.g. during pullback or other image data collection period). For example, system 10 can, via algorithm 51, detect presence of vessel injury and alert the user. Alternatively or additionally, system 10 can apply a low confidence to collected image data due to the detected presence of vessel injury. In some embodiments, FFR and/or other calculated information is not provided when vessel injury is determined to be present by system 10.

In some embodiments, system 10 is configured to assess the presence of a myocardial bridge (e.g. during pullback or other image data collection period). For example, system 10 can, via algorithm 51, detect presence of a myocardial bridge and alert the user. Alternatively or additionally, system 10 can apply a low confidence to collected image data due to the detected presence of a myocardial bridge. In some embodiments, FFR and/or other calculated information is not provided when a myocardial bridge is determined to be present by system 10.

In some embodiments, system 10 is configured to gather at least OCT data, such as when both OCT data and non-OCT data (e.g. angiography data) are recorded.

Subsequently, dynamic flow calculations can be performed, such as flow calculations performed at a low resolution (e.g. to reduce computational time). Simultaneously or subsequently, image corrections can be made (e.g. automatically by system 10 and/or manually by a user), such as lumen and/or side branch corrections. After corrections can be made, additional dynamic flow calculations can be performed, such as flow calculations at a high resolution.

Figure 12A:
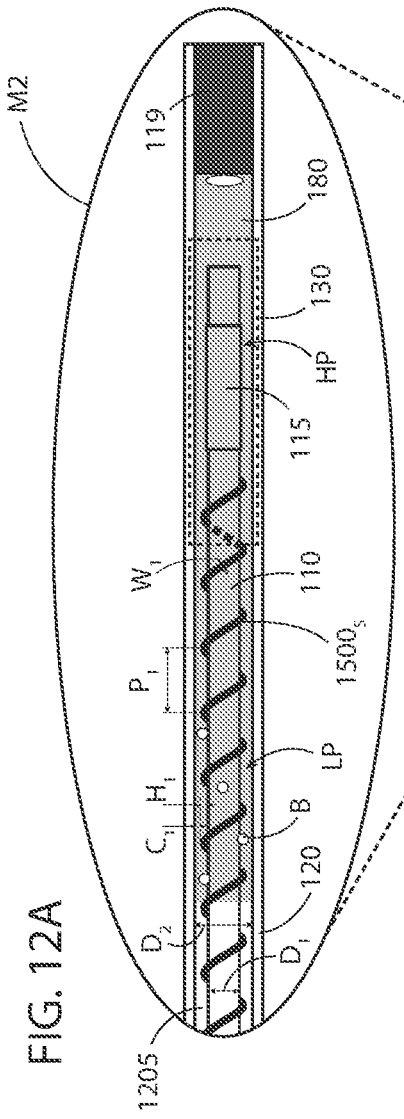
FIGS. 12 and 12A illustrate a schematic view of the distal portion of an imaging probe and delivery catheter, and a magnified view of the components within circle M2, respectively, consistent with the present inventive concepts.
Figure 12:
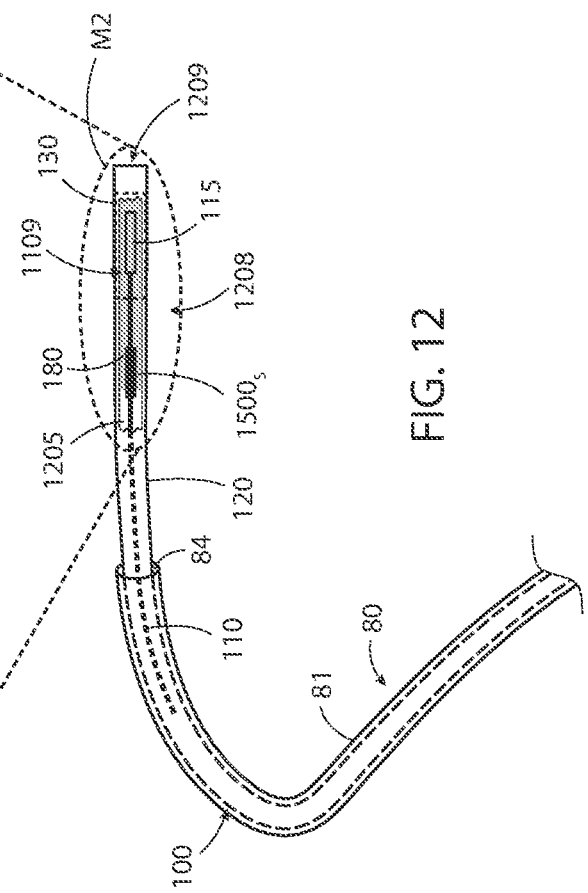

Referring now to FIGS. 12 and 12A, a schematic view of the distal portion of an imaging probe and delivery catheter, and a magnified view of the components within circle M2, are illustrated, respectively, consistent with the present inventive concepts. Imaging probe 100 and delivery catheter 80 can be of similar construction and arrangement to imaging probe 100 and delivery catheter 80 described in reference to FIG. 1. Delivery catheter 80 includes lumen 84, through which imaging probe 100 has been slidingly inserted. In the embodiment shown in FIGS. 12-12A, a fluid pressurization mechanism, FPE $1500_S$ shown, comprises a helical projection radially extending from optical core 110. During operation, as optical core 110 rotates, FPE $1500_S$ rotates in unison, generating a fluid flow proximate FPE $1500_S$, and causing a pressure gradient within gel 118 (e.g. across FPE $1500_S$). Modeling of examples of the fluid flow dynamics are described herein in reference to FIGS. 12B-C.

In some embodiments, FPE $1500_S$ comprises a helical coil, such as a spring or other wound wire, affixed along a portion of the length of optical core 110 (e.g. surrounding core 110). FPE $1500_S$ can be adhered, such as via glue or another adhesive, to optical core 110. In some embodiments, FPE $1500_S$ is molded on and/or with core 110, formed into (e.g. such as via a material removal process) core 110, fused onto core 110, and/or otherwise manufactured with or adhered to core 110. In some embodiments, FPE $1500_S$ comprises a material selected from the group consisting of: metal; plastic; stainless steel; nickel-titanium alloy; nylon; polyether ether ketone (PEEK); polyimide; and combinations of these. In some embodiments, FPE $1500_S$ can be formed directly onto optical core 110, such as using a deposition technique and/or 3D printing technique. In some embodiments, a selectively curable material is applied to optical core 110 and cured in a spiral pattern to form FPE $1500_S$. For example, a high-strength UV-cured adhesive can be applied to the surface of optical core 110 and selectively cured using a rotating, focused UV beam. In some embodiments, FPE $1500_S$ can comprise a material selected to minimize deformation of FPE $1500_S$ while the pressure gradient is applied. For example, during rotation a pressure gradient occurs across the length of FPE $1500_S$, such that to prevent deformation, a shorter FPE $1500_S$ would require a stiffer material than a longer FPE $1500_S$ configured to produce the same pressure gradient.

FPE $1500_S$ comprises a radial height, height $H_1$, which is the distance from the surface of optical core 110 to the outer edge of FPE $1500_S$. Optical core 110 comprises a diameter $D_1$. Lumen 1205 of shaft 120 comprises an internal diameter $D_2$. In some embodiments, diameters $D_1$ and $D_2$ vary along the length of probe 100, and the following dimensions relate to a segment of probe 100, such as a distal segment shown in FIG. 12A (e.g. a segment proximal and proximate optical assembly 115). Probe 100 can comprise a clearance $C_1$, between FPE $1500_S$ (e.g. the outer diameter of FPE $1500_S$) and the inner wall of shaft 120. Clearance $C_1$ relates both to the difference between diameter $D_1$ and $D_2$, and the height $H_1$ of FPE $1500_S$, such that $C_1$ equals one half of the difference between $D_1$ and $D_2$ minus $H_1$. In some embodiments, clearance $C_1$ comprises a clearance of no more than 100 µm, such as no more than 75 µm, such as between 10 µm and 75 µm. In some embodiments, height $H_1$ comprises a height that is between 5% and 95% of half the difference between $D_1$ and $D_2$, (e.g. a height $H_1$ that occupies at least 5% and/or no more than 95% of the space between the outer surface of core 110 and the inner wall of shaft 120). In some embodiments, the optimal height $H_1$ depends on factors such as: damping fluid viscosity (e.g. gel 118 viscosity); desired rotational rate of optical core 110; desired pressure gradient; and/or the clearance between FPE $1500_S$ and the inner wall of shaft 120 (e.g. tighter clearances create higher pressures). In some embodiments, the coil profile of FPE $1500_S$ comprises a width $W_1$ as shown. Width $W_1$ can comprise a width of 1% to 95% of diameter $D_1$. FPE $1500_S$ can also comprise a pitch $P_1$ as shown. Pitch $P_1$ can comprise a pitch such that the gap between adjacent coils is 0.5 to 20 times the diameter $D_1$. In some embodiments, adjacent coils do not come into contact with each other. In some embodiments, pitch $P_1$ is uniform along the length of FPE $1500_S$.

In some embodiments, gel 118 comprises a high viscosity, shear thinning fluid, such as is described in reference to FIG. 1. In some embodiments, the maximum functional clearance $C_1$ (e.g. the largest clearance $C_1$ allowable such that rotation of FPE $1500_S$ generates sufficient fluid pressurization within lumen 1205), is proportional to the viscosity of gel 118. For example, the higher the viscosity of gel 118, the greater the maximum clearance $C_1$. In some embodiments, the clearance $C_1$ is proportional to the pressure differential that can be generated within gel 118 by rotating FPE $1500_S$, as described herein. For example, the smaller clearance $C_1$, the greater the pressure differential that can be generated. In some embodiments, clearance $C_1$ and height $H_1$ are minimized to limit turbulent, recirculatory, and/or other unwanted fluid flow proximate optical core 110. In some embodiments, gel 118 comprises a Newtonian (non-shear thinning) fluid. The dimensions $C_1$, $H_1$, $D_1$, and $D_2$ can be optimized for differing properties of gel 118.

In some embodiments, FPE $1500_S$ comprises a covering (not shown). The covering can comprise a sheath, such as a heat shrink tube, and/or a painted or sprayed on coating. The covering can be configured to improve the bonding of FPE $1500_S$ to optical core 110, and/or to control the dimensions of FPE $1500_S$ (e.g. to hold FPE $1500_S$ tightly to optical core 110, such as to limit unwanted variations in height $H_1$). Additionally or alternatively, the covering can be configured to modify the surface properties of either or both of optical core 110 and FPE $1500_S$. In some embodiments, the covering comprises a thickness that does not significantly affect the fluid propulsion and/or other fluid pressurization ("fluid pressurization" herein) performance of FPE $1500_S$. Alternatively or additionally, FPE $1500_S$ can be constructed and arranged such that the dimensions $C_1$, $H_1$, and $D_1$ are optimal after the application of the covering.

In some embodiments, the pressurization of gel 118 within lumen 1205 caused by the rotation of FPE $1500_S$ exerts a functional torsional sheer force on the inner wall of lumen 1205. Shaft 120 can comprise a torsional resistance greater than the functional torsional sheer force exerted by gel 118. In some embodiments, gel 118 exerts a torque of approximately 0.004 N-cm, and shaft 120 comprises a torsional resistance of at least 0.01 N-cm, such as 0.03 N-cm. Additionally or alternatively, FPE $1500_S$ can exert a "wind-up" stress on optical core 110 as optical core 110 is rotated, driving FPE $1500_S$ within gel 118. Optical core 110 can be constructed and arranged to not be adversely affected by (e.g. not break or otherwise fail) the sheer stress induced by the rotation of core 110 and FPE $1500_S$ within gel 118 as well as the shear stress induced by the pullback motion within gel 118. In some embodiments, the additional windup stress on optical core 110 caused by FPE $1500_S$ functions as a NURD reduction mechanism, similar to NURD reduction caused by gel 118, as described in applicant's co-pending International PCT Patent Application Serial Number PCT/US2018/062766, titled "Imaging System", filed Nov. 28, 2018, the content of which is incorporated herein by reference in its entirety for all purposes.

Figure 12B:
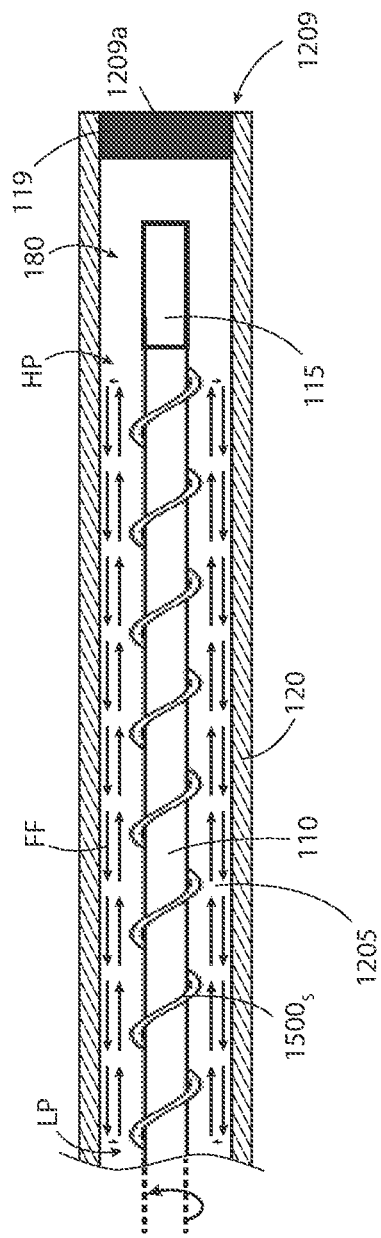
FIGS. 12B and 12C illustrate a schematic view of the distal portion of an imaging probe showing a fluid flow pattern, and a fluid flow simulation, respectively, consistent with the present inventive concepts.
Figure 12C:
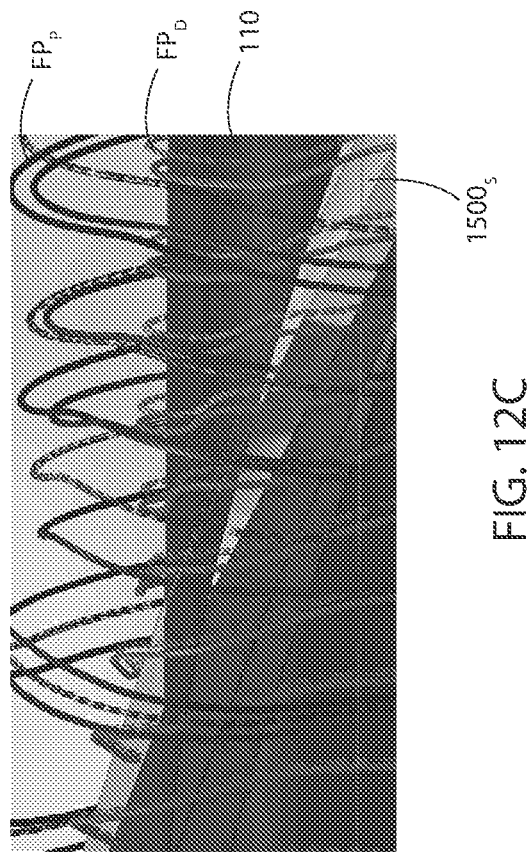

Referring additionally to FIGS. 12B and 12C, a schematic view of the distal portion of an imaging probe showing a fluid flow pattern, and a fluid flow simulation, are illustrated, respectively, consistent with the present inventive concepts. The motion of gel 118 is depicted by fluid flow arrows FF in FIG. 12B, and paths $FP_P$ and $FP_D$ in FIG. 12C. Optical core 110 and FPE $1500_S$ are depicted rotating with the top edge of FPE $1500_S$ rotating into the page. Along with the axial motion shown, a fluid flow comprises a rotational component as well, shown in FIG. 12C. The distal end 1209 and/or at least a distal portion of shaft 120 can be sealed, such as when distal tip 119 comprises a cap or plug configured as a sealing element, plug 1209a shown in FIG. 12B. Rotation of FPE $1500_S$ as shown causes a fluid flow proximate optical core 110 in the distal direction towards high pressure area HP. As the pressure within high pressure area HP increases to match the pressure of the distal fluid flow, a closed loop recirculation pattern emerges, as shown. Fluid propelled distally by FPE $1500_S$ encounters the pressure within high pressure area HP and redirects proximally along the surface of lumen 1205 (e.g. along a path of least resistance). This fluid flow pattern creates a "dead head" pressure profile (e.g. there is no net fluid flow), maintaining the pressure gradient along FPE $1500_S$, from low pressure area LP to high pressure area HP. As shown in FIG. 12C, fluid paths $FP_D$ depict fluid flow proximate optical core 110, distally towards high pressure area HP. Fluid paths $FP_P$ depict fluid flow proximate the surface of lumen 1205, proximally towards low pressure area LP.

Applicant has conducted various studies using the systems, devices, and methods of the present inventive concepts. Results from some of these studies are described herein. Images and other graphics associated with those studies are shown in FIGS. 13-23.

Figure 13:
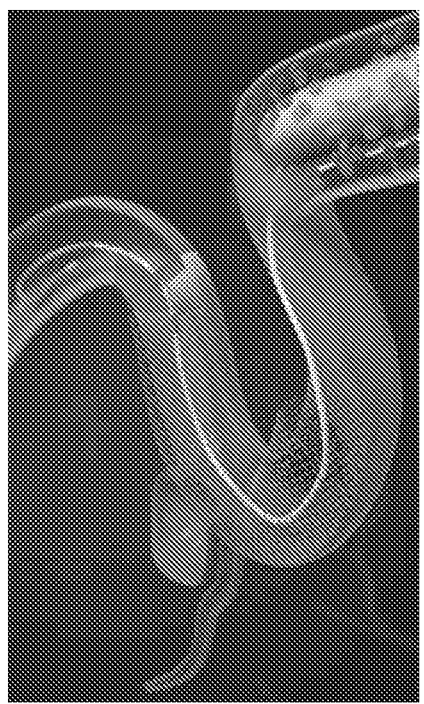
FIG. 13 illustrates the principles of system imaging in an intracranial vessel.

In FIG. 13, principles of system 10 imaging in an intracranial vessel are illustrated. During a brief injection of contrast using a 5F intermediate catheter, probe 100 is retracted while quickly rotating its internal optics resulting in a helical scanning pattern. By the means of a tightly spaced pattern (e.g., 60 µm) and an axial resolution approaching 10 µm, volumetric microscopy of the arterial wall, neurovascular devices and intraluminal objects is obtained.

Figure 14:
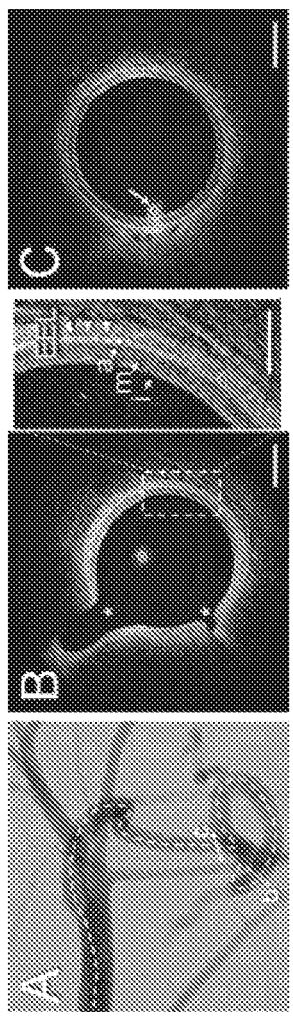
FIG. 14A illustrates a fluoroscopic image of a tortuous path through a flexed forelimb model of brachial porcine artery.
FIG. 14B illustrates system imaging of the flexed forelimb model of brachial porcine artery.
FIG. 14C illustrates the eccentric position of the imaging probe in the flexed forelimb model of brachial porcine artery.

In FIG. 14, in vivo imaging in a flexed forelimb model of brachial porcine artery is shown. In portion (A), the dotted line highlights the tortuous path taken by probe 100 through the vessel. In portion (B), system 10 microscopy shows the external elastic lamina (arrowheads) and the individual layers of the vessel wall (arrows). A bright tunica intima is followed by a dark tunica media and a bright adventitia (inset). The asterisks denote the ostia of two side-branches, with diameters of 0.2 mm and 0.7 mm, respectively. In portion (C), the arrow indicates the eccentric position of probe 100 in the arterial lumen. The image shows a uniform illumination and absence of NURD artifact. Scale bars are equal to 1 mm (B-C), and 0.5 mm in the inset.

Figure 15:
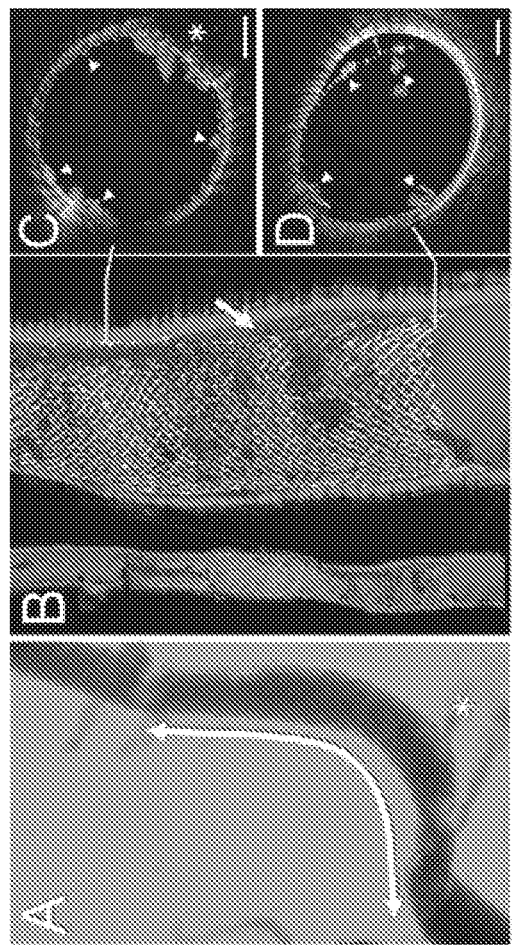
FIG. 15A illustrates vessel fluoroscopy of a stented swine internal maxillary artery.
FIG. 15B illustrates a system three-dimensional cutaway rendering of the stented swine internal maxillary artery.
FIG. 15C illustrates a cross-sectional system imaging of the stented swine internal maxillary artery.
FIG. 15D illustrates a cross-sectional system imaging of a flow diverter proximal edge of the stented swine internal maxillary artery.

In FIG. 15, system 10 three-dimensional in vivo imaging of a stented swine internal maxillary artery is shown. In portion (A) vessel fluoroscopy is shown; in portion (B), system 10 three-dimensional cutaway rendering (top=distal; bottom=proximal) is shown. Flow-diverter malapposition (arrow) and clots of different sizes (purple color) are visible over the flow-diverter surface. In portion (C), cross-sectional system 10 imaging shows a jailed branch (indicated by the asterisk) and several thrombus formations over the flow-diverter surface (arrowheads). Portion (D) shows a flow-diverter proximal edge, with incomplete apposition (3 o'clock) and several clots over the device surface (arrowheads). Scale bars are equal to 1 mm. Three-dimensional rendering color scheme: red, artery wall; purple, clot; silver, metallic struts.

Figure 16:
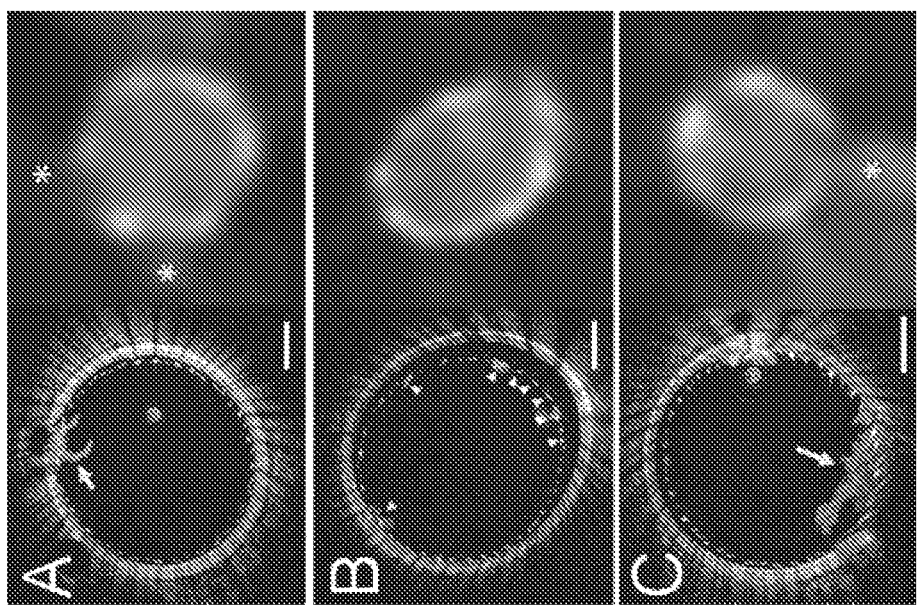
FIG. 16A illustrates a side-branch thrombosis visible on a system image.
FIG. 16B illustrates a flow-diverter malapposition with a maximum severity of approximately 400 µm visible on the system image.
FIG. 16C illustrates thrombosis on the ostium of a large side-branch.

In FIG. 16, cross-sectional system 10 images compared to corresponding CBCT slices are shown. Portion (A) shows a side-branch thrombosis is visible on the system 10 image (arrow). Portion (B) shows flow-diverter malapposition with a maximum severity of approximately 400 µm is visible on the system 10 image between 1 and 8 o'clock. Small thrombus formations over the flow-diverter struts, with a thickness between 30 and 220 µm, are indicated by the arrowheads. Portion (C) shows thrombosis on the ostium of a large side-branch. The presence of thrombus and device malapposition are often undetected on the corresponding conebeam CT images. Scale bars are equal to 1 mm. The asterisk (*) on CT images denotes the location of side-branches.

Figure 17:
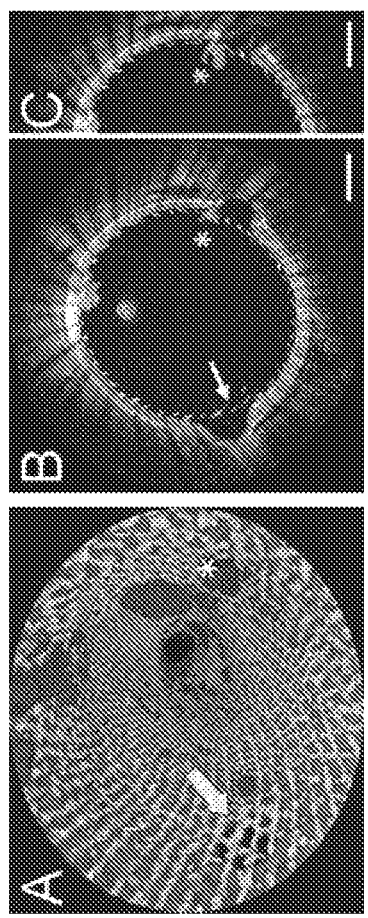
FIG. 17A illustrates an endoscopic view of system volumetric microscopy data.
FIG. 17B illustrates a first side-branch free of clots and an FDS well apposed to the parent artery.
FIG. 17C illustrates a second branch with FDS struts that are embedded by a clot.

FIG. 17 portions show: (A) an endoscopic view of system 10 volumetric microscopy data, where small, perforator-like side-branches jailed by an FDS are visible; (B) the side-branch located on the left side of the image (arrow) is free of clots and the FDS is well apposed to the parent artery; and (C) a second branch located on the right (indicated by the asterisk) shows FDS struts that are embedded by a clot.

Scale bars are equal to 1.0 mm. Three-dimensional endoscopic rendering color scheme: red, artery wall; purple, clot; silver, metallic struts.

Figure 18:
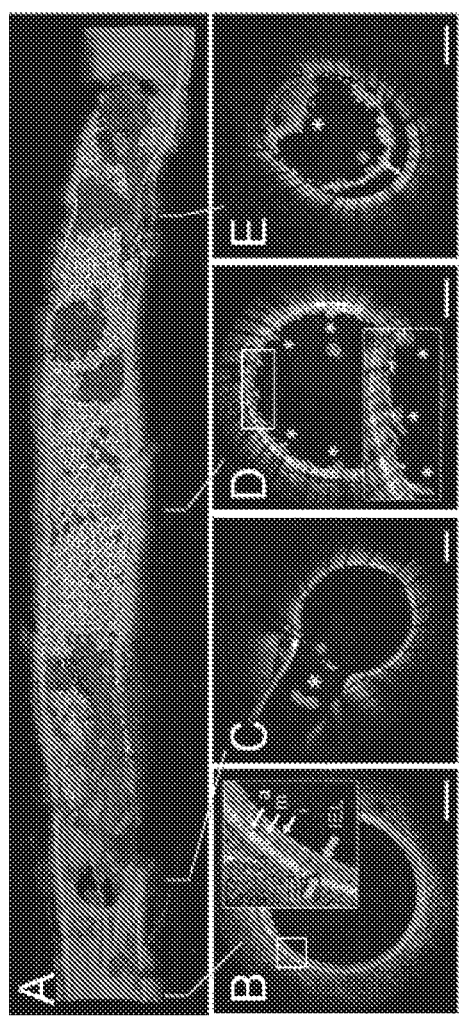
FIG. 18A illustrates system volumetric microscopy data showing an ICS partially overlapping with the distal end of an FDS.
FIG. 18B illustrates system microscopy showing individual vessel layers comprising a bright tunica intima, a low-scattering tunica media, and the tunica adventitia.
FIG. 18C illustrates a thrombus dislodged from the surface of an imaging probe floating inside a large branch.
FIG. 18D illustrates thrombus formations ranging between 100 μm and 200 μm in thickness and distributed over the FDS surface.
FIG. 18E illustrates a semi-occlusive clot formation in correspondence of a significant malapposition (e.g. at least 500 μm) and visible over the proximal end of the FDS.

FIG. 18 portions (A) and (B) show: (A) system 10 volumetric microscopy data showing an ICS partially overlapping with the distal end of an FDS; (B) system 10 microscopy showing the individual vessel layers comprising a bright tunica intima, a low-scattering tunica media, and the tunica adventitia (arrows). The internal elastic lamina (IEL) and the external elastic lamina (EEL) are indicated by the green arrows. In portion (C), a thrombus dislodged from the surface of the device floating inside a large branch is visible and denoted by the asterisk. In portion (D), thrombus formations ranging between 100 µm and 200 µm in thickness are indicated by the asterisks and distributed over the FDS surface. In portion (E), a semi-occlusive clot formation in correspondence of a significant malapposition (at least 500 µm) is visible over the proximal end of the FDS. Scale bars are equal to 1.0 mm. Three-dimensional endoscopic rendering color scheme: red, artery wall; purple, clot; silver, flow-diverting stent struts; gray, neurovascular stent struts.

Figure 19:
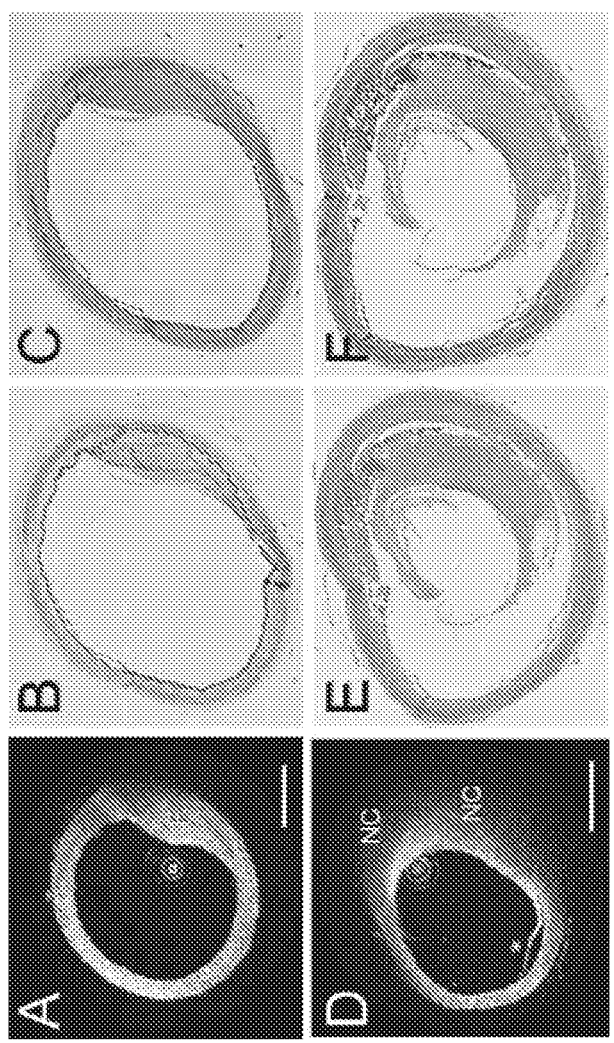
FIG. 19A illustrates system imaging of a fibrotic plaque and corresponding trichrome.
FIG. 19B illustrates a moyat's staining of the fibrotic plaque and corresponding trichrome.
FIG. 19C illustrates fibrotic tissue characterized by the imaging system as a region of homogenous signal, resulting from elevated backscattering and low optical attenuation coefficients.
FIG. 19D illustrates system imaging of a necrotic core plaque and corresponding H&E.
FIG. 19E illustrates moyat's staining of the necrotic core plaque and corresponding H&E.
FIG. 19F illustrates a necrotic core plaque characterized on system images as an area with poorly delineated borders followed by an elevated optical attenuation coefficient within an atherosclerotic plaque.

FIG. 19 shows intracranial plaques from an ex vivo segment of the MCA artery. Portion (A) shows system 10 imaging of a fibrotic plaque and corresponding trichrome (B) and movat's staining (C). Fibrotic tissue is characterized by system 10 as a region of homogenous signal, resulting from elevated backscattering and low optical attenuation coefficients. In portion (D), system 10 imaging of a necrotic core plaque with corresponding H&E (E) and movat's staining (F). A necrotic core plaque is characterized on system 10 images as an area with poorly delineated borders followed by an elevated optical attenuation coefficient within an atherosclerotic plaque. The asterisk indicates a vessel wall dissection. Scale bars are equal to 1.0 mm.

Figure 20:
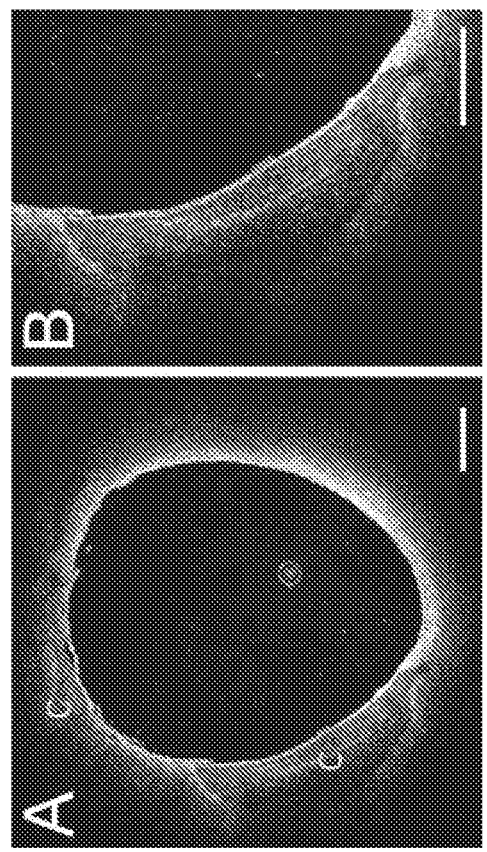
FIGS. 20A and B illustrate intracranial fibrocalcific plaques in a segment of an intradural vertebral artery.

In FIG. 20, intracranial fibrocalcific plaques in a segment of an intradural vertebral artery are shown. In portion (A), two fibrocalcific plaques are visible in the image (each indicated by the letter C). Portion (B) is a magnified view of the bottom left portion of the vessel of portion (A). A calcific plaque with a thickness between 100 µm and 300 µm is located at 11 o'clock. A second plaque with a maximum thickness of 900 µm is located in the bottom-left quadrant of the image. Calcific tissue is characterized by a sharply demarcated area with a low and heterogeneous signal, resulting from low optical backscattering and absorption coefficients. Scale bars are equal to 1 mm.

Figure 21:
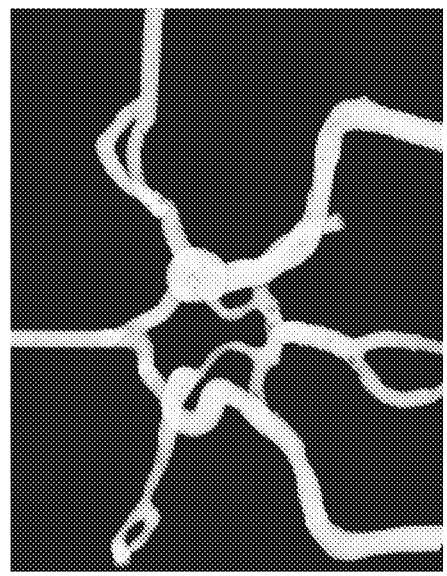
FIG. 21 illustrates a bench model of a full, patient-specific circle of Willis.

In FIG. 21, a bench model of the full, patient-specific circle of Willis is shown. Merging of the divisions of the middle cerebral and anterior cerebral arteries bilaterally was performed to reduce the complexity of inputs and output of the flow circuit. For the same purpose, individual branch arteries such as the ophthalmic and superior cerebral arteries were removed.

Figure 22:
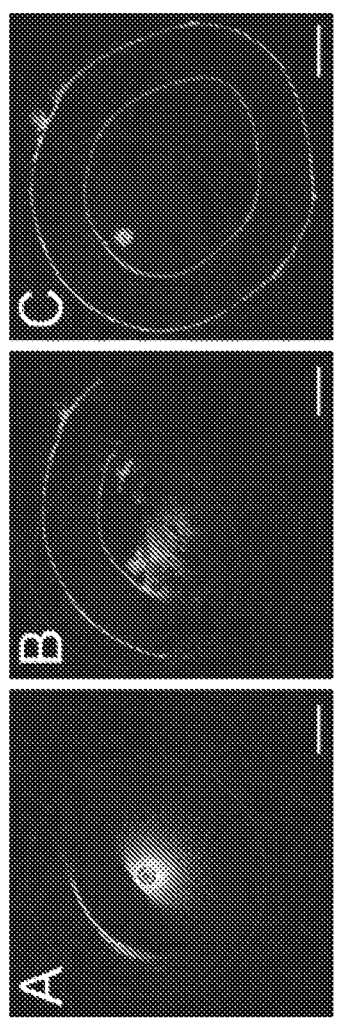
FIG. 22A illustrates blood obscuring a field of view.
FIG. 22B illustrates partial clearance of blood from the field of view.
FIG. 22C illustrates complete clearance of blood from the field of view.

In FIG. 22, images of blood clearance testing are shown, by classifying the image into three different categories: (A) blood obscuring the field of view, (B) partial clearance, (C) complete clearance. In all cases, the contrast media injection rate was increased from a value of 1 ml/sec, using increments of 0.5 ml/sec, until a complete clearance state was detected. Scale bars are equal to 1 mm.

Figure 23:
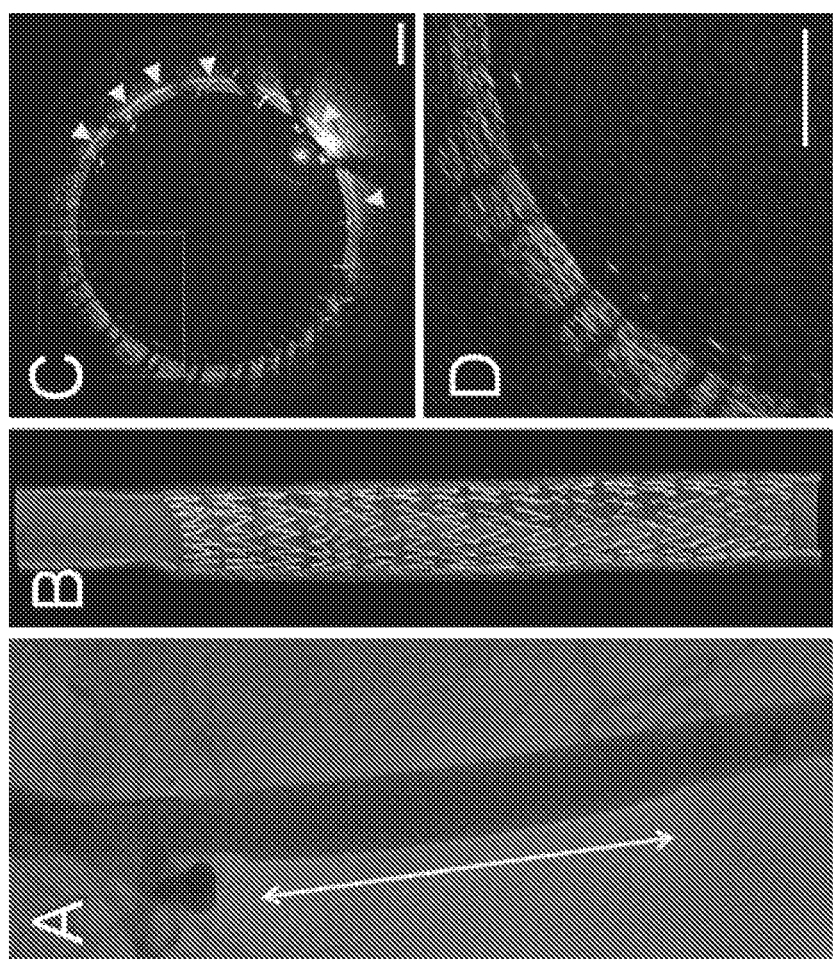
FIG. 23A illustrates system imaging of a stented segment in a swine common carotid artery with a maximum diameter of 5.9 mm following deployment of a Precise Pro Rx Carotid Stent System (Cordis).
FIG. 23B illustrates a three-dimensional system rendering of the swine common carotid artery.
FIG. 23C illustrates system cross sectional imaging of the swine common carotid artery.
FIG. 23D illustrates an external elastic membrane (EEL) of the Precise Pro Rx Carotid Stent System.

In FIG. 23, images of system 10 of a swine common carotid artery with maximum diameter of 5.9 mm following deployment of a Precise Pro Rx Carotid Stent System (Cordis) are shown. In portion (A), the stented segment is indicated by the arrow. Portion (B) shows three-dimensional rendering of a system 10 image. Portion (C) shows system 10 cross sectional imaging, illustrating the extended field-of-view of system 10 imaging technology. Even when probe 100 is located in an eccentric position within the arterial lumen, system 10 can visualize the entire stent and the arterial wall with sufficient brightness and illumination, as shown in portion (D). The arrowheads indicate the external elastic membrane (EEL). Scale bars are equal to 1.0 mm.

In current clinical practice, the endovascular treatment of stroke and other undesired cerebrovascular conditions is performed under the guidance of non-invasive imaging technology which is unable to provide sufficient resolution to adequately assess the underlying vessel pathology, device-vessel relationship, small perforating arteries and device related platelet aggregation. Intravascular, volumetric microscopy imaging performed using the optical probes and other system components of the present inventive concepts enables the patient's clinician to visualize the vessel wall microstructure and its interaction with neurovascular devices, and its use would have a profound impact in the treatment of cerebrovascular disease. System 10 is configured to rapidly acquire volumetric microscopy data at a resolution approaching 10 microns in highly tortuous vascular anatomy. Using system 10 in a combination of in vitro, ex vivo and in vivo models, its feasibility and efficacy for cerebrovascular microscopy has been demonstrated. Results of these studies has demonstrated the potential of system 10 for the imaging of intracranial arteries and for providing guidance for neuroendovascular therapeutic procedures.

Endovascular treatment of ruptured brain aneurysms results in less death and dependence as compared to surgery, with similar trends reported in the treatment of unruptured aneurysms. Self-expanding microstents and flow diverters, designed for the cerebrovasculature, with struts as small as 25 µm, have enabled the treatment of wide-neck, complex aneurysms. Given the limited x-ray attenuation of these devices on x-ray-based imaging systems, radiopaque markers are distributed along these treatment devices; however, it is currently not possible to properly image the entire device. This limitation is critically important since an accurate device placement with respect to the pathology and apposition are necessary for effective treatment and prevention of disabling complications. Despite tremendous advances in minimally invasive therapies, there currently remain limitations to endovascular treatments largely related to inadequate visualization of the device-vascular interface. Neurovascular treatment devices require particularly precise placement of the device to achieve the ultimate goal (e.g. complete exclusion of an aneurysm from the circulation). Moreover, endovascular thrombectomy (EVT) has become the standard of care for eligible patients suffering from ischemic stroke due to a large vessel occlusion. Non-invasive imaging techniques such as magnetic resonance (MR) vessel wall imaging have been proposed to assess vascular damage following EVT, however, there is insufficient resolution to directly visualize the underlying pathology (e.g., intracranial atherosclerotic disease or dissection), endothelial injury, and/or perforating arteries thrombosis.

Use of system 10 to perform volumetric microscopy, with the ability to visualize neurovascular devices in their entirety and the vessel wall microstructure in vivo, will have a profound impact in endovascular neurological treatments. Optical imaging techniques provided by system 10, with a resolution approaching the micron scale and feasible incorporation in small fiber-optics probes, are a promising candidate for a successful translation to clinical settings in which patients are treated. In the last decade, intracoronary optical coherence tomography (OCT) has become an increasingly popular modality, as it enables accurate measurements of the coronary lumen morphology, disease severity, and intracoronary stents. System 10 can be configured to provide an assessment of disease severity, such as an assessment that includes quantitative and/or qualitative assessment of disease severity. Beyond coronary applications, system 10 has the potential to revolutionize the diagnosis and management of cerebrovascular pathologies, such as: by imaging probe 100 providing the flexibility required to be advanced in tortuous cerebrovascular anatomy; by the ability of imaging probe 100 to perform imaging in elevated tortuosity; and/or by the components of system 10 being compatible with standard neurovascular clinical workflow. In addition, the enhanced field-of-view (i.e. acquired image diameter) of system 10 is sufficient to characterize large and complex carotid arteries and intracranial aneurysms. In applicant's studies, meeting of these cerebrovascular requirements was achieved using system 10.

Results

In various studies, system 10 was used to perform volumetric microscopy in a combination of in vitro, in vivo and ex vivo models of cerebrovascular arteries. The imaging probe 100 used comprised a 0.016-inch wire-like catheter capable of being delivered through standard neurovascular microcatheters. Probe 100 is designed to have a comparable profile with state-of-the-art guidewires and features an atraumatic, radiopaque tip. The probe 100 optics have the ability to focus and collect the near-infrared light that is backscattered by the vessel wall and intraluminal objects. Through a rapid rotation of optical assembly 115, and via retraction of probe 100 through the vessel, system 10 performs volumetric imaging of the surrounding artery and any implanted device at a resolution approaching 10 μm, reference FIG. 13. System 10 enables the acquisition of data at a frame rate of 250 images per second, with a field of view (i.e., image diameter) of at least 14 mm, from tortuous arterial segments longer than 50 mm, in 2-3 seconds.

Vessel Clearing in an In Vitro Circulating Model of the Circle of Willis

Red blood cells scatter light and degrade its coherence properties and, as such, the acquisition of data by system 10 requires the displacement of the arterial blood from the vessel lumen. To test the ability to infuse sufficient contrast agent for the creation of a suitable optical window, simulated use experiments were performed in a patient-specific bench model of the complete circle of Willis, reference FIG. 21. Importantly, the model includes communicating arteries that have the potential to mix with injected contrast and obscure the acquisition of images by system 10. A pulsatile pump was used to circulate swine blood, and the optimal contrast injection protocols were identified at the location of the internal carotid (ICA), middle cerebral (MCA), basilar (BA) and vertebral (VA) arteries. For each of these locations, imaging probe 100 was delivered to the target anatomy and contrast media infused via a power injector through a 5F intracranial support catheter (5F Navien, Medtronic Neurovascular, Irvine CA). Different concentrations of Omnipaque (GE Healthcare) radiopaque contrast were tested, including 240, 300 and 350 mgI/mL with a viscosity of 3.4, 6.3 and 10.4 cp at 37° C., respectively. Injections were performed using an automated pump (Medrad Mark 7 Arterion Injection System, Bayer HealthCare) flushing through the 0.058" inner lumen of the intracranial support catheter at a pressure limit of 300 psi.

Clearance as a function of the contrast delivery rate was analyzed using a system 10 imaging metric by classifying the results in three categories: blood obscuring the field of view, partial clearance, and complete clearance, reference FIG. 22. Starting from 1 ml/sec and using increments of 0.5 ml/sec, the flow rate of the contrast medium was increased until complete clearance was obtained and the optimal flushing protocol for each anatomical location determined. Omnipaque 350 was identified as the preferred media, having an optimal viscosity to efficiently displace the blood from the image field of view. Complete clearance of the ICA was obtained by flushing at 5 ml/sec and was observed after approximately 2-3 seconds of injection. Similarly, clearance of the MCA and the VA was obtained at a rate of 3 ml/sec. The BA required a 5 ml/sec injection to overcome the inflow from both VAs with the 5F catheter positioned at the level of the BA ostium. A rate of 4 ml/sec may be able to provide sufficient clearance when injecting contrast within a more distal position of the BA. System 10 data acquisitions with a duration of 2 seconds were shown to require injections for a minimum of 4 seconds to clear the artery, resulting in a 20 ml injection of contrast media for the ICA at 5 ml/sec and a 12 ml injection for the MCA at 3 ml/sec.

Imaging in Elevated Vascular Tortuosity In Vivo

A flexed forelimb swine model (n=8) provided severe tortuosity conditions in brachial arteries, with a curvature similar to human ICA siphon. Imaging probe 100 was tested bilaterally in brachial arteries (n=16) acquiring system 10 image data sets with an effective imaging length of 65 mm+13 mm. The performance of the probe 100 devices was evaluated by assessing image artifacts that typically affect state-of-the-art intravascular technologies in tortuous anatomy, such as non-uniform rotational distortion (NURD). NURD is defined as an artifact occurring because of an increased friction on the rotating catheter components; it appears as smearing in the circumferential (rotational) direction, and it causes distortions that may lead to incorrect image interpretation and measurements. In brachial artery tortuosity (n=16), the system 10 data sets had no observed NURD artifacts. FIG. 14 shows an example of system 10 imaging. Angiography illustrates an elevated vascular tortuosity. Distortion-free imaging by system 10 with a uniform vessel wall illumination allowed precise visualization of the individual tissue layers, external elastic laminae (EEL), detailed lumen morphology and the ostia of two side-branches, reference FIG. 14B-C.

Imaging of Neurovascular Stents and Flow-Diverters In Vivo

A comparison between digital subtraction angiography (DSA), contrast-enhanced conebeam CT (CBCT), and system 10 imaging was performed by acquiring data sets from swine internal maxillary arteries (IMAX, n=16), implanted with flow diverting stents (FDS, n=16) and self-expandable intracranial stents (ICS, n=15). Expert image readers (n=3) analyzed the presence of thrombus formations and malapposition using a binary outcome metric across the different modalities. Each reviewer analyzed a total of 480 images that included angiographic runs, system 10 and CBCT cross-sectional images. Fleiss' kappa statistic was used to assess the agreement between the different reviewers. An agreement was found of 0.90 (system 10), 0.67 (CBCT), and 0.49 (angiography) for the assessment of acute thrombus formation along the surface of the FDS. Values of 0.87 (system 10), 0.67 (CBCT), and 0.18 (angiography) for the diagnosis of device malapposition were found. A repeated analysis for the ICS device showed an agreement to visualize thrombus formation of 0.81 (system 10), 0.39 (CBCT) and 0.71 (angiography). Values of 0.78 (system 10), 0.45 (CBCT), and 0.41 (angiography) were found for ICS malapposition.

Examples of imaging data following FDS implantation are shown in FIG. 15. System 10 volumetric microscopy illustrates the presence of thrombus accumulations and of incomplete device apposition, reference FIG. 15B. A side-branch occlusion and FDS edge malapposition covered by multiple thrombus are detected, reference FIG. 15C-D. System 10 images and corresponding CBCT data are shown in FIG. 16 (system 10 images on the left, and CBCT data on the right). Side-branch thrombosis, reference FIG. 16A, malapposition of the device, and clots as small as 5 µm, 10 µm, or 30 µm, reference FIG. 16B, can be sufficiently captured by system 10 provided OCT images (e.g. identified by system 10 or by a clinician viewing images produced by system 10), and are often unseen (e.g. unidentifiable) on a corresponding CBCT cross-sections (e.g. as shown in FIGS. 16A-C). Further examples of the ability of system 10 images to depict neurovascular devices in vivo are shown in FIG. 17 and FIG. 18. Endoscopic data rendering illustrates two perforator-like branches that are jailed by an FDS, reference FIG. 17. The presence or absence of clots over their ostia is captured by system 10 images, reference FIG. 17B-C. Accurate visualization of the individual layers of the vessel wall, thrombus accumulation at the level of a side-branch jailed by an ICS, and small clots with a thickness of 100 µm are accurately captured by system 10 imaging, reference FIG. 18B-D. A partial vessel occlusion as a result of significant thrombosis over a malapposed FDS proximal edge is illustrated in FIG. 18E.

Imaging in Large Arteries

To investigate the ability of system 10 to image large carotid arteries, stenting of common carotids was performed in a subgroup of the non-human animals (n=5). The diameter of the stented segments was found to be on average 5.5 mm+0.3 mm, with a maximum diameter of 5.9 mm. In all cases, the extended field of view of system 10 provided sufficient illumination to accurately assess the stent-vessel interaction on a strut level, reference FIG. 23.

Imaging of Intracranial Atherosclerosis

Segments of diseased intracranial arteries (n=10) were obtained at autopsy from human patients older than 70 years of age with a history of vascular disease. Specimens were submerged in saline, and multiple system 10 image acquisitions were obtained to sample the entire length of each artery (n=15). Following the system 10 imaging procedure, an expert image reader identified a subset of the vessel segments containing representative examples of the three main plaque types using criteria previously established. Representative examples of fibrotic, fibrocalcific and necrotic core atherosclerotic disease were found (n=3). Tissue was processed by the means of histopathology techniques and stained using Sudan's black, Hematoxylin and Eosin (H&E), van Gieson's, Movat Pentachrome, and Trichrome reagents. A vascular pathologist blinded to system 10 imaging results analyzed the stained slices and characterized the plaques and tissue type. Agreement was found in all cases (n=3). Examples of intracranial plaques are shown in FIG. 19 and FIG. 20. A fibrotic plaque located in the M1 segment of the MCA of a cadaver of 97 years of age is shown in FIG. 19A. Using previously established criteria, a fibrotic plaque was identified on system 10 images as a thicker region of the artery wall exhibiting elevated optical backscattering and homogeneous intensity. Histopathology assessment categorized this plaque to be mostly composed of fibrotic tissue, reference FIG. 19B-C. A second plaque containing a necrotic core (NC) is illustrated in FIG. 19D. NCs are identified on system 10 images as signal-poor areas with poorly delineated boundaries within an atherosclerotic plaque covered by a fibrous cap. Necrotic tissue presents a strong optical attenuation, resulting in a fast image intensity signal drop-off, shadowing the vessel wall region located behind. Histopathology classified this plaque as fibrotic with a NC and underlying media degeneration, reference FIG. 19E-F. Lastly, a fibrocalcific plaque was identified in the distal segment of an intradural vertebral artery from a cadaver of 86 years of age. System 10 images display fibrocalcific plaques to contain evidence of fibrotic and calcific tissue, characterized by a signal-poor and heterogeneous region with sharply delineated borders. A fibrocalcific plaque, with a circumferential distribution of 87 degrees and a maximum thickness of approximately 900 µm, is shown in FIG. 20B. Calcific tissue presents low backscattering and attenuation coefficients in the near-infrared and, as a result, system 10 can accurately visualize both its thickness and circumferential distribution. Histopathology assessment categorized this plaque as mostly calcific, with evidence of underlying media degeneration and positive remodeling.

DISCUSSION

Imaging performed using system 10 has the potential to provide sufficient spatial resolution to visualize details of neurovascular devices at a strut level that are unseen by state-of-the-art clinical imaging modalities. Previous research has shown the potential of intravascular imaging techniques for neurovascular applications; however, due to the mechanical characteristics of the existing coronary imaging catheters, their translation to tortuous cerebrovasculature was unfeasible. The data presented in applicant's studies illustrate how system 10 enables volumetric microscopy of intracranial arteries. Using a patient-specific in vitro model of the full circle of Willis, studies have presented contrast injection protocols that allow system 10 imaging at different neurovascular anatomical locations. The optimized injection protocols established for system 10 imaging do not differ from routine practice in neurointerventional surgery for the acquisition of rotational angiography, and in practice the acquisitions of these two different imaging modalities could occur simultaneously. In an in vivo non-human animal model, evidence was collected of the suitability of imaging probe 100 for imaging in elevated vascular tortuosity, comparable to the elevated tortuosity conditions encountered in the human ICA. Volumetric microscopy using system 10 resulted in much higher inter-operator agreement for the quantification of intraluminal clots and assessment of the interaction of neurovascular devices with the arterial wall, compared to state-of-the-art imaging modalities such as DSA and CBCT. Furthermore, existing criteria was translated for intravascular imaging to system 10 imaging, illustrating its ability to visualize the vessel wall microstructure and to characterize intracranial atherosclerosis. Taken together, the results of applicant's studies pave the way for the clinical translation of system 10 for intracranial imaging in the human clinical setting.

A growing body of pre-clinical evidence supports the speculation that cerebrovascular microscopy, with the ability to assess vessel wall disease and neurovascular devices, will have a profound impact on the endovascular treatment of cerebrovascular disease. Recently, it has been shown in a rabbit aneurysm model that the complete apposition of flow-diverting stents is critically important to achieve early and complete aneurysm occlusion, but histological evidence of poor apposition was not accurately captured on gold-standard DSA. Communicating malapposition between the aneurysm neck and flow-diverting devices, unseen on non-invasive modalities but captured by intravascular OCT, was shown to be a predictor of subsequent early aneurysm occlusion. Similarly, gaps in intrasaccular device reconstruction of aneurysm necks, observed by system 10 images and undetected on CBCT, were shown to correlate with subsequent lack of occlusion. MRVW is the method of choice for intracranial vessel wall imaging in the context of ischemic stroke and intracranial hemorrhage; however its accuracy is significantly affected by a limited spatial resolution and voxel size. A recent study showed that high-resolution intravascular imaging was able to reveal endothelial injuries, residual thrombus and ongoing thrombosis on basilar artery perforators at the lesion site following EVT, in cases where angiographic techniques showed a complete recanalization and no clots were visible on CT angiography and MRVW.

System 10 enables volumetric microscopy of the arterial wall at a resolution approaching 10 μm. In applicant's studies, it has been shown in an animal model that system 10 can accurately identify intraluminal thrombus and neurovascular devices at a strut level. These results, in combination with the evidence provided for imaging in tortuous anatomy, suggest that system 10 can be used clinically for peri-procedural assessment of neurovascular devices so that corrective measures, such as local administration of GP IIb/IIIa inhibitors, angioplasty or additional stenting, can be deployed. In cases where angiographic findings are ambiguous, the superior resolution of system 10 imaging allows the visualization of vessel dissections and stent-vessel interactions which non-invasive imaging techniques are unable to capture. An accurate characterization of intracranial atherosclerotic plaque type may inform treatment decisions as well as enable improved stent sizing, placement and interaction with perforating arteries and residual stenosis for improved treatment of intracranial arteries. System 10 may enable more informed, image guided, personalized antithrombotic management after EVT. The superior resolution of system 10 images provides the ability to study the vessel and aneurysm healing response to an implanted device at an unprecedented level, assessing the tissue thickness over the device surface and vascular remodeling with precision and accuracy of microscopy techniques in vivo. As such, the use of system 10 provided cerebrovascular microscopy offers great potential for monitoring device healing in clinical practice, assessing endothelial overgrowth and intimal hyperplasia, and offering insights for optimal antiplatelet therapy following endovascular treatments. In the pre-clinical setting, system 10 will provide insights supporting the development of novel generations of neurovascular devices.

Study Limitations

The ability to inject contrast media and achieve a clear optical window for imaging of neurovascular arteries was investigated in a bench model of the circle of Willis. Substantial efforts were made to reproduce patient circulation, including pulsatile blood flow, physiological flow rates, vessel caliber, and capillary resistance. However, the use of in vitro models may be unable to capture the large spectrum of anatomical variations and disease conditions encountered in patient cerebrovasculature. In applicant's studies, a higher viscosity agent was more effective in successfully displacing blood and obtaining a clear field-of-view. In human clinical practice, other factors such as intracranial artery disease, aging, and consequent reduction of blood flow may permit the use of lower viscosity agents, such as saline or reduced viscosity contrast. In these conditions, injection at lower rates may also be possible and provide sufficient clearance for system 10 image acquisitions. Furthermore, the use of low molecular weight dextran has been successfully demonstrated for coronary imaging, its safety investigated for intracranial use, and future studies may possibly explore its use for system 10 imaging.

Patient-Specific Vascular Model of the Circle of Willis

A patient-specific vascular model including the entire circle of Willis was used to investigate optimal blood clearing protocols at different anatomical locations including the ICA, the MCA, the intradural VA, and the basilar arteries, reference FIG. 21. This model has been previously used in similar studies. Multiple sensors were used in applicant's studies to constantly measure the ICA, MCA, and BA flow rates and pressure to ensure reproduction of clinically relevant values. Swine blood was maintained at 37° C. and circulated using a pulsatile pump. The resistance of the outlets was adjusted to achieve physiologically representative flow rates through each branch of the model. Blood pressure and flow rate were constantly monitored and adjusted to maintain physiological values of approximately 250 ml/min in the ICA, 140 ml/min in the MCA, and 160 ml/min in the BA.

Animal Model and Preparation

A Yorkshire swine model ranging between 40-70 kg (n=8) was used in applicant's studies. All procedures were performed under general anesthesia. The animals were pre-anesthetized by a subcuticular injection of glycopyrrolate (0.01 mg/kg). Anesthesia was induced by an intramuscular injection of tiletamine (Telazol, 4.4 mg/kg), ketamine (2.2 mg/kg), and xylazine (2.2 mg/kg) and was maintained through mechanical ventilation of 1-3% isoflurane. During the procedures, the following vital parameters were monitored continuously and recorded: heart and respiratory rate, invasive blood pressure, oxygen saturation, end-tidal CO2, and temperature.

A model of elevated vascular tortuosity was obtained by the means of a flexed forelimb model. This technique is able to provide severe tortuosity in brachial arteries, resulting in radii of curvature similar to the ones encountered in the human ICA. After the surgical exposure of the right femoral artery, a 10F introducer sheath was inserted for endovascular access and a 0.058-inch Navien™ (Medtronic) was navigated through the proximal segment of the brachial artery allowing the deployment of imaging probe 100 to the target anatomy.

The 0.058-inch intracranial support catheter was subsequently navigated into the internal maxillary artery (IMAX). Sixteen (n=16) FDS were deployed bilaterally into the IMAX. A Pipeline FDS (Medtronic) was used in half of the arteries (n=8), and a Surpass FDS (Stryker neurovascular) was implanted in the other half (n=8) by the means of conventional endovascular surgery techniques. Following FDS implantation, an ICS was deployed in each IMAX resulting in a partially overlapping segment. Wingspan stents (Stryker Neurovascular) were implanted in a total of 5 arteries, Neuroform stents (Stryker Neurovascular) in 6 arteries, and Solitaire AB stents (Medtronic) in 4 arteries, for a total of 15 devices. In one single case, no ICS was deployed due to a thrombotic occlusion of the artery at the distal end of the FDS. In addition, a Precise Pro Carotid stent system (Cordis) was implanted in a subset of the animals in the common carotid artery (n=5).

Acquisition of Imaging Data

System 10 imaging was performed bilaterally in swine brachial arteries of all non-human animals (n=16). Contrast media (Omnipaque) was injected by the means of a 5F intermediate catheter to displace blood from the arterial lumen. Intravascular system 10 images were acquired in all IMAX arteries, following the deployment of FDS and ICS devices, obtaining a total of 31 imaging runs. Sixteen (n=16) of these imaging data sets were acquired following the FDS implantation. The additional datasets (n=15) were obtained following the ICS implantation partially overlapping with the FDS. Similarly, digital subtraction angiography (DSA), non-subtracted cineangiography, and full-scale, small FOV cone-beam CT images (Philips Healthcare) were acquired for each vessel using standard imaging techniques, obtaining 31 imaging runs for each modality.

Analysis of Neurovascular Devices

Co-registration of the imaging data from the different modalities was obtained using the distal and proximal edges of the FDS and ICS as reference markers. Five millimeter (5 mm) long regions of interests (ROI) were defined at the proximal and distal edges of all devices. For each ROI, the locations containing the largest clot and the most severe malapposition were matched between DSA, system 10, and the reconstructed CBCT cross-sectional images. A binary scoring system was used to classify all images for the presence or absence of clots and device malapposition. Altogether, 160 angiographic projections, 160 System 10 images, and 160 CBCT cross-sectional images were analyzed by three experienced neurointerventionalists in a blinded fashion.

Ex Vivo Segments of Intracranial Artery

To compare system 10 imaging of intracranial atherosclerotic plaques with histopathology, arterial segments were obtained from cadavers older than 70 years of age with a history of smoking and coronary and/or peripheral artery disease. The intracranial vasculature of three cadavers was explored, and arteries appearing to contain atherosclerotic disease were harvested (n=10), including distal segments of the ICA (n=2), proximal and distal MCA (n=4), BA (n=2) and intradural VA (n=2). Specimens were traditionally fixated with a 10% formalin solution prior to being harvested and subsequently the specimens were submerged in saline for system 10 image acquisitions. Multiple data sets sampling the entire length of each artery were obtained. An expert system 10 image reader identified regions of interest (ROI) containing atherosclerotic disease using previously established criteria for fibrotic, fibrocalcific and necrotic core plaques (n=3). A visible light indicator emitted by image probe 100 was used to mark each ROI on the different specimens. The corresponding tissue samples were subsequently embedded in paraffin, sectioned in 5 µm slices, and processed for Sudan's black, Hematoxylin and Eosin, van Gieson's, Movat Pentachrome, and Trichrome staining.

Statistical Analysis

Unless otherwise specified, data are presented as mean±standard deviation. Fleiss' kappa statistics was used to assess and quantify the agreement between the three different image raters classifying DSA, CBCT and system 10 images (inter-operator variability).

Three-Dimensional System 10 Renderings

Cross-sectional images were segmented following previously established criteria (13) using software ImageJ (36). Intraluminal clots, struts of neurovascular devices, and the contour of the vessel wall were manually traced and labelled. System 10 data were rendered in color using the following scheme: red, artery wall; purple, intraluminal clots; silver, metallic struts. The segmented data sets were imported into a volume-rendering DICOM visualization software (OsiriX MD v10.0.2, Pixmeo SARL, Bernex, Switzerland), after an automatic frame-to-frame registration to correct for motion artifacts generated by the mechanical scanning of the catheter. Perspective volume rendering techniques using cut surfaces and fly-through methods with different opacity tables were used for visualization, similar to previous studies (14, 37).

The above-described embodiments should be understood to serve only as illustrative examples; further embodiments are envisaged. Any feature described herein in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

What is claimed is:

1. An imaging system for a patient comprising:
   an imaging probe, comprising:
      an elongate shaft comprising a proximal end, a distal portion,
      and a lumen extending between the proximal end and the distal portion;
      a rotatable optical core comprising a proximal end and a distal end, wherein at least a portion of the rotatable optical core is positioned within the lumen of the elongate shaft; and
      an optical assembly positioned proximate the distal end of the rotatable optical core, the optical assembly configured to direct light to tissue and collect reflected light from the tissue; and the imaging system further comprising:
   a console comprising a light source having a coherence length greater than 10 mm; and
   an imaging assembly constructed and arranged to optically communicate with the imaging probe, the imaging assembly configured to emit light into the imaging probe and receive the reflected light collected by the optical assembly;
      wherein the imaging probe further comprises a scan range of no less
      than 6 mm, and wherein at least the distal portion of the elongate shaft comprises an outer diameter of no more than 0.034".

2. The system according to claim 1, wherein the outer diameter of at least the distal portion of the elongate shaft comprises an outer diameter of no more than 0.030".

3. The system according to claim 2, wherein the outer diameter of at least the distal portion of the elongate shaft comprises an outer diameter of no more than 0.025".

4. The system according to claim 3, wherein the outer diameter of at least the distal portion of the elongate shaft comprises an outer diameter of no more than 0.020".

5. The system according to 4, wherein the outer diameter of at least the distal portion of the elongate shaft comprises an outer diameter of no more than 0.016".

6. The system according to claim 1, further configured to perform a pre-treatment imaging procedure of a lesion comprising a diameter of less than 0.080".

7. The system according to claim 6, wherein the pre-treatment imaging procedure comprises a pullback procedure comprising pullback distance of at least 7.5 cm.

8. The system according to claim 7, wherein the pullback distance is at least 10 cm.

9. The system according to claim 8, wherein the pullback distance is at least 15 cm.

10. The system according to claim 7, wherein the pullback procedure is configured to be performed at a rate of at least 25 mm/sec.

11. The system according to claim 7, wherein the pullback procedure is configured to be performed within a time period of no more than 4 seconds.

12. The system according to claim 6, wherein the lesion comprises a stenosis, and wherein the distal portion of the imaging probe is configured to be inserted through the stenosis.

13. The system according to claim 1, further comprising a guidewire, and wherein the guidewire comprises a diameter of 0.014".

14. The system according to claim 13, wherein the guidewire And the imaging probe comprise a combined diameter of less than 0.044".

15. The system according to claim 1, wherein the scan range is no less than 7 mm.

16. The system according to claim 1, wherein the scan range is no less than 11 mm.

17. The system according to claim 1, wherein the imaging probe further comprises a dampening fluid positioned between the elongate shaft and the rotatable optical core, and wherein the dampening fluid is configured to reduce non-uniform rotation of the optical assembly.

18. The system according to claim 17, wherein the imaging probe further comprises a fluid pressurization element configured to increase the pressure of the damping fluid to reduce a presence of bubbles proximate the optical assembly.

19. The system according to claim 1, wherein the system is configured to provide treatment information, and wherein the treatment information is used by an operator to at least one of plan a treatment or predict a treatment outcome.

20. The system according to claim 19, wherein the treatment information is based on OCT data gathered by the imaging probe.

21. The system according to claim 20, further comprising a second imaging device configured to gather non-OCT data, and wherein the treatment information is further based on the non-OCT data.

22. The system according to claim 21, wherein the second imaging device is configured to gather non-OCT data comprising angiography data.

23. The system according to claim 1, wherein the system is configured to produce an assessment of disease severity.

24. The system according to claim 23, wherein the assessment comprises at least one of a quantified assessment plan or a qualitative assessment.

25. The system according to claim 1, wherein the system is configured to accurately capture a clot comprising a wavelength of 5 μm or more, 10 μm or more, or 30 μm or more.

* * * * *

UNITED STATES PATENT AND TRADEMARK OFFICE
CERTIFICATE OF CORRECTION

PATENT NO. : 12,239,412 B2
APPLICATION NO. : 17/603689
DATED : March 4, 2025
INVENTOR(S) : Christopher C. Petroff et al.

It is certified that error appears in the above-identified patent and that said Letters Patent is hereby corrected as shown below:

In the Claims

Column 58, Line 55, Claim 5, insert --claim-- before "4".

Column 59, Line 15, Claim 14, replace "And" with "and".

Column 60, Line 1, Claim 18, replace "damping" with "dampening".

Signed and Sealed this
Seventeenth Day of June, 2025

Coke Morgan Stewart
*Acting Director of the United States Patent and Trademark Office*